United States Patent
McElroy et al.

(10) Patent No.: US 8,217,038 B2
(45) Date of Patent: Jul. 10, 2012

(54) CANNABINOID RECEPTOR ANTAGONISTS/INVERSE AGONISTS USEFUL FOR TREATING METABOLIC DISORDERS, INCLUDING OBESITY AND DIABETES

(75) Inventors: John F. McElroy, Wilmington, DE (US); Robert J. Chorvat, West Chester, PA (US)

(73) Assignee: Jenrin Discovery, Inc., West Chester, PA (US)

( * ) Notice: Subject to any disclaimer, the term of this patent is extended or adjusted under 35 U.S.C. 154(b) by 0 days.

(21) Appl. No.: 12/900,252

(22) Filed: Oct. 7, 2010

(65) Prior Publication Data

US 2011/0257178 A1    Oct. 20, 2011

Related U.S. Application Data

(60) Provisional application No. 61/249,461, filed on Oct. 7, 2009.

(51) Int. Cl.
| | |
|---|---|
| A61K 31/5377 | (2006.01) |
| A61K 31/454 | (2006.01) |
| A61K 31/41 | (2006.01) |
| A61K 31/4155 | (2006.01) |
| A61K 31/415 | (2006.01) |
| C07D 413/02 | (2006.01) |
| C07D 401/02 | (2006.01) |
| C07D 257/02 | (2006.01) |
| C07D 231/06 | (2006.01) |

(52) U.S. Cl. ............... 514/236.5; 514/326; 514/382; 514/403; 544/140; 546/211; 548/251; 548/252; 548/370.1

(58) Field of Classification Search ............... 514/236.5, 514/326, 382, 403; 544/140; 546/211; 548/251, 548/252, 370.1
See application file for complete search history.

(56) References Cited

U.S. PATENT DOCUMENTS

| | | | |
|---|---|---|---|
| 5,250,532 | A | 10/1993 | McLaren et al. |
| 5,624,941 | A | 4/1997 | Barth et al. |
| 6,476,060 | B2 | 11/2002 | Lange et al. |
| 6,974,810 | B2 | 12/2005 | Lange et al. |
| 7,482,470 | B2 | 1/2009 | McElroy et al. |
| 7,528,162 | B2 | 5/2009 | Kruse et al. |
| 7,655,685 | B2 | 2/2010 | McElroy et al. |
| 7,666,889 | B2 | 2/2010 | McElroy et al. |
| 2007/0142362 | A1 | 6/2007 | Lange et al. |
| 2010/0105751 | A1 | 4/2010 | McElroy et al. |
| 2010/0152260 | A1 | 6/2010 | McElroy et al. |

FOREIGN PATENT DOCUMENTS

EP    1429761 B2    11/2006

OTHER PUBLICATIONS

PCT/US10/51834 International Search Report and Written Opinion, Dec. 14, 2010.
Stradivarius (Strategy to Reduce Athersclerosis Development InVolving Administration of Rimonabant—the Intravascular Ultrasound Study), ClinicalTrials.gov, http://clinicaltrials.gov/ct2/show/study/NCT00124332, Jul. 26, 2005.
Lange, J.H.M. et al.; Synthesis, Biological Properties and Molecular Investigations of Novel 3,4-Diarylpyrazolines as Potent and Selective CB1 Cannabinoid Receptor Antagonists; J. Med. Chem. 2004, 47, 627-643.
Remington et al.; The Science and Practice of Pharmacy, 2000, Lippincott Williams and Wilkins, 20th Edition, pp. 218-220.
Wierzbicki, A.S., Rimonabant: endocannabinoid inhibition for the metabolic syndrome, Drug Focus 2006, 60(12), 1697-1706.
Pi-Sunyer, F.X., Effect of Rimonabant, a Cannabinoid-1 Receptor Blocker, on Weight and Cardiometabolic Risk Factors in Overweight or Obese Patients, JAMA 2006, 297(7), 761-775.
Solvay's SLV319 Obesity Candidate Treatment Advances in Phase II Clinical Trials, Solvay Press Release, Dec. 8, 2006.
Begum, S. et. al., Cell-type-specific regulation of distinct sets of gene targets by Pax3 and Pax3/FKHR, Oncogene 2005, 24, 1860-72.
Santoro A. et at., Rimonabant inhibits human colon cancer cell growth and reduces the formation of precancerous lesions in the mouse colon, Int. J. Cancer 2009, 125, 996-1003.
Bifulco, M. et al., A new strategy to block tumor growth by inhibiting endocannabinoid inactivation, FASEB Journal 2004, 18, 1606-8.
Sarnataro, D. et al., The Cannabinoid CB1 Receptor Antagonist Rimonabant (SR141716) Inhibits Human Breast Cancer Cell Proliferation through a Lipid Raft-Mediated Mechansim, Molecular Pharmacology 2006, 70, 1298-1306.
Deveaux, V. et al., Cannabinoid CB2 Receptor Potentiates Obesity-Associated Inflammation, Insulin Resistance and Hepatic Steatosis, PLoS One 2009, 4(6), 1-12 (e5844).

*Primary Examiner* — Rebecca Anderson
*Assistant Examiner* — Samantha Shterengarts
(74) *Attorney, Agent, or Firm* — Vance Intellectual Property, PC

(57) ABSTRACT

The present invention provides novel pyrazolines that are useful as cannabinoid receptor blockers and pharmaceutical compositions thereof and methods of using the same for treating obesity, diabetes, inflammatory disorders, cardiometabolic disorders, hepatic disorders, and/or cancers.

14 Claims, No Drawings

CANNABINOID RECEPTOR ANTAGONISTS/INVERSE AGONISTS USEFUL FOR TREATING METABOLIC DISORDERS, INCLUDING OBESITY AND DIABETES

CROSS-REFERENCE TO RELATED APPLICATIONS

The present application claims priority benefit under 35 U.S.C. §119(e) of U.S. Provisional Patent Application Ser. No. 61/249,461 filed 7 Oct. 2009. The disclosure this application is incorporated herein by reference.

FIELD OF THE INVENTION

The present invention provides pyrazoline cannabinoid receptor antagonists/inverse agonists and pharmaceutical compositions thereof and methods of using the same for treating conditions including obesity, diabetes, hepatic disorders, cardiometabolic disorders, and/or cancers.

BACKGROUND OF THE INVENTION

Obesity is associated with an increase in the overall amount of adipose tissue (i.e., body fat), especially adipose tissue localized in the abdominal area. Obesity has reached epidemic proportions in the United States. The prevalence of obesity has steadily increased over the years among all racial and ethnic groups. The most recent data from the Centers for Disease Control and Prevention, and the National Center for Health Statistics report 66% of the adult population overweight (BMI, 25.0-29.9), 31% obese (BMI, 30-39.9), and 5% extremely obese (BMI, $\geq$40.0). Among children aged 6 through 19 years, 32% were overweight and 17% were obese. This translates to 124 million Americans medically overweight, and 44 million of these deemed obese. Obesity is responsible for more than 300,000 deaths annually, and will soon overtake tobacco usage as the primary cause of preventable death in the United States. Obesity is a chronic disease that contributes directly to numerous dangerous co-morbidities, including type 2 diabetes, cardiometabolic diseases, hepatic disorders, cardiovascular disease, inflammatory diseases, premature aging, and some forms of cancer. Type 2 diabetes, a serious and life-threatening disorder with growing prevalence in both adult and childhood populations, is currently the 7$^{th}$ leading cause of death in the United States. Since more than 80% of patients with type 2 diabetes are overweight, obesity is the greatest risk factor for developing type 2 diabetes. Increasing clinical evidence indicates that the best way to control type 2 diabetes is to reduce weight.

The most popular over-the counter drugs for the treatment of obesity, phenylpropanolamine and ephedrine, and the most popular prescription drug, fenfluramine, were removed from the marketplace as a result of safety concerns. Drugs currently approved for the long-term treatment of obesity fall into two categories: (a) CNS appetite suppressants such as sibutramine and rimonabant, and (b) gut lipase inhibitors such as orlistat. CNS appetite suppressants reduce eating behavior through activation of the 'satiety center' in the brain and/or by inhibition of the 'hunger center' in the brain. Gut lipase inhibitors reduce the absorption of dietary fat from the gastrointestinal (GI) tract. Although appetite suppressants and gut lipase inhibitors work through very different mechanisms, they share in common the same overall goal of reducing body weight secondary to reducing the amount of calories that reach the systemic circulation. Unfortunately, these indirect therapies produce only a modest initial weight loss (approximately 5% compared to placebo) that is usually not maintained. After one or two years of treatment, most patients return to or exceed their starting weight. In addition, most approved anti-obesity therapeutics produce undesirable and often dangerous side effects that can complicate treatment and interfere with a patient's quality of life.

The lack of therapeutic effectiveness, coupled with the spiraling obesity epidemic, positions the 'treatment of obesity' as one of the largest and most urgent unmet medical needs. There is, therefore, a real and continuing need for the development of improved medications that treat or prevent obesity.

The endocanabinoid system, comprised of the canabinoid receptors (CB1 and CB2) and their endogenous ligands (e.g., anandamide, 2-AG), plays a prominent role in the control of food intake and energy metabolism. CB1 receptors are widely expressed in the brain, including cortex, hippocampus, amygdala, pituitary and hypothalamus. CB1 receptors have also been identified in numerous peripheral organs and tissues, including thyroid gland, adrenal gland, reproductive organs, adipose tissue, liver, muscle, pancreas, and gastrointestinal tract. CB2 receptors are localized almost exclusively in immune and blood cells [*Endocrine Reviews* 2006, 27, 73].

The plant-derived cannabinoid agonist $\Delta^9$-tetrahydrocannabinol ($\Delta^9$-THC), the main psychoactive component of marijuana, binds to both CB1 and CB2 receptors. $\Delta^9$-THC is widely reported to increase appetite and food intake (hyperphagia) in humans and in animals. This hyperphagic effect is largely blocked by pretreatment with selective CB 1 receptor blockers (i.e., CB1 blockers)(e.g., rimonabant (SR141716A, Acomplia®)), strongly supporting the belief that CB1 receptor activation mediates the hyperphagic effect of $\Delta^9$-THC, [*Endocrine Reviews* 2006, 27, 73].

In humans, rimonabant produces a clinically meaningful weight loss in obese patients. Obese patients also experience improvements in diabetic and cardiometabolic risk factors associated with obesity, including an increase in the level of high density lipoprotein cholesterol (HDL), and decreases in triglycerides, glucose, and hemoglobin A1c (HbA1c, a marker of cumulative exposure to glucose) levels. Rimonabant also produces greater reductions in abdominal fat deposits, which are a known risk factor for diabetes and heart disease [*Science* 2006, 311, 323]. Taken together, these improvements in adiposity and cardiometabolic risk factors produce an overall decrease in the prevalence of the metabolic syndrome [*Lancet* 2005, 365, 1389 and *NEJM* 2005, 353, 2121].

In patients with type 2 diabetes not currently treated with other anti-diabetic medications, rimonabant was shown to significantly improve blood sugar control and weight, as well as other risk factors such as HDL and triglycerides, when compared to placebo (*Lancet* 2006, 368(9548), 1660-72). After six months of treatment, HbA1c levels were significantly lowered by 0.8% from a baseline value of 7.9 as compared to a reduction of 0.3% in the placebo group. These results are consistent with preclinical studies that demonstrate improved glycemic and lipid control in diabetic and dyslipedemic mice, rats, and dogs (*Pharmacology Biochemistry & Behavior,* 2006, 84, 353; *American Journal of Physiology,* 2003, 284, R345; *American Diabetes Association Annual Meeting,* 2007; Abstract Number 0372-OR).

The beneficial effects of rimonabant on diabetic and cardiometabolic risk factors such as high blood pressure, insulin resistance, and eleveated triglycerides cannot be explained by diet-related weight loss alone. For example, in patients receiving 20 mg of rimonabant, only approximately 50% of the beneficial effects on triglycerides, fasting insulin, and insulin resistance can be accounted for by weight loss secondary to reduced food intake. These results suggest a direct pharmacological effect of CB1 antagonists on glucose and lipid metabolism, in addition to indirect effects on metabolism secondary to hypophagia-mediated weight loss [*Science*

2006, 311, 323 and *JAMA* 2006, 311, 323]. Taken together, these results suggest that CB1 antagonists might be effective in the treatment of diabetes, dyslipidemia, cardiovascular disorders (e.g., atherosclerosis, hypertension), and hepatic disorders (e.g., cirrhosis, fatty liver diseases), even in patients that are not clinically overweight or obese.

The CB1 receptor is one of the most abundant and widely distributed G protein-coupled receptors in the mammalian brain. It is believed that the appetite-suppressant properties of CB1 antagonists are mediated through an interaction with CB1 receptors in the hypothalamus (regulation of food intake), and in the mesolimbic region (rewarding properties of food). However, CB1 receptors are far more broadly distributed in brain (e.g., neocortex, hippocampus, thalamus, cerebellum, and pituitary), and while interacting with targeted CB1 receptors in hypothalamus and mesolimbic regions to suppress appetite, CB1 antagonists have equal access to non-targeted CB1 receptors that have little if any role in appetite control. Binding to non-targeted receptors can often lead to unwanted side effects of CNS drugs [*Endocrine Reviews* 2006, 27: 73]. The CB1 blockers rimonabant and taranabant produce psychiatric and neurological side effects. These include depressed mood, anxiety, irritability, insomnia, dizziness, headache, seizures, and suicidality.

These side effects are dose-related and appear pronounced at the most efficacious weight-reducing doses of rimonabant and taranabant (*JAMA* 2006, 311, 323; *Cell Metabolism* 2008, 7, 68). The occurrence of therapeutic efficacy (appetite suppression) and side effects over the same dose range strongly suggest that both effects are mediated through concurrent antagonism of CB1 receptors in both 'targeted' and 'non-targeted' brain regions. Brain-penetrant CB1 blockers do not selectively target CB1 receptors in efficacy brain regions, while ignoring CB1 receptors in side effect brain regions.

The beneficial effects of the CB1 antagonist rimonabant on body weight, adiposity, and diabetic and cardiometabolic risk factors such as high blood pressure, insulin resistance and blood lipids cannot be explained by weight loss derived from CNS-mediated appetite suppression alone [*JAMA* 2006, 311, 323]. Approximately 50% of the benefit is likely derived from an interaction with CB1 receptors in peripheral tissues known to play an active role in metabolism. These include adipose tissue, liver, muscle, pancreas, and gastrointestinal tract.

SLV319 (Compound AA) is a drug that is indicated for the treatment of obesity. Compounds like SLV319 and related compounds have been described in various publications including *J. Med. Chem.* 2004, 47(3), 627 and U.S. Pat. No. 6,476,060.

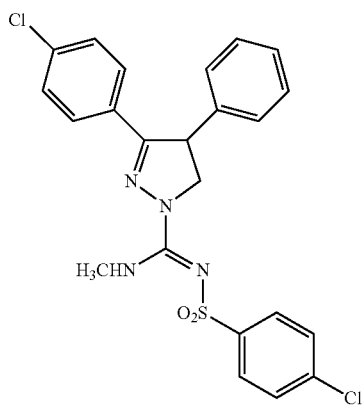

AA

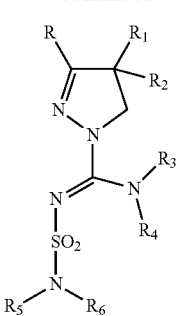

BB

Des-phenyl analogs of AA (e.g., Structure BB) are described in *Biorg. Med. Chem. Lett.* 2005, 15, 4793 and U.S. Pat. No. 6,974,810. Des-phenyl analogs of this sort are not considered to be part of the present invention.

In view of the above, it is highly desirable to find effective and highly selective CB1 receptor blockers with limited or no CNS adverse side effects, including mood disorders. Particularly, it is desirable to find compounds that preferentially target CB1 receptors in peripheral tissues (e.g., adipose tissue, liver, muscle, pancreas, and gastrointestinal tract), while sparing CB1 receptors in brain. In this way, peripherally-mediated beneficial effects of CB1 blockers should be maintained, whereas CNS side effects should be reduced or eliminated. This should provide a novel opportunity to develop safer alternatives to highly brain penetrant CB1 blockers for the prevention or treatment of obesity, diabetes, dyslipidemia, cardiovascular disorders, hepatic disorders, and/or cancers.

SUMMARY OF THE INVENTION

Accordingly, in an aspect, the present invention provides novel pyrazolines or pharmaceutically acceptable salts thereof that are CB1 receptor antagonists/inverse agonists.

In another aspect, the present invention provides novel pharmaceutical compositions, comprising: a pharmaceutically acceptable carrier and a therapeutically effective amount of at least one of the compounds of the present invention or a pharmaceutically acceptable salt form thereof.

In another aspect, the present invention provides novel methods for treating obesity, diabetes (e.g., insulin resistance, inadequate glucose tolerance, Type I diabetes, and Type II diabetes), dyslipidemias (e.g., elevated triglycerides and LDL, and low HDL), cardiovascular disorders (e.g., atherosclerosis and hypertension), inflammatory disorders (e.g., osteoarthritis, rheumatoid arthritis, inflammatory bowel diseases, and obesity-associated inflammation), hepatic disorders (e.g., nonalcoholic steatohepatitis (NASH), cirrhosis and fatty liver disease), and/or cancer (e.g., colon, breast, thyroid, and alveolar rhabdomyosarcoma cancer), comprising: administering to a mammal in need of such treatment a therapeutically effective amount of at least one of the compounds of the present invention or a pharmaceutically acceptable salt form thereof.

In another aspect, the present invention provides processes for preparing novel compounds.

In another aspect, the present invention provides novel compounds or pharmaceutically acceptable salts for use in therapy.

In another aspect, the present invention provides the use of novel compounds for the manufacture of a medicament for the treatment of obesity, diabetes, dyslipidemias, cardiovascular disorders, inflammatory disorders, hepatic disorders, and/or cancers.

These and other objects, which will become apparent during the following detailed description, have been achieved by the inventors' discovery that the presently claimed compounds or pharmaceutically acceptable salt forms thereof are expected to be effective CB1 receptor blockers.

DETAILED DESCRIPTION OF THE INVENTION

All references cited herein are hereby incorporated in their entirety herein by reference.

A CB1 blocker is a neutral CB1 receptor antagonist and/or a CB1 receptor inverse agonist.

The present invention is based on the finding that a CB1 receptor blocker has beneficial effects on cardiometabolic disorders including obesity, diabetes, and dyslipidemia that cannot be explained by weight loss derived from CNS-mediated appetite suppression alone, and that this effect is mediated, at least in part, through interaction at peripheral CB1 receptors. To this end, the present invention provides compounds that are designed to preferentially target CB1 receptors in peripheral tissues (e.g., adipose tissue, liver, muscle, pancreas, and gastrointestinal tract), while sparing CB1 receptors in brain. With these types of compounds, peripherally-mediated beneficial effects of CB1 blockers should be maintained, whereas CNS side effects should be reduced or eliminated.

The compounds of the present invention have been designed to have reduced CNS exposure by virtue of their inability or limited ability to penetrate the blood-brain barrier (BBB), or by their participation in active transport systems, thus reducing centrally mediated side-effects, a potential problem with many anti-obesity agents. It is expected that the peripherally restricted compounds of the present invention will have no or very limited CNS effects, including mood disorders, seizures, and suicidality. Thus, their peripherally mediated CB1 antaonistic properties should provide therapeutic agents with greater safety.

Moreover, if the maximum dosage of a drug used in the treatment of obesity, diabetes, dyslipidemia, cardiovascular disorders, inflammatory disorders, hepatic disorders, and/or cancers is limited as a result of CNS side effects (e.g., seizures, depression, anxiety, suicidality, movement disorders, and hyperactivity), incorporation of a peripherally restricting group in such a drug would lower the brain concentration of the drug relative to the concentration in the systemic circulation, thereby affording the opportunity to increase the dosage employed to treat the peripheral disorder (e.g., obesity, diabetes, dyslipidemia, cardiovascular disorders, inflammatory disorders, hepatic disorders, and/or cancers). The increased dosage may provide greater therapeutic efficacy, as well as a more rapid onset of therapeutic action.

In an embodiment, the present invention provides novel compounds of Formula I or a stereoisomer or pharmaceutically acceptable salt thereof:

I wherein:

X, Y, X', and Y', are independently selected from: H, $C_{1-6}$ alkyl, halogen, $CF_3$, O—$C_{1-6}$ alkyl, $NO_2$, $NR_2$, —CN, $O(CH_2)_nCO_2R$, $O(CH_2)_nCN$, $OCH_2CH=CH_2CO_2R$, $CH_2O$ $(CH_2)_nCO_2R$, $CH_2OCH_2CH=CHCO_2R$, $O(CH_2)_nPO$ $(OR)_2$, $CH_2O(CH_2)_nPO(OR)_2$, $NR^a(CH_2)_nCO_2R$, $NR^a$ $(CH_2)_nPO(OR)_2$, $NR^aCH_2CH=CHCO_2R$, $NR^aSO_2R$, $NR^aCO(CH_2)_nCO_2R$, $NR^aCO(CH_2)_nCONR^a_2$, $O(CH_2)_nC_6H_4CO_2R$, $O(CH_2)_nC_6H_4(CH_2)_nCO_2R$, $CH_2O$ $(CH_2)_nC_6H_4CO_2R$, $O(CH_2)_nC_6H_4CONR^a_2$, $O(CH_2)_nC_6H_4$ $(CH_2)_nCONR^a_2$, $O(CH_2)_nC_6H_4$-tetrazole, $CH_2O(CH_2)_n$ $C_6H_4CONR^a_2$, $CH_2O(CH_2)_nC_6H_4$-tetrazole, $O(CH_2)_nC_6H_4$ $(CH_2)_n$-tetrazole, $NR^a(CH_2)_nC_6H_4CO_2R$, $CH_2NR^a$ $(CH_2)_nC_6H_4CO_2R$, $NR^a(CH_2)_nC_6H_4(CH_2)_nCO_2R$, $NR^a$ $(CH_2)_nC_6H_4CONR^a_2$, $CH_2NR^a(CH_2)_nC_6H_4CONR^a_2$, $NR^a$ $(CH_2)_nC_6H_4(CH_2)_nCONR^a_2$, $NR^a(CH_2)_nC_6H_4$-tetrazole, $CH_2NR^a(CH_2)_nC_6H_4$-tetrazole, $NR^a(CH_2)_nC_6H_4(CH_2)_n$-tetrazole, $CONHOH$, $C(NH)NR^a_2$, $(CH_2)_nC(NH)NR^a_2$, $O(CH_2)_nCONR^a_2$, $O(CH_2)_nC(NH)NR^a_2$, $O(CH_2)_nC(NOH)$ $NR^a_2$, $CH_2O(CH_2)_nCONR^a_2$, $NR^a(CH_2)_nCONR^a_2$, $OCH_2CH=CHCONR^a_2$, $CH_2OCH_2CH=CHCONR^a_2$, $NR^aCH_2CH=CHCONR^a_2$, $(CH_2)_m$-tetrazole, $O(CH_2)_n$-tetrazole, $O(CH_2CH_2O)_pR$, $NR^a(CH_2CH_2O)_pR$, and $SO_2NHCH_3$;

Z is selected from: H, $C_{1-6}$ alkyl, OH, O—$C_{1-6}$ alkyl, $O(CH_2CH_2O)_pR$, $OC(O)$—$C_{1-6}$ alkyl, $O(CH_2)_nCO_2R$, $OCH_2CH=CHCO_2R$, $O(CH_2)_nPO(OR)_2$, $O(CH_2)_n$ $CONR^a_2$, $O(CH_2)_nC(NH)NH_2$, $O(CH_2)_nC(NOH)NR^a_2$, $OCH_2CH=CHCONR^a_2$, $O(CH_2)_n$-phenyl-$(CH_2)_mCO_2R$, and $O(CH_2)_n$-phenyl-$(CH_2)_m$-tetrazole;

Z' is selected from H, $CO_2R$, $CONR^a_2$, and $CONR^aCHA$-$CONR^a_2$;

Q is selected from: H, $C_{1-6}$ alkyl, $(CH_2CH_2O)_pR$, $(CH_2)_n$-aryl, $(CH_2)_m$-aryl-$(CH_2)_mCO_2R$, $(CH_2)_m$-aryl-$(CH_2)_mC(O)$ $NR^a_2$, $(CH_2)_n$-heteroaryl, $(CH_2)_m$ heteroaryl-$(CH_2)_mCO_2R$, $(CH_2)_m$-heteroaryl-$(CH_2)_mC(O)NR^a_2$, $(CH_2)_mCHA$ $(CH_2)_mC(O)NR^a_2$, $(CH_2)_mCAA"(CH_2)_mC(O)NR^a_2$, $(CH_2)_mCHA(CH_2)_mCO_2R$, $(CH_2)_mCAA"(CH_2)_mCO_2R$, $(CH_2)_mCHA(CH_2)_mSO_2NR^a_2$, $(CH_2)_mCHA(CH_2)_mSO_3R$, $(CH_2)_mCHA(CH_2)_mC(NH)NH_2$, $(CH_2)_mCHA(CH_2)_mC$ $(NOH)NH_2$, $(CH_2)_mCHA(CH_2)_mCONHCHA(CH_2)_mCO_2R$, $(CH_2)_mCAA"(CH_2)_mCONHCHA(CH_2)_mCO_2R$, $(CH_2)_m$ $CHA(CH_2)_mCONHCHA(CH_2)_mCONHCHA(CH_2)_mCO_2R$, $(CH_2)_mCHA(CH_2)_mCONHCHA(CH_2)_mCONR^a_2$, $(CH_2)_m$ $CAA"(CH_2)_mCONHCHA(CH_2)_mCONR^a_2$, $(CH_2)_mCHA$ $(CH_2)_mCONHCHA(CH_2)_mSO_2NR^a_2$, $(CH_2)_mCAA"$ $(CH_2)_mCONHCHA(CH_2)_mSO_2NR^a_2$, $(CH_2)_mCHA$ $(CH_2)_mCONHCHA(CH_2)_mCONHCHA(CH_2)_mCONR^a_2$, $C_3$-$C_6$-cyclic amino-$(CH_2)_mCO_2R$, $C_3$-$C_6$-cyclic amino-$(CH_2)_mCONR^a_2$, $C_3$-$C_6$-cycloalkylene-$(CH_2)_mCO_2R$, and $C_3$-$C_6$-cycloalkylene-$(CH_2)_mCONR^a_2$;

A is selected from H, $C_{1-6}$ alkyl, $(CH_2)_mC_{3-6}$-cycloalkyl, OH, $CH_2OH$, $CH(CH_3)OH$, $C(CH_3)_2OH$, $(CH_2)_nCO_2R^b$, $(CH_2)_nC(O)NR^b_2$, and $(CH_2)_m$-phenyl, wherein the phenyl is substituted with 0-3 groups selected from H, $C_{1-4}$ alkyl, halogen, $CF_3$, OH, O—$C_{1-4}$ alkyl, $NO_2$, —CN, $C(O)NH_2$, $C(NH)$ $NH_2$, and $NHSO_2CH_3$;

A" is $C_{1-6}$ alkyl;

alternatively, A and A" form a $C_{3-6}$ cycloalkyl group with the carbon to which they both are attached;

R is independently selected from H, $(CH_2)_m(CHR^b)_n$ $(CH_2)_mOH$, $CH(CH_2OH)_2$, $C_{1-6}$ alkyl, $C_{2-6}$ alkenyl, and $C_{2-6}$ alkynyl;

$R^a$ is independently selected from H, $(CH_2)_m(CHR)_n$ $(CH_2)_mOH$, $C_{1-6}$ alkyl, $C_{2-6}$ alkenyl, and $C_{2-6}$ alkynyl;

$R^b$ is independently selected from H, $C_{1-6}$ alkyl, $C_{2-6}$ alkenyl, and $C_{2-6}$ alkynyl;

$R^c$ is selected from H, $C_{1-6}$ alkyl, $C_{2-6}$ alkenyl, $C_{2-6}$ alkynyl, $C_{1-6}$ alkylidene-O—$C_{1-2}$ alkyl, $(CH_2)_mCHA(CH_2)_mC(O)NR^a{}_2$, $(CH_2)_mCAA''(CH_2)_mC(O)NR^a{}_2$, $(CH_2)_mCHA(CH_2)_mCO_2R$, $(CH_2)_mCAA''(CH_2)_mCO_2R$, $(CH_2)_mCHA(CH_2)_mSO_2NR^a{}_2$, $(CH_2)_mCHA(CH_2)_mSO_3R$, $(CH_2)_mCHA(CH_2)_mC(NH)NH_2$, $(CH_2)_mCHA(CH_2)_mC(NOH)NH_2$, $(CH_2)_mCHA(CH_2)_mCONHCHA(CH_2)_mCO_2R$, $(CH_2)_mCAA''(CH_2)_mCONHCHA(CH_2)_mCO_2R$, $(CH_2)_mCHA(CH_2)_mCONHCHA(CH_2)_mCONHCHA(CH_2)_mCO_2R$, $(CH_2)_mCHA(CH_2)_mCONHCHA(CH_2)_mCONR^a{}_2$, $(CH_2)_mCAA''(CH_2)_mCONHCHA(CH_2)_mCONR^a{}_2$, $(CH_2)_mCHA(CH_2)_mCONHCHA(CH_2)_mCONHCHA(CH_2)_mCONR^a{}_2$, $C_3$-$C_6$-cyclic amino-$(CH_2)_mCO_2R$, $C_3$-$C_6$-cyclic amino-$(CH_2)_mCONR^a{}_2$, $C_3$-$C_6$-cycloalkylene-$(CH_2)_mCO_2R$, and $C_3$-$C_6$-cycloalkylene-$(CH_2)_mCONR^a{}_2$;

$R^d$ is selected from H, $C_{1-6}$ alkyl, $C_{2-6}$ alkenyl, $C_{2-6}$ alkynyl, $OC_{3-4}$ alkenyl, $OC_{3-4}$ alkynyl, and $C_{1-6}$ alkylidene-O—$C_{1-2}$ alkyl;

alternatively, $R^c$ and $R^d$ taken together form —$(CH_2)_{n'}$—U—$(CH_2)_{n'}$—, and the ring formed by $N(R^c)CH_2R^d$ is substituted with 0-2 $R^e$ at other than group U;

U is selected from O, S, SO, $SO_2$, $CHR^e$, and $NR^e$;

$R^e$ is selected from H, $C_{1-6}$ alkyl, $C_{3-6}$ alkenyl, $C_{3-6}$ alkynyl, $C_{2-6}$ alkylidene-O—$C_{1-2}$ alkyl, $(CH_2)_mCO_2R$, $(CH_2)_mCONR^a{}_2$, $(CH_2)_mCONH(CH_2)_mCHA(CH_2)_mCONR^a{}_2$, and $(CH_2)_mCONH(CH_2)_mCHA(CH_2)_mCONR^a{}_2$;

p is independently selected from 2, 3, 4, 5, 6, 7, 8, 9, 10, 11, and 12;

m is independently selected from 0, 1, 2, 3, and 4; and, n is independently selected from 1, 2, 3, and 4; and n' is independently selected from 1 and 2;

provided that one of $R^d$, $R^e$, X, Y, X', Y', Z, Z', or Q is a group capable of reducing or limiting the CNS activity of compound I.

[1] In another embodiment, the present invention provides novel compounds of Formula I or a stereoisomer or pharmaceutically acceptable salt thereof:

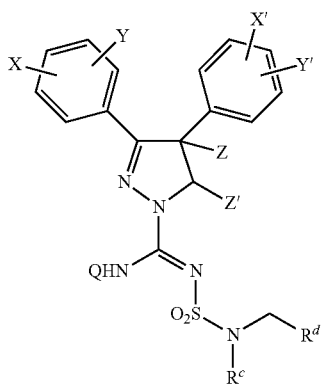

I wherein:

X, Y, X', and Y', are independently selected from: H, $C_{1-6}$ alkyl, halogen, $CF_3$, O—$C_{1-6}$ alkyl, $NO_2$, $NR_2$, —CN, $O(CH_2)_nCO_2R$, $O(CH_2)_nCN$, $OCH_2CH=CHCO_2R$, $CH_2O(CH_2)_nCO_2R$, $CH_2OCH_2CH=CHCO_2R$, $O(CH_2)_nPO(OR)_2$, $CH_2O(CH_2)_nPO(OR)_2$, $NR^a(CH_2)_nCO_2R$, $NR^a(CH_2)_nPO(OR)_2$, $NR^aCH_2CH=CHCO_2R$, $NR^aSO_2R$, $NR^aCO(CH_2)_nCO_2R$, $NR^aCO(CH_2)_nCONR^a{}_2$, $O(CH_2)_nC_6H_4CO_2R$, $O(CH_2)_nC_6H_4(CH_2)_nCO_2R$, $CH_2O(CH_2)_nC_6H_4CO_2R$, $O(CH_2)_nC_6H_4CONR^a{}_2$, $O(CH_2)_nC_6H_4(CH_2)_nCONR^a{}_2$, $O(CH_2)_nC_6H_4$-tetrazole, $CH_2O(CH_2)_nC_6H_4CONR^a{}_2$, $CH_2O(CH_2)_nC_6H_4$-tetrazole, $O(CH_2)_nC_6H_4(CH_2)_n$-tetrazole, $NR^a(CH_2)_nC_6H_4CO_2R$, $CH_2NR^a(CH_2)_nC_6H_4CO_2R$, $NR^a(CH_2)_nC_6H_4(CH_2)_nCO_2R$, $NR^a(CH_2)_nC_6H_4CONR^a{}_2$, $CH_2NR^a(CH_2)_nC_6H_4CONR^a{}_2$, $NR^a(CH_2)_nC_6H_4(CH_2)_nCONR^a{}_2$, $NR^a(CH_2)_nC_6H_4$-tetrazole, $CH_2NR^a(CH_2)_nC_6H_4$-tetrazole, $NR^a(CH_2)_nC_6H_4(CH_2)_n$-tetrazole, CONHOH, $C(NH)NR^a{}_2$, $(CH_2)_nC(NH)NR^a{}_2$, $O(CH_2)_nCONR^a{}_2$, $O(CH_2)_nC(NH)NR^a{}_2$, $O(CH_2)_nC(NOH)NR^a{}_2$, $CH_2O(CH_2)_nCONR^a{}_2$, $NR^a(CH_2)_nCONR^a{}_2$, $OCH_2CH=CHCONR^a{}_2$, $CH_2OCH_2CH=CHCONR^a{}_2$, $NR^aCH_2CH=CHCONR^a{}_2$, $(CH_2)_m$-tetrazole, $O(CH_2)_n$-tetrazole, $O(CH_2CH_2O)_pR$, $NR^a(CH_2CH_2O)_pR$, and $SO_2NHCH_3$;

Z is selected from: H, $C_{1-6}$ alkyl, OH, O—$C_{1-6}$ alkyl, $O(CH_2CH_2O)_pR$, OC(O)—$C_{1-6}$ alkyl, $O(CH_2)_nCO_2R$, $OCH_2CH=CHCO_2R$, $O(CH_2)_nPO(OR)_2$, $O(CH_2)_nCONR^a{}_2$, $O(CH_2)_nC(NH)NH_2$, $O(CH_2)_nC(NOH)NR^a{}_2$, $OCH_2CH=CHCONR^a{}_2$, $O(CH_2)_n$-phenyl-$(CH_2)_mCO_2R$, and $O(CH_2)_n$-phenyl-$(CH_2)_m$-tetrazole;

Z' is selected from H, $CO_2R$, $CONR^a{}_2$, and $CONR^aCHA$-$CONR^a{}_2$;

Q is selected from: H, $C_{1-6}$ alkyl, $(CH_2CH_2O)_pR$, $(CH_2)_n$-aryl, $(CH_2)_m$-aryl-$(CH_2)_mCO_2R$, $(CH_2)_m$-aryl-$(CH_2)_mC(O)NR^a{}_2$, $(CH_2)_n$-heteroaryl, $(CH_2)_m$ heteroaryl-$(CH_2)_mCO_2R$, $(CH_2)_m$-heteroaryl-$(CH_2)_mC(O)NR^a{}_2$, $(CH_2)_mCHA(CH_2)_mC(O)NR^a{}_2$, $(CH_2)_mCAA''(CH_2)_mC(O)NR^a{}_2$, $(CH_2)_mCHA(CH_2)_mCO_2R$, $(CH_2)_mCAA''(CH_2)_mCO_2R$, $(CH_2)_mCHA(CH_2)_mSO_2NR^a{}_2$, $(CH_2)_mCHA(CH_2)_mSO_3R$, $(CH_2)_mCHA(CH_2)_mC(NH)NH_2$, $(CH_2)_mCHA(CH_2)_mC(NOH)NH_2$, $(CH_2)_mCHA(CH_2)_mCONHCHA(CH_2)_mCO_2R$, $(CH_2)_mCAA''(CH_2)_mCONHCHA(CH_2)_mCO_2R$, $(CH_2)_mCHA(CH_2)_mCONHCHA(CH_2)_mCONHCHA(CH_2)_mCO_2R$, $(CH_2)_mCHA(CH_2)_mCONHCHA(CH_2)_mCONR^a{}_2$, $(CH_2)_mCAA''(CH_2)_mCONHCHA(CH_2)_mCONR^a{}_2$, $(CH_2)_mCHA(CH_2)_mCONHCHA(CH_2)_mSO_2NR^a{}_2$, $(CH_2)_mCAA''(CH_2)_mCONHCHA(CH_2)_mSO_2NR^a{}_2$, $(CH_2)_mCHA(CH_2)_mCONHCHA(CH_2)_mCONHCHA(CH_2)_mCONR^a{}_2$, $C_3$-$C_6$-cyclic amino-$(CH_2)_mCO_2R$, $C_3$-$C_6$-cyclic amino-$(CH_2)_mCONR^a{}_2$, $C_3$-$C_6$-cycloalkylene-$(CH_2)_mCO_2R$, and $C_3$-$C_6$-cycloalkylene-$(CH_2)_mCONR^a{}_2$;

A is selected from H, $C_{1-6}$ alkyl, $(CH_2)_mC_{3-6}$-cycloalkyl, OH, $CH_2OH$, $CH(CH_3)OH$, $C(CH_3)_2OH$, $(CH_2)_nCO_2R^b$, $(CH_2)_nC(O)NR^b{}_2$, and $(CH_2)_m$-phenyl, wherein the phenyl is substituted with 0-3 groups selected from H, $C_{1-4}$ alkyl, halogen, $CF_3$, OH, O—$C_{1-4}$ alkyl, $NO_2$, —CN, $C(O)NH_2$, $C(NH)NH_2$, and $NHSO_2CH_3$;

A'' is $C_{1-6}$ alkyl;

alternatively, A and A'' form a $C_{3-6}$ cycloalkyl group with the carbon to which they both are attached;

R is independently selected from H, $(CH_2)_m(CHR^b)_n(CH_2)_mOH$, $CH(CH_2OH)_2$, $C_{1-6}$ alkyl, $C_{2-6}$ alkenyl, and $C_{2-6}$ alkynyl;

$R^a$ is independently selected from H, $(CH_2)_m(CHR)_n(CH_2)_mOH$, $C_{1-6}$ alkyl, $C_{2-6}$ alkenyl, and $C_{2-6}$ alkynyl;

$R^b$ is independently selected from H, $C_{1-6}$ alkyl, $C_{2-6}$ alkenyl, and $C_{2-6}$ alkynyl;

$R^c$ is selected from H, $C_{1-6}$ alkyl, $C_{2-6}$ alkenyl, $C_{2-6}$ alkynyl, $C_{1-6}$ alkylidene-O—$C_{1-2}$ alkyl, $(CH_2)_mCHA(CH_2)_mC(O)NR^a{}_2$, $(CH_2)_mCAA''(CH_2)_mC(O)NR^a{}_2$, $(CH_2)_mCHA(CH_2)_mCO_2R$, $(CH_2)_mCAA''(CH_2)_mCO_2R$, $(CH_2)_mCHA(CH_2)_mSO_2NR^a{}_2$, $(CH_2)_mCHA(CH_2)_mSO_3R$, $(CH_2)_mCHA(CH_2)_mC(NH)NH_2$, $(CH_2)_mCHA(CH_2)_mC(NOH)NH_2$, $(CH_2)_mCHA(CH_2)_mCONHCHA(CH_2)_mCO_2R$, $(CH_2)_mCAA''(CH_2)_mCONHCHA(CH_2)_mCO_2R$, $(CH_2)_mCHA(CH_2)_mCONHCHA(CH_2)_mCONHCHA(CH_2)_mCO_2R$, $(CH_2)_mCHA(CH_2)_mCONHCHA(CH_2)_mCONR^a{}_2$, $(CH_2)_mCAA''(CH_2)_mCONHCHA(CH_2)_mCONR^a{}_2$, $(CH_2)_mCHA $(CH_2)_mCONHCHA(CH_2)_mCONHCHA(CH_2)_mCONR^a{}_2$, $C_3$-$C_6$-cyclic amino-$(CH_2)_mCO_2R$, $C_3$-$C_6$-cyclic amino-$(CH_2)_mCONR^a{}_2$, $C_3$-$C_6$-cycloalkylene-$(CH_2)_mCO_2R$, and $C_3$-$C_6$-cycloalkylene-$(CH_2)_mCONR^a{}_2$;

$R^d$ is selected from H, $C_{1-6}$ alkyl, $C_{2-6}$ alkenyl, $C_{2-6}$ alkynyl, $OC_{3-4}$ alkenyl, $OC_{3-4}$ alkynyl, and $C_{1-6}$ alkylidene-O—$C_{1-2}$ alkyl;

alternatively, $R^c$ and $R^d$ taken together form —$(CH_2)_{n'}$—U—$(CH_2)_{n'}$—, and the ring formed by $N(R^c)CH_2R^d$ is substituted with 0-2 $R^e$ at other than group U;

U is selected from O, S, SO, $SO_2$, $CHR^e$, and $NR^e$;

$R^e$ is selected from H, $C_{1-6}$ alkyl, $C_{3-6}$ alkenyl, $C_{3-6}$ alkynyl, $C_{2-6}$ alkylidene-O—$C_{1-2}$ alkyl, $(CH_2)_mCO_2R$, $(CH_2)_mCONR^a{}_2$, $(CH_2)_mCONH(CH_2)_mCHA$ $(CH_2)_mCONR^a{}_2$, and $(CH_2)_mCONH(CH_2)_mCHA$ $(CH_2)_mCONR^a{}_2$;

p is independently selected from 2, 3, 4, 5, 6, 7, 8, 9, 10, 11, and 12;

m is independently selected from 0, 1, 2, 3, and 4; and, n is independently selected from 1, 2, 3, and 4; and n' is independently selected from 1 and 2;

provided that at least one of (a)-(f) is satisfied:

a. at least one of X, Y, X', and Y' is other than H, $C_{1-6}$ alkyl, halogen, $CF_3$, O—$C_{1-6}$ alkyl, $NO_2$, $NR_2$, and $SO_2NHCH_3$;

b. Z is other than H, $C_{1-6}$ alkyl, OH, O—$C_{1-6}$ alkyl, and OC(O)—$C_{1-6}$ alkyl;

c. Z' is other than H;

d. Q is other than H, $C_{1-6}$ alkyl, $(CH_2)_n$-aryl, and $(CH_2)_n$-heteroaryl;

e. $R^c$ is other than H, $C_{1-6}$ alkyl, $C_{2-6}$ alkenyl, $C_{2-6}$ alkynyl, and $C_{1-6}$ alkylidene-O—$C_{1-2}$ alkyl; and/or f. $R^e$ is present and is other than H, $C_{1-6}$ alkyl, $C_{3-6}$ alkenyl, and $C_{3-6}$ alkynyl.

[2] In another embodiment, the present invention provides novel compounds of Formula Ia or a stereoisomer or pharmaceutically acceptable salt thereof:

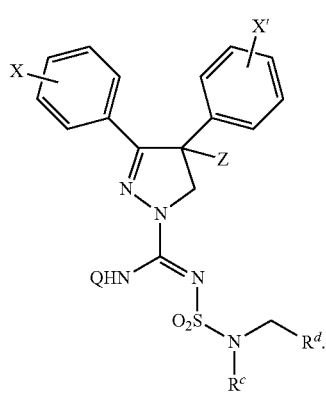

Ia

[3] In another embodiment, the present invention provides novel compounds of Formula Ib or a stereoisomer or pharmaceutically acceptable salt thereof:

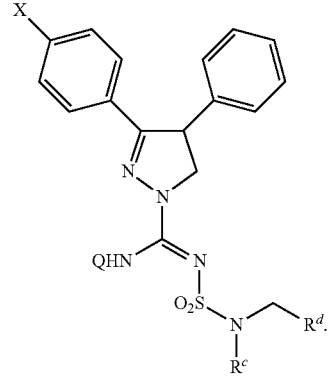

Ib

[4] In another embodiment, the present invention provides novel compounds of formula I or a stereoisomer or pharmaceutically acceptable salt thereof, wherein:

X, Y, X', and Y', are independently selected from: $O(CH_2)_nCO_2R$, $OCH_2CH=CHCO_2R$, $CH_2O(CH_2)_nCO_2R$, $CH_2OCH_2CH=CHCO_2R$, $O(CH_2)_nPO(OR)_2$, $CH_2O(CH_2)_nPO(OR)_2$, $NR^a(CH_2)_nCO_2R$, $NR^a(CH_2)_nPO(OR)_2$, $NR^aCH_2CH=CHCO_2R$, $NR^aSO_2R$, $NR^aCO(CH_2)_nCO_2R$, $NR^aCO(CH_2)_nCONR^a{}_2$, $O(CH_2)_nC_6H_4CO_2R$, $O(CH_2)_nC_6H_4(CH_2)_nCO_2R$, $CH_2O(CH_2)_nC_6H_4CO_2R$, $O(CH_2)_nC_6H_4CONR^a{}_2$, $O(CH_2)_nC_6H_4(CH_2)_nCONR^a{}_2$, $O(CH_2)_nC_6H_4$-tetrazole, $CH_2O(CH_2)_nC_6H_4CONR^a{}_2$, $CH_2O(CH_2)_nC_6H_4$-tetrazole, $O(CH_2)_nC_6H_4(CH_2)_n$-tetrazole, $NR^a(CH_2)_nC_6H_4CO_2R$, $CH_2NR^a(CH_2)_nC_6H_4CO_2R$, $NR^a(CH_2)_nC_6H_4(CH_2)_nCO_2R$, $NR^a(CH_2)_nC_6H_4CONR^a{}_2$, $CH_2NR^a(CH_2)_nC_6H_4CONR^a{}_2$, $NR^a(CH_2)_nC_6H_4(CH_2)_nCONR^a{}_2$, $NR^a(CH_2)_nC_6H_4$-tetrazole, $CH_2NR^a(CH_2)_nC_6H_4$-tetrazole, $NR^a(CH_2)_nC_6H_4(CH_2)_n$-tetrazole, CONHOH, $C(NH)NR^a{}_2$, $(CH_2)_nC(NH)NR^a{}_2$, $O(CH_2)_nCONR^a{}_2$, $O(CH_2)_nC(NH)NR^a{}_2$, $O(CH_2)_nC(NOH)NR^a{}_2$, $CH_2O(CH_2)_nCONR^a{}_2$, $NR^a(CH_2)_nCONR^a{}_2$, $OCH_2CH=CHCONR^a{}_2$, $CH_2OCH_2CH=CHCONR^a{}_2$, $NR^aCH_2CH=CHCONR^a{}_2$, $(CH_2)_m$-tetrazole, $O(CH_2)_n$-tetrazole, $O(CH_2CH_2O)_pR$, $NR^a(CH_2CH_2O)_pR$, and $SO_2NHCH_3$;

Z is selected from: H, $C_{1-6}$ alkyl, OH, O—$C_{1-6}$ alkyl, $O(CH_2CH_2O)_pR$, and OC(O)—$C_{1-6}$ alkyl;

Q is selected from: H, $C_{1-6}$ alkyl, $(CH_2)_n$-aryl, $(CH_2CH_2O)_pR$, and $(CH_2)_n$-heteroaryl;

R is independently selected from H, $(CH_2)_m(CHR^b)_n$ $(CH_2)_mOH$, $CH(CH_2OH)_2$, $C_{1-6}$ alkyl, $C_{2-6}$ alkenyl, and $C_{2-6}$ alkynyl;

$R^a$ is independently selected from H, $(CH_2)_m(CHR)_n$ $(CH_2)_mOH$, $C_{1-6}$ alkyl, $C_{2-6}$ alkenyl, and $C_{2-6}$ alkynyl;

$R^c$ is selected from H, $C_{1-6}$ alkyl, $C_{2-6}$ alkenyl, $C_{2-6}$ alkynyl, $C_{1-6}$ alkylidene-O—$C_{1-2}$ alkyl;

$R^d$ is selected from H, $C_{1-6}$ alkyl, $C_{2-6}$ alkenyl, $C_{2-6}$ alkynyl, $OC_{3-4}$ alkenyl, $OC_{3-4}$ alkynyl, and $C_{1-6}$ alkylidene-O—$C_{1-2}$ alky;

alternatively, $R^c$ and $R^d$ taken together form —$(CH_2)_{n'}$—U—$(CH_2)_{n'}$—, and the ring formed by $N(R^c)CH_2R^d$ is substituted with 0-2 $R^e$ at other than group U;

U is selected from O, S, SO, $SO_2$, $CHR^e$, and $NR^e$;

$R^e$ is selected from H, $C_{1-6}$ alkyl, $C_{3-6}$ alkenyl, $C_{3-6}$ alkynyl, and $C_{2-6}$ alkylidene-O—$C_{1-2}$ alkyl;

p is independently selected from 2, 3, 4, 5, 6, 7, 8, 9, 10, 11, and 12;

m is independently selected from 0, 1, 2, 3, and 4;

n is independently selected from 1, 2, 3, and 4; and n' is independently selected from 1 and 2.

[4a] In another embodiment, the present invention provides novel compounds of formula Ia or a stereoisomer or pharmaceutically acceptable salt thereof, wherein:

X and X', are independently selected from: $NR^aCO(CH_2)_nCONR^a{}_2$, $O(CH_2)_nC_6H_4CONR^a{}_2$, $O(CH_2)_nC_6H_4(CH_2)_nCONR^a{}_2$, $CH_2O(CH_2)_nC_6H_4CONR^a{}_2$, $NR^a(CH_2)_nC_6H_4CONR^a{}_2$, $CH_2NR^a(CH_2)_nC_6H_4CONR^a{}_2$, $NR^a(CH_2)_nC_6H_4(CH_2)_nCONR^a{}_2$, CONHOH, $C(NH)NR^a{}_2$, $(CH_2)_nC(NH)NR^a{}_2$, $O(CH_2)_nCONR^a{}_2$, $O(CH_2)_nC(NH)NR^a{}_2$, $O(CH_2)_nC(NOH)NR^a{}_2$, $CH_2O(CH_2)_nCONR^a{}_2$, $NR^a(CH_2)_nCONR^a{}_2$, $OCH_2CH=CHCONR^a{}_2$, $CH_2OCH_2CH=CHCONR^a{}_2$, $NR^aCH_2CH=CHCONR^a{}_2$, $O(CH_2CH_2O)_pR$, $NR^a(CH_2CH_2O)_pR$, and $SO_2NHCH_3$.

[4b] In another embodiment, the present invention provides novel compounds of formula Ib or a stereoisomer or pharmaceutically acceptable salt thereof, wherein:

X is selected from: $NR^aCO(CH_2)_nCONR^a{}_2$, $O(CH_2)_nC_6H_4CONR^a{}_2$, $O(CH_2)_nC_6H_4(CH_2)_nCONR^a{}_2$, $CH_2O(CH_2)_nC_6H_4CONR^a{}_2$, $NR^a(CH_2)_nC_6H_4CONR^a{}_2$, $CH_2NR^a(CH_2)_nC_6H_4CONR^a{}_2$, $NR^a(CH_2)_nC_6H_4(CH_2)_nCONR^a{}_2$, CONHOH, $C(NH)NR^a{}_2$, $(CH_2)_nC(NH)NR^a{}_2$, $O(CH_2)_nCONR^a{}_2$, $O(CH_2)_nC(NH)NR^a{}_2$, $O(CH_2)_nC(NOH)NR^a{}_2$, $CH_2O(CH_2)_nCONR^a{}_2$, $NR^a(CH_2)_nCONR^a{}_2$, $OCH_2CH=CHCONR^a{}_2$, $CH_2OCH_2CH=CHCONR^a{}_2$, $NR^aCH_2CH=CHCONR^a{}_2$, $O(CH_2CH_2O)_pR$, $NR^a(CH_2CH_2O)_pR$, and $SO_2NHCH_3$.

[5] In another embodiment, the present invention provides novel compounds of formula I or a stereoisomer or pharmaceutically acceptable salt thereof, wherein:

X, Y, X', and Y', are independently selected from: H, $C_{1-6}$ alkyl, halogen, $CF_3$, $O-C_{1-6}$ alkyl, $NO_2$, $NR_2$, $-CN$, $O(CH_2)_nCN$, $NR^aSO_2R$, and $SO_2NHCH_3$;

Z is selected from: $O(CH_2)_nCO_2R$, $OCH_2CH=CHCO_2R$, $O(CH_2)_nPO(OR)_2$, $O(CH_2)_nCONR^a{}_2$, $O(CH_2)_nC(NH)NH_2$, $O(CH_2)_nC(NOH)NR^a{}_2$, $OCH_2CH=CHCONR^a{}_2$, $O(CH_2)_n$-phenyl-$(CH_2)_mCO_2R$, and $O(CH_2)_n$-phenyl-$(CH_2)_m$-tetrazole;

Q is selected from: H, $C_{1-6}$ alkyl, $(CH_2)_n$-aryl, $(CH_2CH_2O)_pR$, and $(CH_2)_n$-heteroaryl;

R is independently selected from H, $(CH_2)_m(CHR^b)_n(CH_2)_mOH$, $CH(CH_2OH)_2$, $C_{1-6}$ alkyl, $C_{2-6}$ alkenyl, and $C_{2-6}$ alkynyl;

$R^a$ is independently selected from H, $(CH_2)_m(CHR)_n(CH_2)_mOH$, $C_{1-6}$ alkyl, $C_{2-6}$ alkenyl, and $C_{2-6}$ alkynyl;

$R^b$ is independently selected from H, $C_{1-6}$ alkyl, $C_{2-6}$ alkenyl, and $C_{2-6}$ alkynyl;

$R^c$ is selected from H, $C_{1-6}$ alkyl, $C_{2-6}$ alkenyl, $C_{2-6}$ alkynyl, and $C_{1-6}$ alkylidene-$O-C_{1-2}$ alkyl;

$R^d$ is selected from H, $C_{1-6}$ alkyl, $C_{2-6}$ alkenyl, $C_{2-6}$ alkynyl, $OC_{3-4}$ alkenyl, $OC_{3-4}$ alkynyl, and $C_{1-6}$ alkylidene-$O-C_{1-2}$ alkyl;

alternatively, $R^c$ and $R^d$ taken together form $-(CH_2)_{n'}-U-(CH_2)_{n'}-$, and the ring formed by $N(R^c)CH_2R^d$ is substituted with 0-2 $R^e$ at other than group U;

U is selected from O, S, SO, $SO_2$, $CHR^e$, and $NR^e$;

$R^e$ is selected from H, $C_{1-6}$ alkyl, $C_{3-6}$ alkenyl, $C_{3-6}$ alkynyl, and $C_{2-6}$ alkylidene-$O-C_{1-2}$ alkyl;

p is independently selected from 2, 3, 4, 5, 6, 7, 8, 9, 10, 11, and 12;

m is independently selected from 0, 1, 2, 3, and 4;

n is independently selected from 1, 2, 3, and 4; and, n' is independently selected from 1 and 2.

[5a] In another embodiment, the present invention provides novel compounds of formula I or a stereoisomer or pharmaceutically acceptable salt thereof, wherein:

Z is selected from: $O(CH_2)_nCO_2R$, $OCH_2CH=CHCO_2R$, $O(CH_2)_nCONR^a{}_2$, $O(CH_2)_nC(NH)NH_2$, $O(CH_2)_nC(NOH)NR^a{}_2$, and $OCH_2CH=CHCONR^a{}_2$.

[5b] In another embodiment, the present invention provides novel compounds of formula Ia or a stereoisomer or pharmaceutically acceptable salt thereof, wherein:

Z is selected from: $O(CH_2)_nCO_2R$, $OCH_2CH=CHCO_2R$, $O(CH_2)_nCONR^a{}_2$, $O(CH_2)_nC(NH)NH_2$, $O(CH_2)_nC(NOH)NR^a{}_2$, and $OCH_2CH=CHCONR^a{}_2$.

[5c] In another embodiment, the present invention provides novel compounds of formula Ib or a stereoisomer or pharmaceutically acceptable salt thereof, wherein:

Z is selected from: $O(CH_2)_nCO_2R$, $OCH_2CH=CHCO_2R$, $O(CH_2)_nCONR^a{}_2$, $O(CH_2)_nC(NH)NH_2$, $O(CH_2)_nC(NOH)NR^a{}_2$, and $OCH_2CH=CHCONR^a{}_2$.

[6] In another embodiment, the present invention provides novel compounds of formula I or a stereoisomer or pharmaceutically acceptable salt thereof, wherein:

X, Y, X', and Y', are independently selected from: H, $C_{1-6}$ alkyl, halogen, $CF_3$, $O-C_{1-6}$ alkyl, $NO_2$, $NR_2$, $-CN$, $O(CH_2)_nCN$, $NR^aSO_2R$, $O(CH_2CH_2O)_pR$, $NR^a(CH_2CH_2O)_pR$, and $SO_2NHCH_3$;

Z is selected from: H, $C_{1-6}$ alkyl, OH, $O-C_{1-6}$ alkyl, and $O(CH_2CH_2O)_pR$, $OC(O)-C_{1-6}$ alkyl;

Z' is selected from $CO_2R$ and $CONR^a{}_2$;

Q is selected from: H, $C_{1-6}$ alkyl, $(CH_2)_n$-aryl, $(CH_2CH_2O)_pR$, and $(CH_2)_n$-heteroaryl;

R is independently selected from H, $(CH_2)_m(CHR^b)_n(CH_2)_mOH$, $CH(CH_2OH)_2$, $C_{1-6}$ alkyl, $C_{2-6}$ alkenyl, and $C_{2-6}$ alkynyl;

$R^a$ is independently selected from H, $(CH_2)_m(CHR)_n(CH_2)_mOH$, $C_{1-6}$ alkyl, $C_{2-6}$ alkenyl, and $C_{2-6}$ alkynyl;

$R^b$ is independently selected from H, $C_{1-6}$ alkyl, $C_{2-6}$ alkenyl, and $C_{2-6}$ alkynyl;

$R^c$ is selected from H, $C_{1-6}$ alkyl, $C_{2-6}$ alkenyl, $C_{2-6}$ alkynyl, and $C_{1-6}$ alkylidene-$O-C_{1-2}$ alkyl;

$R^d$ is selected from H, $C_{1-6}$ alkyl, $C_{2-6}$ alkenyl, $C_{2-6}$ alkynyl, $OC_{3-4}$ alkenyl, $OC_{3-4}$ alkynyl, and $C_{1-6}$ alkylidene-$O-C_{1-2}$ alkyl;

alternatively, $R^c$ and $R^d$ taken together form $-(CH_2)_{n'}-U-(CH_2)_{n'}-$, and the ring formed by $N(R^c)CH_2R^d$ is substituted with 0-2 $R^e$ at other than group U;

U is selected from O, S, SO, $SO_2$, $CHR^e$, and $NR^e$;

$R^e$ is selected from H, $C_{1-6}$ alkyl, $C_{3-6}$ alkenyl, and $C_{3-6}$ alkynyl, $C_{2-6}$ alkylidene-$O-C_{1-2}$ alkyl;

p is independently selected from 2, 3, 4, 5, 6, 7, 8, 9, 10, 11, and 12;

m is independently selected from 0, 1, 2, 3, and 4;

n is independently selected from 1, 2, 3, and 4; and, n' is independently selected from 1 and 2.

[7] In another embodiment, the present invention provides novel compounds of formula Ic or a stereoisomer or pharmaceutically acceptable salt thereof:

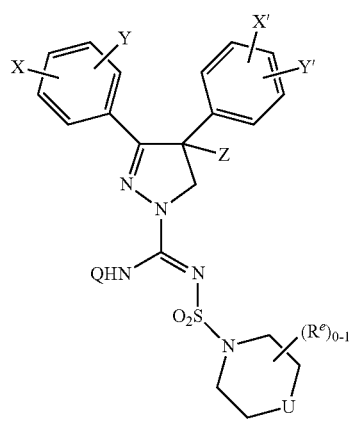

Ic

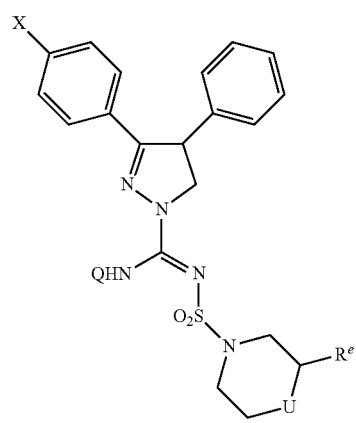

Id wherein:

X, Y, X', and Y' are individually selected from the following: H, $C_{1-4}$ alkyl, halogen, $CF_3$, O—$C_{1-4}$ alkyl, $NO_2$, —CN, $O(CH_2CH_2O)_pR$, $NR^a(CH_2CH_2O)_pR$, and $NR_2$;

Z is selected from: H, $C_{1-4}$ alkyl, OH, O—$C_{1-4}$ alkyl, acetyloxy, and propionyloxy;

Q is selected from: H, $C_{1-6}$ alkyl, $(CH_2CH_2O)_pR$, $(CH_2)_n$-aryl, $(CH_2)_m$-aryl-$(CH_2)_mCO_2R$, $(CH_2)_m$-aryl-$(CH_2)_mC(O)NR^a{}_2$, $(CH_2)_n$-heteroaryl, $(CH_2)_m$ heteroaryl-$(CH_2)_mCO_2R$, $(CH_2)_m$-heteroaryl-$(CH_2)_mC(O)NR^a{}_2$, $(CH_2)_mCHA(CH_2)_mC(O)NR^a{}_2$, $(CH_2)_mCAA''(CH_2)_mC(O)NR^a{}_2$, $(CH_2)_mCHA(CH_2)_mSO_2NR^a{}_2$, $(CH_2)_mCHA(CH_2)_mCONHCHA(CH_2)_mCONR^a{}_2$, $(CH_2)_mCAA''(CH_2)_mCONHCHA(CH_2)_mCONR^a{}_2$, $(CH_2)_mCHA(CH_2)_mCONHCHA(CH_2)_mSO_2NR^a{}_2$, $(CH_2)_mCAA''(CH_2)_mCONHCHA(CH_2)_mSO_2NR^a{}_2$, $(CH_2)_mCHA(CH_2)_mCONHCHA(CH_2)_mCONHCHA(CH_2)_mCONR^a{}_2$, $C_3$-$C_6$-cyclic amino-$(CH_2)_mCONR^a{}_2$, and $C_3$-$C_6$-cycloalkylene-$(CH_2)_mCONR^a{}_2$;

A is selected from H, $C_{1-4}$ alkyl, $(CH_2)_mC_{3-6}$-cycloalkyl, OH, $CH_2OH$, $CH(CH_3)OH$, $C(CH_3)_2OH$, $(CH_2)_nCO_2R^b$, $(CH_2)_nC(O)NR^b{}_2$, and $(CH_2)_m$-phenyl, wherein the phenyl is substituted with 0-3 groups selected from H, $C_{1-4}$ alkyl, halogen, $CF_3$, OH, O—$C_{1-4}$ alkyl, $NO_2$, —CN, $C(O)NH_2$, $C(NH)NH_2$, and $NHSO_2CH_3$;

R is independently selected from H, $C_{1-6}$ alkyl, $C_{2-6}$ alkenyl, and $C_{2-6}$ alkynyl;

$R^b$ is independently selected from H, $C_{1-6}$ alkyl, $C_{2-6}$ alkenyl, and $C_{2-6}$ alkynyl;

U is selected from O, SO, $SO_2$, $CHR^e$, and $NR^e$;

$R^e$ is selected from $(CH_2)_mCO_2R$, $(CH_2)_mCONR^a{}_2$, $(CH_2)_mCONH(CH_2)_mCHA(CH_2)_mCONR^a{}_2$, and $(CH_2)_mCONH(CH_2)_mCHA(CH_2)_mCONR^a{}_2$;

p is independently selected from 2, 3, 4, 5, 6, 7, and 8;

m is independently selected from 0, 1, 2, and 3;

n is independently selected from 1, 2, and 3;

n' is independently selected from 1 and 2; and/or provided that at least one of (a)-(c) is satisfied:

a. at least one of X, Y, X', and Y' is other than H, $C_{1-4}$ alkyl, halogen, $CF_3$, O—$C_{1-4}$ alkyl, $NO_2$, and $NR_2$;

b. Q is other than H, $C_{1-6}$ alkyl, $(CH_2)_n$-aryl, and $(CH_2)_n$-heteroaryl; and/or c. $R^e$ is present.

[7a] In another embodiment, the present invention provides novel compounds of formula Id or a stereoisomer or pharmaceutically acceptable salt thereof:

wherein:

X is selected from the following: H, $C_{1-4}$ alkyl, Cl, F, O—$C_{1-4}$ alkyl, $NO_2$, —CN, and $NR_2$;

Q is selected from: H, $C_{1-6}$ alkyl, $(CH_2)_m$-aryl-$(CH_2)_mC(O)NR^a{}_2$, $(CH_2)_m$-heteroaryl-$(CH_2)_mC(O)NR^a{}_2$, $(CH_2)_mCHA(CH_2)_mC(O)NR^a{}_2$, $(CH_2)_mCAA''(CH_2)_mC(O)NR^a{}_2$, $(CH_2)_mCHA(CH_2)_mSO_2NR^a{}_2$, $(CH_2)_mCHA(CH_2)_mCONHCHA(CH_2)_mCONR^a{}_2$, $(CH_2)_mCAA''(CH_2)_mCONHCHA(CH_2)_mCONR^a{}_2$, $(CH_2)_mCHA(CH_2)_mCONHCHA(CH_2)_mSO_2NR^a{}_2$, $(CH_2)_mCAA''(CH_2)_mCONHCHA(CH_2)_mSO_2NR^a{}_2$, $(CH_2)_mCHA(CH_2)_mCONHCHA(CH_2)_mCONHCHA(CH_2)_mCONR^a{}_2$, $C_3$-$C_6$-cyclic amino-$(CH_2)_mCONR^a{}_2$, and $C_3$-$C_6$-cycloalkylene-$(CH_2)_mCONR^a{}_2$;

A is selected from H, $C_{1-4}$ alkyl, $(CH_2)_mC_{3-6}$-cycloalkyl, OH, $CH_2OH$, $CH(CH_3)OH$, $C(CH_3)_2OH$, $(CH_2)_nCO_2R^b$, $(CH_2)_nC(O)NR^b{}_2$, and $(CH_2)_m$-phenyl, wherein the phenyl is substituted with 0-3 groups selected from H, $C_{1-4}$ alkyl, halogen, $CF_3$, OH, O—$C_{1-4}$ alkyl, $NO_2$, —CN, $C(O)NH_2$, $C(NH)NH_2$, and $NHSO_2CH_3$;

R is independently selected from H, $C_{1-6}$ alkyl, $C_{2-6}$ alkenyl, and $C_{2-6}$ alkynyl;

$R^b$ is independently selected from H, $C_{1-6}$ alkyl, $C_{2-6}$ alkenyl, and $C_{2-6}$ alkynyl;

U is selected from O, $CHR^e$, and $NR^e$;

$R^e$ is selected from H, $(CH_2)_mCO_2R$, $(CH_2)_mCONR^a{}_2$, $(CH_2)_mCONH(CH_2)_mCHA(CH_2)_mCONR^a{}_2$, and $(CH_2)_mCONH(CH_2)_mCHA(CH_2)_mCONR^a{}_2$;

m is independently selected from 0, 1, 2, and 3;

n is independently selected from 1, 2, and 3;

n' is independently selected from 1 and 2; and/or provided that at least one of (a)-(c) is satisfied:

a. X is other than H, $C_{1-6}$ alkyl, halogen, $CF_3$, O—$C_{1-6}$ alkyl, $NO_2$, and $NR_2$;

b. Q is other than H, $C_{1-6}$ alkyl, $(CH_2)_n$-aryl, and $(CH_2)_n$-heteroaryl; and/or c. $R^e$ is other than H.

[7b] In another embodiment, the present invention provides novel compounds of formula Id, wherein:

X is selected from the following: H, $C_{1-4}$ alkyl, Cl, F, O—$C_{1-4}$ alkyl, $NO_2$, —CN, and $NR_2$;

Q is selected from: $C_{1-6}$ alkyl, $(CH_2)_mCHA(CH_2)_mC(O)NR^a{}_2$, $(CH_2)_mCAA''(CH_2)_mC(O)NR^a{}_2$, and $(CH_2)_mCHA(CH_2)_mSO_2NR^a{}_2$;

A is selected from H, $C_{1-4}$ alkyl, OH, $CH_2OH$, $CH(CH_3)OH$, and $C(CH_3)_2OH$;

R is independently selected from H, $C_{1-4}$ alkyl, $C_{2-4}$ alkenyl, and $C_{2-4}$ alkynyl;

$R^b$ is independently selected from H, $C_{1-4}$ alkyl, $C_{2-4}$ alkenyl, and $C_{2-4}$ alkynyl;

U is selected from O, $CHR^e$, and $NR^e$;

$R^e$ is selected from H, $(CH_2)_m CO_2 R$, and $(CH_2)_m CONR^a_2$;

m is independently selected from 0, 1, and 2;

n is independently selected from 1 and 2;

n' is independently selected from 1 and 2; and/or provided that at least one of (a)-(c) is satisfied:
  a. X is other than H, $C_{1-6}$ alkyl, halogen, $CF_3$, $O-C_{1-6}$ alkyl, $NO_2$, and $NR_2$;
  b. Q is other than $C_{1-6}$ alkyl; and/or
  c. $R^e$ is other than H.

[8] In another embodiment, the present invention provides novel compounds of Formula I or a stereoisomer or pharmaceutically acceptable salt thereof, wherein:

X, Y, X', and Y', are independently selected from: H, $C_{1-6}$ alkyl, halogen, $CF_3$, $O-C_{1-6}$ alkyl, $NO_2$, $NR_2$, $-CN$, $O(CH_2)_n CN$, $NR^a SO_2 R$, $O(CH_2 CH_2 O)_p R$, $NR^a (CH_2 CH_2 O)_p R$, and $SO_2 NHCH_3$;

Z is selected from: H, $C_{1-6}$ alkyl, OH, $O-C_{1-6}$ alkyl, $O(CH_2 CH_2 O)_p R$, and $OC(O)-C_{1-6}$ alkyl;

Q is selected from: H, $C_{1-6}$ alkyl, $(CH_2)_n$-aryl, $(CH_2 CH_2 O)_p R$, and $(CH_2)_n$-heteroaryl;

A is selected from H, $C_{1-6}$ alkyl, $(CH_2)_m C_{3-6}$-cycloalkyl, OH, $CH_2 OH$, $CH(CH_3)OH$, $C(CH_3)_2 OH$, $(CH_2)_n CO_2 R^b$, $(CH_2)_n C(O)NR^b_2$, and $(CH_2)_m$-phenyl, wherein the phenyl is substituted with 0-3 groups selected from H, $C_{1-4}$ alkyl, halogen, $CF_3$, OH, $O-C_{1-4}$ alkyl, $NO_2$, $-CN$, $C(O)NH_2$, $C(NH)NH_2$, and $NHSO_2 CH_3$;

A" is $C_{1-6}$ alkyl;

R is independently selected from H, $(CH_2)_m (CHR^b)_n (CH_2)_m OH$, $CH(CH_2 OH)_2$, $C_{1-6}$ alkyl, $C_{2-6}$ alkenyl, and $C_{2-6}$ alkynyl;

$R^a$ is independently selected from H, $(CH_2)_m (CHR)_n (CH_2)_m OH$, $C_{1-6}$ alkyl, $C_{2-6}$ alkenyl, and $C_{2-6}$ alkynyl;

$R^b$ is independently selected from H, $C_{1-6}$ alkyl, $C_{2-6}$ alkenyl, and $C_{2-6}$ alkynyl;

$R^c$ is selected from $(CH_2)_m CHA(CH_2)_m C(O)NR^a_2$, $(CH_2)_m CAA''(CH_2)_m C(O)NR^a_2$, $(CH_2)_m CHA(CH_2)_m CO_2 R$, $(CH_2)_m CAA''(CH_2)_m CO_2 R$, $(CH_2)_m CHA(CH_2)_m SO_2 NR^a_2$, $(CH_2)_m CHA(CH_2)_m SO_3 R$, $(CH_2)_m CHA(CH_2)_m C(NH)NH_2$, $(CH_2)_m CHA(CH_2)_m C(NOH)NH_2$, $(CH_2)_m CHA(CH_2)_m CONHCHA(CH_2)_m CO_2 R$, $(CH_2)_m CAA''(CH_2)_m CONHCHA(CH_2)_m CO_2 R$, $(CH_2)_m CHA(CH_2)_m CONHCHA(CH_2)_m CO_2 R$, $(CH_2)_m CONHCHA(CH_2)_m CO_2 R$, $(CH_2)_m CHA(CH_2)_m CONHCHA(CH_2)_m CONR^a_2$, $(CH_2)_m CAA''(CH_2)_m CONHCHA(CH_2)_m CONR^a_2$, $(CH_2)_m CHA(CH_2)_m CONHCHA(CH_2)_m CONHCHA(CH_2)_m CONR^a_2$, $C_3$-$C_6$-cyclic amino-$(CH_2)_m CO_2 R$, $C_3$-$C_6$-cyclic amino-$(CH_2)_m CONR^a_2$, $C_3$-$C_6$-cycloalkylene-$(CH_2)_m CO_2 R$, and $C_3$-$C_6$-cycloalkylene-$(CH_2)_m CONR^a_2$;

$R^d$ is selected from H, $C_{1-6}$ alkyl, $C_{2-6}$ alkenyl, $C_{2-6}$ alkynyl, $OC_{3-4}$ alkenyl, $OC_{3-4}$ alkynyl, and $C_{1-6}$ alkylidene-$O-C_{1-2}$ alkyl;

p is independently selected from 2, 3, 4, 5, 6, 7, 8, 9, 10, 11, and 12;

m is independently selected from 0, 1, 2, 3, and 4; and, n is independently selected from 1, 2, 3, and 4.

[8a] In another embodiment, the present invention provides novel compounds of Formula Ia or a stereoisomer or pharmaceutically acceptable salt thereof, wherein:

X and X', are independently selected from: H, $C_{1-6}$ alkyl, halogen, $CF_3$, $O-C_{1-6}$ alkyl, $NO_2$, $NR_2$, $-CN$, $O(CH_2)_n CN$, $NR^a SO_2 R$, $O(CH_2 CH_2 O)_p R$, $NR^a (CH_2 CH_2 O)_p R$, and $SO_2 NHCH_3$;

Z is selected from: H, $C_{1-6}$ alkyl, OH, $O-C_{1-6}$ alkyl, $O(CH_2 CH_2 O)_p R$, and $OC(O)-C_{1-6}$ alkyl;

Q is selected from: H, $C_{1-6}$ alkyl, $(CH_2)_n$-aryl, $(CH_2 CH_2 O)_p R$, and $(CH_2)_n$-heteroaryl;

A is selected from H, $C_{1-6}$ alkyl, $(CH_2)_m C_{3-6}$-cycloalkyl, OH, $CH_2 OH$, $CH(CH_3)OH$, $C(CH_3)_2 OH$, $(CH_2)_n CO_2 R^b$, and $(CH_2)_n C(O)NR^b_2$;

A" is $C_{1-6}$ alkyl;

R is independently selected from H, $(CH_2)_m (CHR^b)_n (CH_2)_m OH$, $CH(CH_2 OH)_2$, $C_{1-6}$ alkyl, $C_{2-6}$ alkenyl, and $C_{2-6}$ alkynyl;

$R^a$ is independently selected from H, $(CH_2)_m (CHR)_n (CH_2)_m OH$, $C_{1-6}$ alkyl, $C_{2-6}$ alkenyl, and $C_{2-6}$ alkynyl;

$R^b$ is independently selected from H, $C_{1-6}$ alkyl, $C_{2-6}$ alkenyl, and $C_{2-6}$ alkynyl;

$R^c$ is selected from $(CH_2)_m CHA(CH_2)_m C(O)NR^a_2$, $(CH_2)_m CAA''(CH_2)_m C(O)NR^a_2$, $(CH_2)_m CHA(CH_2)_m SO_2 NR^a_2$, $(CH_2)_m CHA(CH_2)_m C(NH)NH_2$, $(CH_2)_m CHA(CH_2)_m CONHCHA(CH_2)_m CONR^a_2$, $(CH_2)_m CAA''(CH_2)_m CONHCHA(CH_2)_m CONR^a_2$, $(CH_2)_m CHA(CH_2)_m CONHCHA(CH_2)_m CONR^a_2$, $C_3$-$C_6$-cyclic amino-$(CH_2)_m CONR^a_2$, and $C_3$-$C_6$-cycloalkylene-$(CH_2)_m CONR^a_2$;

$R^d$ is selected from H, $C_{1-6}$ alkyl, $C_{2-6}$ alkenyl, $C_{2-6}$ alkynyl, $OC_{3-4}$ alkenyl, $OC_{3-4}$ alkynyl, and $C_{1-6}$ alkylidene-$O-C_{1-2}$ alkyl;

p is independently selected from 2, 3, 4, 5, 6, 7, 8, 9, 10, 11, and 12;

m is independently selected from 0, 1, 2, and 2; and, n is independently selected from 1 and 2.

[8b] In another embodiment, the present invention provides novel compounds of Formula Ib or a stereoisomer or pharmaceutically acceptable salt thereof, wherein:

X is selected from: H, $C_{1-4}$ alkyl, halogen, $CF_3$, $O-C_{1-4}$ alkyl, $NO_2$, $NR_2$, $-CN$, $O(CH_2)_n CN$, $NR^a SO_2 R$, $O(CH_2 CH_2 O)_p R$, $NR^a (CH_2 CH_2 O)_p R$, and $SO_2 NHCH_3$;

Z is selected from: H, $C_{1-4}$ alkyl, OH, $O-C_{1-4}$ alkyl, $O(CH_2 CH_2 O)_p R$, and $OC(O)-C_{1-4}$ alkyl;

Q is selected from: H, $C_{1-4}$ alkyl, $(CH_2)_n$-aryl, $(CH_2 CH_2 O)_p R$, and $(CH_2)_n$-heteroaryl;

A is selected from H, $C_{1-4}$ alkyl, $(CH_2)_m C_{3-6}$-cycloalkyl, OH, $CH_2 OH$, $CH(CH_3)OH$, $C(CH_3)_2 OH$, $(CH_2)_n CO_2 R^b$, and $(CH_2)_n C(O)NR^b_2$;

A" is $C_{1-4}$ alkyl;

R is independently selected from H, $(CH_2)_m (CHR^b)_n (CH_2)_m OH$, $CH(CH_2 OH)_2$, $C_{1-4}$ alkyl, $C_{2-4}$ alkenyl, and $C_{2-4}$ alkynyl;

$R^a$ is independently selected from H, $(CH_2)_m (CHR)_n (CH_2)_m OH$, $C_{1-4}$ alkyl, $C_{2-4}$ alkenyl, and $C_{2-4}$ alkynyl;

$R^b$ is independently selected from H, $C_{1-4}$ alkyl, $C_{2-4}$ alkenyl, and $C_{2-4}$ alkynyl;

$R^c$ is selected from $(CH_2)_m CHA(CH_2)_m C(O)NR^a_2$, $(CH_2)_m CAA''(CH_2)_m C(O)NR^a_2$, $(CH_2)_m CHA(CH_2)_m SO_2 NR^a_2$, $(CH_2)_m CHA(CH_2)_m C(NH)NH_2$, $(CH_2)_m CHA(CH_2)_m CONHCHA(CH_2)_m CONR^a_2$, $(CH_2)_m CAA''(CH_2)_m CONHCHA(CH_2)_m CONR^a_2$, $(CH_2)_m CHA(CH_2)_m CONHCHA(CH_2)_m CONHCHA(CH_2)_m CONR^a_2$, $C_3$-$C_6$-cyclic amino-$(CH_2)_m CONR^a_2$, and $C_3$-$C_6$-cycloalkylene-$(CH_2)_m CONR^a_2$;

$R^d$ is selected from H, $C_{1-4}$ alkyl, $C_{2-4}$ alkenyl, $C_{2-4}$ alkynyl, $OC_{3-4}$ alkenyl, $OC_{3-4}$ alkynyl, and $C_{1-4}$ alkylidene-$O-C_{1-2}$ alkyl;

p is independently selected from 2, 3, 4, 5, 6, 7, 8, 9, 10, 11, and 12;

m is independently selected from 0, 1, 2, and 2; and, n is independently selected from 1 and 2.

[9] In another embodiment, the present invention provides novel compounds of Formula I or a stereoisomer or pharmaceutically acceptable salt thereof, wherein:

X, Y, X', and Y', are independently selected from: H, $C_{1-6}$ alkyl, halogen, $CF_3$, O—$C_{1-6}$ alkyl, $NO_2$, $NR_2$, —CN, $NR^aSO_2R$, and $SO_2NHCH_3$;

Z is selected from: H, $C_{1-6}$ alkyl, OH, O—$C_{1-6}$ alkyl, $O(CH_2CH_2O)_pR$, and $OC(O)$—$C_{1-6}$ alkyl;

Q is selected from: $(CH_2)_mCHA(CH_2)_mC(O)NR^a_2$, $(CH_2)_mCAA"(CH_2)_mC(O)NR^a_2$, $(CH_2)_nCHA(CH_2)_mCO_2R$, $(CH_2)_mCAA"(CH_2)_mCO_2R$, $(CH_2)_mCHA(CH_2)_mSO_2NR^a_2$, $(CH_2)_mCHA(CH_2)_mSO_3R$, $(CH_2)_mCHA(CH_2)_mC(NH)NH_2$, $(CH_2)_mCHA(CH_2)_mC(NOH)NH_2$, $(CH_2)_mCHA(CH_2)_mCONHCHA(CH_2)_mCO_2R$, $(CH_2)_mCAA"(CH_2)_mCONHCHA(CH_2)_mCO_2R$, $(CH_2)_mCHA(CH_2)_mCONHCHA(CH_2)_mCONHCHA(CH_2)_mCO_2R$, $(CH_2)_mCHA(CH_2)_mCONHCHA(CH_2)_mCONR^a_2$, $(CH_2)_mCAA"(CH_2)_mCONHCHA(CH_2)_mCONR^a_2$, $(CH_2)_mCHA(CH_2)_mCONHCHA(CH_2)_mSO_2NR^a_2$, $(CH_2)_mCAA"(CH_2)_mCONHCHA(CH_2)_mSO_2NR^a_2$, $(CH_2)_mCHA(CH_2)_mCONHCHA(CH_2)_mCONHCHA(CH_2)_mCONR^a_2$, $C_3$-$C_6$-cyclic amino-$(CH_2)_mCO_2R$, $C_3$-$C_6$-cyclic amino-$(CH_2)_mCONR^a_2$, $C_3$-$C_6$-cycloalkylene-$(CH_2)_mCO_2R$, and $C_3$-$C_6$-cycloalkylene-$(CH_2)_mCONR^a_2$;

A is selected from H, $C_{1-6}$ alkyl, $(CH_2)_mC_{3-6}$-cycloalkyl, OH, $CH_2OH$, $CH(CH_3)OH$, $C(CH_3)_2OH$, $(CH_2)_nCO_2R^b$, $(CH_2)_nC(O)NR^b_2$, and $(CH_2)_m$-phenyl, wherein the phenyl is substituted with 0-3 groups selected from H, $C_{1-4}$ alkyl, halogen, $CF_3$, OH, O—$C_{1-4}$ alkyl, $NO_2$, —CN, $C(O)NH_2$, $C(NH)NH_2$, and $NHSO_2CH_3$;

A" is $C_{1-6}$ alkyl;

R is independently selected from H, $(CH_2)_m(CHR^b)_n(CH_2)_mOH$, $CH(CH_2OH)_2$, $C_{1-6}$ alkyl, $C_{2-6}$ alkenyl, and $C_{2-6}$ alkynyl;

$R^a$ is independently selected from H, $(CH_2)_m(CHR)_n(CH_2)_mOH$, $C_{1-6}$ alkyl, $C_{2-6}$ alkenyl, and $C_{2-6}$ alkynyl;

$R^b$ is independently selected from H, $C_{1-6}$ alkyl, $C_{2-6}$ alkenyl, and $C_{2-6}$ alkynyl;

$R^c$ is selected from H, $C_{1-6}$ alkyl, $C_{2-6}$ alkenyl, $C_{2-6}$ alkynyl, and $C_{1-6}$ alkylidene-O—$C_{1-2}$ alkyl;

$R^d$ is selected from H, $C_{1-6}$ alkyl, $C_{2-6}$ alkenyl, $C_{2-6}$ alkynyl, $OC_{3-4}$ alkenyl, $OC_{3-4}$ alkynyl, and $C_{1-6}$ alkylidene-O—$C_{1-2}$ alkyl;

alternatively, $R^c$ and $R^d$ taken together form —$(CH_2)_{n'}$—U—$(CH_2)_{n'}$—, and the ring formed by $N(R^c)CH_2R^d$ is substituted with 0-2 $R^e$ at other than group U;

U is selected from O, S, SO, $SO_2$, $CHR^e$, and $NR^e$;

$R^e$ is selected from H, $C_{1-6}$ alkyl, $C_{3-6}$ alkenyl, $C_{3-6}$ alkynyl, and $C_{2-6}$ alkylidene-O—$C_{1-2}$ alkyl;

p is independently selected from 2, 3, 4, 5, 6, 7, 8, 9, 10, 11, and 12;

m is independently selected from 0, 1, 2, 3, and 4;

n is independently selected from 1, 2, 3, and 4; and, n' is independently selected from 1 and 2.

[9a] In another embodiment, the present invention provides novel compounds of Formula Ia or a stereoisomer or pharmaceutically acceptable salt thereof, wherein:

X and X' are independently selected from: H, $C_{1-6}$ alkyl, halogen, $CF_3$, O—$C_{1-6}$ alkyl, $NO_2$, $NR_2$, —CN, $NR^aSO_2R$, and $SO_2NHCH_3$;

Z is selected from: H, $C_{1-6}$ alkyl, OH, and O—$C_{1-6}$ alkyl;

Q is selected from: $(CH_2)_mCHA(CH_2)_mC(O)NR^a_2$, $(CH_2)_mCAA"(CH_2)_mC(O)NR^a_2$, $(CH_2)_mCHA(CH_2)_mSO_2NR^a_2$, $(CH_2)_mCHA(CH_2)_mC(NH)NH_2$, $(CH_2)_mCHA(CH_2)_mCONHCHA(CH_2)_mCONR^a_2$, $(CH_2)_mCAA"(CH_2)_mCONHCHA(CH_2)_mCONR^a_2$, $(CH_2)_mCHA(CH_2)_mCONHCHA(CH_2)_mSO_2NR^a_2$, $(CH_2)_mCAA"(CH_2)_mCONHCHA(CH_2)_mSO_2NR^a_2$, $(CH_2)_mCHA(CH_2)_mCONHCHA(CH_2)_mCONHCHA(CH_2)_mCONR^a_2$, $C_3$-$C_6$-cyclic amino-$(CH_2)_mCO_2R$, $C_3$-$C_6$-cyclic amino-$(CH_2)_mCONR^a_2$, and $C_3$-$C_6$-cycloalkylene-$(CH_2)_mCONR^a_2$;

A is selected from H, $C_{1-6}$ alkyl, $(CH_2)_mC_{3-6}$-cycloalkyl, OH, $CH_2OH$, $CH(CH_3)OH$, $C(CH_3)_2OH$, $(CH_2)_nCO_2R^b$, and $(CH_2)_nC(O)NR^b_2$;

A" is $C_{1-6}$ alkyl;

R is independently selected from H, $(CH_2)_m(CHR^b)_n(CH_2)_mOH$, $CH(CH_2OH)_2$, $C_{1-6}$ alkyl, $C_{2-6}$ alkenyl, and $C_{2-6}$ alkynyl;

$R^a$ is independently selected from H, $(CH_2)_m(CHR)_n(CH_2)_mOH$, $C_{1-6}$ alkyl, $C_{2-6}$ alkenyl, and $C_{2-6}$ alkynyl;

$R^b$ is independently selected from H, $C_{1-6}$ alkyl, $C_{2-6}$ alkenyl, and $C_{2-6}$ alkynyl;

$R^c$ is selected from H, $C_{1-6}$ alkyl, $C_{2-6}$ alkenyl, $C_{2-6}$ alkynyl, and $C_{1-6}$ alkylidene-O—$C_{1-2}$ alkyl;

$R^d$ is selected from H, $C_{1-6}$ alkyl, $C_{2-6}$ alkenyl, $C_{2-6}$ alkynyl, $OC_{3-4}$ alkenyl, $OC_{3-4}$ alkynyl, and $C_{1-6}$ alkylidene-O—$C_{1-2}$ alkyl;

m is independently selected from 0, 1, and 2;

n is independently selected from 1 and 2; and, n' is independently selected from 1 and 2.

[9b] In another embodiment, the present invention provides novel compounds of Formula Ib or a stereoisomer or pharmaceutically acceptable salt thereof, wherein:

X is selected from: H, $C_{1-6}$ alkyl, halogen, $CF_3$, O—$C_{1-6}$ alkyl, $NO_2$, $NR_2$, and —CN;

Q is selected from: $(CH_2)_mCHA(CH_2)_mC(O)NR^a_2$, $(CH_2)_mCAA"(CH_2)_mC(O)NR^a_2$, $(CH_2)_mCHA(CH_2)_mSO_2NR^a_2$, $(CH_2)_mCHA(CH_2)_mC(NH)NH_2$, $(CH_2)_mCHA(CH_2)_mCONHCHA(CH_2)_mCONR^a_2$, $(CH_2)_mCAA"(CH_2)_mCONHCHA(CH_2)_mCONR^a_2$, $(CH_2)_mCHA(CH_2)_mCONHCHA(CH_2)_mSO_2NR^a_2$, $(CH_2)_mCAA"(CH_2)_mCONHCHA(CH_2)_mSO_2NR^a_2$, $(CH_2)_mCHA(CH_2)_mCONHCHA(CH_2)_mCONHCHA(CH_2)_mCONR^a_2$, $C_3$-$C_6$-cyclic amino-$(CH_2)_mCO_2R$, $C_3$-$C_6$-cyclic amino-$(CH_2)_mCONR^a_2$, and $C_3$-$C_6$-cycloalkylene-$(CH_2)_mCONR^a_2$;

A is selected from H, $C_{1-6}$ alkyl, $(CH_2)_mC_{3-6}$-cycloalkyl, OH, $CH_2OH$, $CH(CH_3)OH$, and $C(CH_3)_2OH$;

A" is $C_{1-4}$ alkyl;

R is independently selected from H, $(CH_2)_m(CHR^b)_n(CH_2)_mOH$, $CH(CH_2OH)_2$, $C_{1-4}$ alkyl, $C_{2-4}$ alkenyl, and $C_{2-4}$ alkynyl;

$R^a$ is independently selected from H, $(CH_2)_m(CHR)_n(CH_2)_mOH$, $C_{1-4}$ alkyl, $C_{2-4}$ alkenyl, and $C_{2-4}$ alkynyl;

$R^b$ is independently selected from H, $C_{1-4}$ alkyl, $C_{2-4}$ alkenyl, and $C_{2-4}$ alkynyl;

$R^c$ is selected from H, $C_{1-4}$ alkyl, $C_{2-4}$ alkenyl, $C_{2-4}$ alkynyl, and $C_{1-4}$ alkylidene-O—$C_{1-2}$ alkyl;

$R^d$ is selected from H, $C_{1-4}$ alkyl, $C_{2-4}$ alkenyl, $C_{2-4}$ alkynyl, $OC_{3-4}$ alkenyl, $OC_{3-4}$ alkynyl, and $C_{1-4}$ alkylidene-O—$C_{1-2}$ alkyl;

m is independently selected from 0, 1, and 2;

n is independently selected from 1 and 2; and, n' is independently selected from 1 and 2.

In another embodiment, the present invention provides novel pharmaceutical compositions, comprising: a pharmaceutically acceptable carrier and a therapeutically effective amount of a compound of the present invention or a pharmaceutically acceptable salt form thereof.

In another embodiment, the present invention provides a novel method of modulating the activity of CB1 receptors (e.g., periperhal CB1 receptors) in a patient, comprising: administering to a patient in need thereof a therapeutically effective amount of a compound of the present invention or a pharmaceutically acceptable salt form thereof.

In another embodiment, the present invention provides a novel method of treating a disease characterized by an inappropriate activation of peripheral CB1 receptors, comprising: administering to a patient in need thereof a therapeutically effective amount of a compound of the present invention or a pharmaceutically acceptable salt form thereof.

In another embodiment, the present invention provides a novel method for treating a disease mediated by the $CB_1$ receptor in a patient, comprising: administering to a patient in need thereof a therapeutically effective amount of a compound of the present invention or a pharmaceutically acceptable salt form thereof. In an example, the disease is mediated by peripheral $CB_1$ receptors. In another example, the $CB_1$ receptors that are blocked are peripheral $CB_1$ receptors.

In another embodiment, the present invention provides a novel method for treating a disease, comprising: administering to a patient in need thereof a therapeutically effective amount of a compound of the present invention or a pharmaceutically acceptable salt form thereof, wherein the disease is selected from obesity, diabetes, dyslipidemias, cardiovascular disorders, inflammatory disorders, hepatic disorders, cancers, and a combination thereof.

In another embodiment, the diabetes disorder is selected from Type 1 diabetes, Type 2 diabetes, inadequate glucose tolerance, and insulin resistance.

In another embodiment, the dyslipidemia disorder is selected from undesirable blood lipid levels, including low levels of high-density lipoprotein, high levels of low-density lipoprotein, high levels of triglycerides, and a combination thereof.

In another embodiment, the cardiovascular disorder is selected from atherosclerosis, hypertension, stroke and heart attack.

In another embodiment, the inflammatory disorder is selected from osteoarthritis, rheumatoid arthritis, inflammatory bowel diseases, and obesity-associated inflammation.

In another embodiment, the hepatic disorder is selected from liver inflammation, liver fibrosis, NASH, fatty liver, enlarged liver, alcoholic liver disease, jaundice, cirrhosis, and hepatitis.

In another embodiment, the cancer is selected from colon, breast, thyroid, and alveolar rhabdomyosarcoma.

In another embodiment, the present invention provides a novel method for treating a co-morbidity of obesity, comprising: administering to a patient in need thereof a therapeutically effective amount of a compound of the present invention or a pharmaceutically acceptable salt form thereof.

In another embodiment, the co-morbidity is selected from diabetes, dyslipidemias, Metabolic Syndrome, dementia, cardiovascular disease, and hepatic disease.

In another embodiment, the co-morbidity is selected from hypertension; gallbladder disease; gastrointestinal disorders; menstrual irregularities; degenerative arthritis; venous statis ulcers; pulmonary hypoventilation syndrome; sleep apnea; snoring; coronary artery disease; arterial sclerotic disease; pseudotumor cerebri; accident proneness; increased risks with surgeries; osteoarthritis; high cholesterol; and, increased incidence of malignancies of the ovaries, cervix, uterus, breasts, prostrate, and gallbladder.

In another embodiment, the present invention also provides a method of preventing or reversing the deposition of adipose tissue in a mammal by the administration of a compound of the present invention. By preventing or reversing the deposition of adipose tissue, compound of the present invention are expected to reduce the incidence or severity of obesity, thereby reducing the incidence or severity of associated co-morbidities.

In another embodiment, the present invention provides a compound of the present invention for use in therapy.

In another embodiment, the present invention provides the use of the present invention for the manufacture of a medicament for the treatment of an indication recited herein (e.g., obesity, diabetes, dyslipidemias, cardiovascular disorders, inflammatory disorders, hepatic disorders, cancers, and a combination thereof).

The present invention may be embodied in other specific forms without departing from the spirit or essential attributes thereof. This invention encompasses all combinations of aspects of the invention noted herein. It is understood that any and all embodiments of the present invention may be taken in conjunction with any other embodiment or embodiments to describe additional embodiments. It is also to be understood that each individual element of the embodiments is intended to be taken individually as its own independent embodiment. Furthermore, any element of an embodiment is meant to be combined with any and all other elements from any embodiment to describe an additional embodiment.

Definitions

The examples provided in the definitions present in this application are non-inclusive unless otherwise stated. They include but are not limited to the recited examples.

The compounds herein described may have asymmetric centers, geometric centers (e.g., double bond), or both. All chiral, diastereomeric, racemic forms and all geometric isomeric forms of a structure are intended, unless the specific stereochemistry or isomeric form is specifically indicated. Compounds of the present invention containing an asymmetrically substituted atom may be isolated in optically active or racemic forms. It is well known in the art how to prepare optically active forms, such as by resolution of racemic forms, by synthesis from optically active starting materials, or through use of chiral auxiliaries. Geometric isomers of olefins, C═N double bonds, or other types of double bonds may be present in the compounds described herein, and all such stable isomers are included in the present invention. Specifically, cis and trans geometric isomers of the compounds of the present invention may also exist and may be isolated as a mixture of isomers or as separated isomeric forms. All processes used to prepare compounds of the present invention and intermediates made therein are considered to be part of the present invention. All tautomers of shown or described compounds are also considered to be part of the present invention.

The present invention includes all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

Examples of the molecular weight of the compounds of the present invention include (a) less than about 500, 550, 600, 650, 700, 750, 800, 850, 900, 950, or 1000 grams per mole; (b) less than about 950 grams per mole; (c) less than about 850 grams per mole; and, (d) less than about 750 grams per mole.

"Alkyl" includes both branched and straight-chain saturated aliphatic hydrocarbon groups having the specified number of carbon atoms. $C_{1-6}$ alkyl, for example, includes $C_1$, $C_2$, $C_3$, $C_4$, $C_5$, and $C_6$ alkyl groups. Examples of alkyl include methyl, ethyl, n-propyl, i-propyl, n-butyl, s-butyl, t-butyl, n-pentyl, and s-pentyl.

"Alkenyl" includes the specified number of hydrocarbon atoms in either straight or branched configuration with one or more unsaturated carbon-carbon bonds that may occur in any stable point along the chain, such as ethenyl and propenyl. $C_{2-6}$ alkenyl includes $C_2$, $C_3$, $C_4$, $C_5$, and $C_6$ alkenyl groups.

"Alkynyl" includes the specified number of hydrocarbon atoms in either straight or branched configuration with one or more triple carbon-carbon bonds that may occur in any stable point along the chain, such as ethynyl and propynyl. $C_{2-6}$ Alkynyl includes $C_2$, $C_3$, $C_4$, $C_5$, and $C_6$ alkynyl groups.

"Cycloalkyl" includes the specified number of hydrocarbon atoms in a saturated ring, such as cyclopropyl, cyclobutyl, cyclopentyl, cyclohexyl, cycloheptyl, and cyclooctyl. $C_{3-8}$ cycloalkyl includes $C_3$, $C_4$, $C_5$, $C_6$, $C_7$, and $C_8$ cycloalkyl groups.

"Cyclic amine" is a hydrocarbon ring wherein one carbon atom of the ring has been replaced by a nitrogen atom. The cyclic amine can be unsaturated, partially saturated, or fully saturated. The cyclic amine can also be bicyclic, tricyclic, and polycyclic. Examples of cyclic amine include pyrrolidine and piperidine.

Halo" or "halogen" refers to fluoro, chloro, bromo, and iodo.

"Counterion" is used to represent a small, negatively charged species, such as chloride, bromide, hydroxide, acetate, and sulfate.

The group "$C_6H_4$" represents a phenylene.

"Aryl" refers to any stable 6, 7, 8, 9, 10, 11, 12, or 13 membered monocyclic, bicyclic, or tricyclic ring, wherein at least one ring, if more than one is present, is aromatic. Examples of aryl include fluorenyl, phenyl, naphthyl, indanyl, adamantyl, and tetrahydronaphthyl.

"Heteroaryl" refers to any stable 5, 6, 7, 8, 9, 10, 11, or 12 membered monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable.

Examples of heteroaryl includes acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, pyranyl, pyrazinyl, pyrazolyl, pyridazinyl, pyridooxazole, pyridoimidazole, pyridothiazole, pyridinyl, pyridyl, pyrimidinyl, 2H-pyrrolyl, pyrrolyl, quinazolinyl, quinolinyl, 4H-quinolizinyl, quinoxalinyl, quinuclidinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

"Mammal" and "patient" cover warm blooded mammals that are typically under medical care (e.g., humans and domesticated animals). Examples include feline, canine, equine, bovine, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are useful. Lists of suitable salts are found in *Remington's Pharmaceutical Sciences*, 18th ed., Mack Publishing Company, Easton, Pa., 1990, p 1445, the disclosure of which is hereby incorporated by reference.

"Therapeutically effective amount" includes an amount of a compound of the present invention that is effective when administered alone or in combination to treat obesity, diabetes, dyslipidemias, cardiovascular disorders, inflammatory disorders, hepatic disorders, cancers, and a combination or comorbitity thereof, or another indication listed herein. "Therapeutically effective amount" also includes an amount of the combination of compounds claimed that is effective to treat the desired indication. The combination of compounds can be a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased effect, or some other beneficial effect of the combination compared with the individual components.

Obesity is defined as having a body mass index (BMI) of 30 or above. The index is a measure of an individual's body weight relative to height. BMI is calculated by dividing body weight (in kilograms) by height (in meters) squared. Normal and healthy body weight is defined as having a BMI between 20 and 24.9. Overweight is defined as having a BMI≧25. Obesity has reached epidemic proportions in the U.S., with 44 million obese Americans, and an additional eighty million deemed medically overweight.

Obesity is a disease characterized as a condition resulting from the excess accumulation of adipose tissue, especially adipose tissue localized in the abdominal area. It is desirable to treat overweight or obese patients by reducing their amount of adipose tissue, and thereby reducing their overall body weight to within the normal range for their sex and height. In this way, their risk for co-morbidities such as diabetes, dyllipidemias, cardiovascular disorders, inflammatory disorders, hepatic disorders, and cancers will be reduced. It is also desirable to prevent normal weight individuals from accumulating additional, excess adipose tissue, effectively maintaining their body weights at a BMI<25, and preventing the development of co-morbidities. It is also desirable to control obesity, effectively preventing overweight and obese individuals from accumulating additional, excess adipose tissue, reducing the risk of further exacerbating their co-morbidities.

Type 2 Diabetes or Diabetes mellitus type 2 or (formerly called non-insulin-dependent diabetes mellitus (NIDDM), or adult-onset diabetes) is a metabolic disorder that is primarily characterized by insulin resistance, relative insulin deficiency, and hyperglycemia. The World Health Organization definition of diabetes is for a single raised glucose reading with symptoms otherwise raised values on two occasions, of either fasting plasma glucose≧7.0 mmol/l (126 mg/dl) or with a Glucose tolerance test: two hours after the oral dose a plasma glucose≧11.1 mmol/l (200 mg/dl). Type 2 Diabetes is rapidly increasing in the developed world and there is some evidence that this pattern will be followed in much of the rest of the world in coming years. CDC has characterized the increase as an epidemic (Diabetes, Atlanta: Centres for Disease Control, Atlanta, Report no. 2007-05-24). In addition, whereas this disease used to be seen primarily in adults over age 40 (in contrast to Diabetes mellitus type 1), it is now increasingly seen in children and adolescents, an increase thought to be linked to rising rates of obesity in this age group.

Insulin resistance means that body cells do not respond appropriately when insulin is present. Unlike insulin-dependent diabetes mellitus (Type 1), the insulin resistance is generally "post-receptor", meaning it is a problem with the cells that respond to insulin rather than a problem with insulin production. Type 2 diabetes is presently of unknown etiology (i.e., origin). About 90-95% of all North American cases of diabetes are type 2, and about 20% of the population over the age of 65 has diabetes mellitus Type 2 (*Nature,* 2001, 414, 6865). Diabetes affects over 150 million people worldwide and this number is expected to double by 2025. About 55 percent of type 2 diabetics are obese-chronic obesity leads to increased insulin resistance that can develop into diabetes (*Morbidity and Mortality Weekly Report* 2008, 53, 1066). Type 2 diabetes is often associated with obesity, hypertension, elevated cholesterol (combined hyperlipidemia), and with the condition often termed Metabolic syndrome (it is also known as Syndrome X, Reavan's syndrome, or CHAOS). There are several drugs available for Type 2 diabetics, including metformin, thiazolidinediones, which increase tissue insulin sensitivity, α-glucosidase inhibitors which interfere with absorption of some glucose containing nutrients, and peptide analogs that must be injected.

Dyslipidemia is the presence of abnormal levels of lipids and/or lipoproteins in the blood. Lipids (fatty molecules) are transported in a protein capsule, and the density of the lipids and type of protein determines the fate of the particle and its influence on metabolism. Lipid and lipoprotein abnormalities are extremely common in the general population, and are regarded as a highly modifiable risk factor for cardiovascular disease due to the influence of cholesterol, one of the most clinically relevant lipid substances, on atherosclerosis. In addition, some forms may predispose to acute pancreatitis.

In western societies, most dyslipidemias are hyperlipidemias; that is, an elevation of lipids in the blood, often due to diet and lifestyle. The prolonged elevation of insulin levels can also lead to dyslipidemia. The most prevalent hyperlipidemias include: hypercholesterolemia, characterized by elevated cholesterol (usually LDL), hypertriglyceridemia, characterized by elevated triglycerides (TGs); hyperlipoproteinemia, characterized by elevated lipoproteins; hyperchylomicronemia, characterized by elevated chylomicrons; and combined hyperlipidemia, characterized by elevated LDL and triglycerides. Abnormal decreases in the levels of lipids and/or lipoproteins in the blood also can occur. These include hypocholesterolemia, characterized by lowered cholesterol (usually high density lipoprotein, or HDL); and abetalipoproteinemia, characterized by lowered beta lipoproteins.

Dyslipidemia contributes to the development of atherosclerosis. Causes may be primary (genetic) or secondary. Diagnosis is by measuring plasma levels of total cholesterol, TGs, and individual lipoproteins. Treatment is dietary changes, exercise, and lipid-lowering drugs. A linear relation probably exists between lipid levels and cardiovascular risk, so many people with "normal" cholesterol levels benefit from achieving still lower levels. Normal and abnormal lipid levels have been defined in the Third Report of the Expert Panel on Detection, Evaluation, and Treatment of High Blood Cholesterol in Adults. National Institutes of Health, National Heart, Lung, and Blood Institute, 2001.

The treatment of choice for dyslipidemias is lifestyle change, including diet and exercise. Drugs are the next step when lifestyle changes are not effective. Lipid lowering drugs include statins, nicotinic acid, bile acid sequestrants, fibrates, cholesterol absorption inhibitors, and combination treatments (e.g., niacin and a statin). These agents are not without adverse effects, including flushing and impaired glucose tolerance (nicotinic acid), bloating, nausea, cramping, and constipation (bile acid sequestrants). Bile acid sequestrants may also increase TGs, so their use is contraindicated in patients with hypertriglyceridemia. Fibrates potentiate muscle toxicity when used with statins, and may increase LDL in patients with high TGs.

There are many kinds of hepatic (i.e., liver) diseases. Viruses cause some of them, like hepatitis A, hepatitis B and hepatitis C. Others can be the result of drugs, poisons or drinking too much alcohol. If the liver forms scar tissue because of an illness, it's called cirrhosis. Jaundice, or yellowing of the skin, can be one sign of hepatic disease. Cancer can affect the liver. Hepatic diseases such as hemochromatosis can be inherited. Additional liver diseases include nonalcohol steatohepatitis (NASH), alcoholic liver disease, cholangiocarcinoma, hepatic encephalopathy, hepatic failure, liver abscess, liver tumors, liver coagulopathy, glycogen storage diseases, portal hypertension, primary biliary cirrhosis, and primary sclerosing cholangitis.

There are few good treatment options for liver diseases. Options include lifestyle change (including diet and exercise), liver transplantation, and insertion of a transjugular intrahepatic portosystemic shunt that is placed in veins in the middle of the liver to improve blood flow to and from the organ. There are few effective drug treatment options for hepatic diseases. Interferon is an FDA-approved drug for the treatment of viral hepatitis. The chimeric protein Hyper-IL-6 dramatically enhances hepatocyte proliferation and is currently being evaluated as a pharmacological treatment for liver injury.

Drugs enter the CNS from the systemic circulation by crossing the blood-brain barrier (BBB). The BBB is a highly specialized 'gate-keeper' that protects the brain by preventing the entry of many potentially harmful substances into the CNS from the systemic circulation. Much is known about the BBB, and of the physical-chemical properties required for compounds transported across it.

Drugs that do not cross the BBB into the CNS or that are readily eliminated through transport mechanisms (*J. Clin. Invest.* 1996, 97, 2517) are known in the literature and have low CNS activity due to their inability to develop brain levels necessary for pharmacological action. The BBB has at least one mechanism to remove drugs prior to their accumulation in the CNS. P-Glycoproteins (P-gp) localized in plasma membrane of the BBB can influence the brain penetration and pharmacological activity of many drugs through translocation across membranes. The lack of accumulation into the brain by some drugs can be explained by their active removal from the brain by P-gp residing in the BBB. For example, the typical opioid drug loperamide, clinically used as an antidiarrheal, is actively removed from the brain by P-gp, thus explaining its lack of opiate-like CNS effects. Another example is domperidone, a dopamine receptor blocker that participates in the P-gp transport (*J. Clin. Invest.* 1996, 97, 2517). Whereas dopamine receptor blockers that cross the BBB can be used to treat schizophrenia, the readily-eliminated domperidone can be used to prevent emesis, without the likelihood of producing adverse CNS effects.

In addition to the above compounds, agents possessing structural characteristics that retard or prevent BBB penetration or contribute to participation in active elimination processes have been identified in various classes of therapeutics. These include antihistamines (*Drug Metab. Dispos.* 2003, 31, 312), beta-adrenergic receptor antagonists (*Eur. J. Clin. Pharmacol.* 1985, 28, Suppl: 21; *Br. J. Clin. Pharmacol.*, 1981, 11, 549), non-nucleoside reverse transcriptase inhibitors (NNRTIs, *J. Pharm. Sci.*, 1999, 88, 950), and opioid antagonists. This latter group has been tested in relation to their activity in the gastrointestinal tract. These peripherally selective opioid antagonists are described in various US patents as being useful in the treatment of non-CNS pathologies in mammals, in particular those of the gastrointestinal tract [see U.S. Pat. No. 5,260,542; U.S. Pat. No. 5,434,171; U.S. Pat. No. 5,159,081; and U.S. Pat. No. 5,270,238].

Other types of non-brain penetrant compounds can be prepared through the creation of a charge within the molecule. Thus, the addition of a methyl group to the tertiary amine functionality of the drugs scopolamine or atropine, unlike the parent molecules, prevents their passage across the BBB through the presence of a positive charge. However, the new molecules (methyl-scopolamine and methyl-atropine) retain their full anticholinergic pharmacological properties. As such, these drugs can also be used to treat peripheral diseases, without the concern of adverse CNS effects. The quaternary ammonium compound methylnaltrexone is also used for the prevention and/or treatment of opioid-induced gastrointestinal side effects associated with opioid administration (*J. Pharmacol. Exp. Ther.* 2002, 300, 118).

The discovery that the anti-obesity activity of cannabinoid receptor blockers may in part be mediated by a non-CNS mechanism could make it beneficial for the compounds of the present invention to be peripherally restricted (i.e., have an inability or limited ability to cross the BBB, or be readily eliminated from the brain through active transport systems). It may be desirable for the compounds of the present invention to be peripherally restricted, which in turn will result in no or very limited CNS effects. Compounds that provide peripherally mediated efficacy in treating obesity, diabetes, dyslipidemias, cardiovascular disorders, inflammatory disorders, hepatic disorders, cancers, a comorbitity thereof, or a combination or should result in therapeutic agents with greater safety. It can be desirable that the compounds of the present invention, when administered in a therapeutically effective amount, have no or very limited CNS effects. It can also be desirable that the lack of CNS effects is a result of the compounds of the present invention having minimal brain concentrations when administered in therapeutically effective amounts. In this context, minimal brain concentrations means levels that are too low to be therapeutically effective for the treatment of a CNS indication or too low to cause significant or measurable deleterious or undesired side effects, or both.

SLV319 (Compound AA) is a drug that crosses the BBB and is indicated for the treatment of obesity. It is believed that SLV319 works to treat obesity in part via a CNS mechanism. Compounds like SLV319 and related compounds have been described in various publications including *J. Med. Chem.* 2004, 47(3), 627 and U.S. Pat. No. 6,476,060.

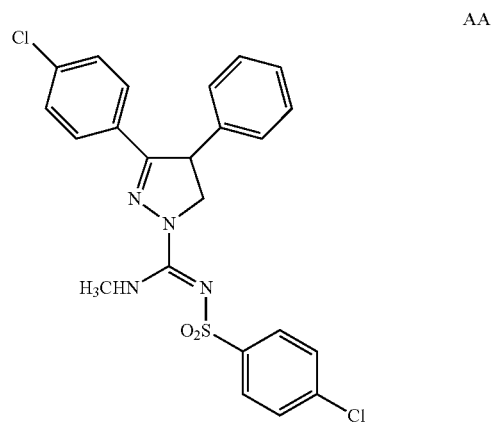

AA

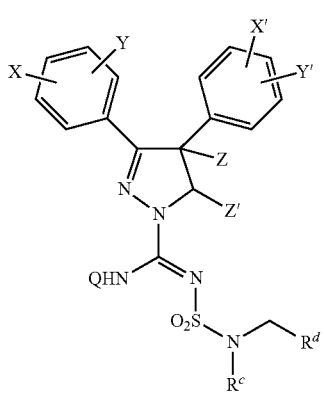

I

Des-phenyl analogs of AA are described in *Biorg. Med. Chem. Lett.* 2005, 15, 4793 and U.S. Pat. No. 6,974,810. In compound I, which is also a des-phenyl analog of AA, one of $R^d$, $R^e$, X, Y, X', Y', Z, Z', or Q is a group capable of reducing or limiting the CNS activity of compound I. This reduced or limited CNS activity occurs via at least one of $R^d$, $R^e$, X, Y, X', Y', Z, Z', and Q being a group that either limits compound I's ability to cross the BBB relative to that of SLV319 or enables it to be actively removed from the brain at a rate greater than that of SLV319. Examples of the amount of compound I present in the brain can include (a) from 50, 55, 60, 65, 70, 75, 80, 85, 90, 91, 92, 93, 94, 95, 96, 97, 98, 99, to 100% lower than SLV319, (b) from 90, 91, 92, 93, 94, 95, 96, 97, 98, 99, to 100% lower than SLV319, and (c) from 98, 99, to 100% lower than SLV319, when administered at the same dosage.

The compounds of the present invention have been shown to be active cannabinoid receptor blockers (e.g., have activity at $\leq 10$ μM). The compounds of the present invention are typically CB1 cannabinoid receptor blockers. However, CB1 blockers frequently are also CB2 blockers (i.e., CB2 antagonists or inverse agonists). Thus the present invention also includes CB2 blockers and compounds that are both CB1 and CB2 blockers.

An inverse agonist is a compound that not only blocks the action of the endogenous agonist at the receptor, but also exhibits its own activity which is usually the opposite of that shown by the agonist. Inverse agonists are also effective against certain types of receptors (e.g. certain histamine receptors/GABA receptors) that have intrinsic activity without the interaction of a ligand upon them (also referred to as 'constitutive activity').

Most methods of treating obesity are dependent on a significant reduction in energy intake, either by a decrease in food intake (e.g., sibutramine) or by inhibition of fat absorption (e.g., orlistat). In the present invention, adipose tissue may be reduced in the absence of a significant reduction in food intake. The weight loss, as a result of the present invention, comes from the treatment with a compound of the present invention, largely independent of, though not totally dissociated from, appetite and food intake. It can be desirable that adipose tissue loss occurs while food intake is maintained, increased or (a) about 1, 2, 3, 4, 5, 6, 7, 8, 9, 10, 11, 12, 13, 14, 15, 16, 17, 18, 19, or 20% below the normal range of the subject prior to being treated in accordance with the present invention (i.e., its pre-administration level), (b) about 1, 2, 3, 4, 5, 6, 7, 8, 9, 10, 11, 12, 13, 14, or 15% below its pre-administration level, (c) about 1, 2, 3, 4, 5, 6, 7, 8, 9, or 10% below its pre-administration level, or (d) about 1, 2, 3, 4, or 5% below its pre-administration level.

In some cases, loss of adipose tissue can be accompanied by a concomitant loss of lean muscle mass. This is particularly evident in cancer patients who show a generalized wasting of body tissues, including adipose tissue and lean muscle mass. In the present invention, however, it can be desirable for body fat to be significantly reduced in the absence of a significant reduction in lean body mass. Adipose tissue loss comes from treatment with a compound of the present invention, independent of a significant change in lean body mass. Thus, adipose tissue loss can occur while lean body mass is maintained, increased, or (a) is no more than about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% below the normal range of the subject prior to being treated in accordance with the present invention (i.e., its pre-administration level), (b) is no more than about 1, 2, 3, 4, 5, 6, 7, 8, 9, 10, 11, 12, 13, 14, or 15% below pre-administration levels, (c) is no more than about 1, 2, 3, 4, 5, 6, 7, 8, 9, or 10% below pre-administration levels, or (d) is no more than about 1, 2, 3, 4, or 5% below pre-administration levels.

In some cases, loss of adipose tissue can be accompanied by a concomitant loss of water mass. This is particularly evident with diet regimens that promote dehydration. In the present invention, it can be desirable for body fat to be significantly reduced in the absence of a significant reduction in water mass. In other words, adipose tissue loss comes from treatment with a compound of the present invention, independent of a significant change in water mass. It can be desirable that adipose tissue loss occurs while water mass is maintained, increased, or (a) is no more than about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% below the normal range of the subject prior to being treated in accordance with the present invention (i.e., its pre-administration level), (b) is no more than about 1, 2, 3, 4, 5, 6, 7, 8, 9, 10, 11, 12, 13, 14, or 15% below pre-administration levels, (c) is no more than about 1, 2, 3, 4, 5, 6, 7, 8, 9, or 10% below pre-administration levels, or (d) is no more than about 1, 2, 3, 4, or 5% below pre-administration levels.

Sibutramine and orlistat are currently marketed for use in the treatment of obesity, albeit weight loss is achieved through entirely different mechanism of action. Sibutramine inhibits the neuronal reuptake of serotonin and noradrenaline, and orlistat inhibits gut lipase enzymes that are responsible for breaking down ingested fat.

Cannabinoid receptor blockers can promote weight loss through inhibition of peripheral cannabinoid receptors, a mechanism entirely different from appetite suppressants, gut lipase inhibitors, and other agents with similar indications (e.g., serotonin agonists, leptin, fatty acid synthase inhibitors, and monoamine oxidase (MAO) inhibitors). Co-administration of a cannabinoid receptor blocker together with one or more other agents that are useful for treating the indications described above (e.g., obesity, diabetes, dyslipidemias, cardiovascular disorders, inflammatory disorders, hepatic disorders, cancers, and a combination thereof) is expected to be beneficial, by producing, for example, either additive or synergistic effects. Examples of additional agents include an appetite suppressant, a lipase inhibitor, and a MAO inhibitor (e.g., MAO-B and a combination of MAO-A/B). Therefore, the present invention provides a method of treating obesity, diabetes, dyslipidemias, cardiovascular disorders, inflammatory disorders, hepatic disorders, and/or cancers, and a combination thereof, comprising administering a therapeutically effective amount of a compound of the present invention and a second component effective for treating the desired indication.

Examples of second components include anti-obesity agents, which include, but are not limited to: 1) growth hormone secretagogues; 2) growth hormone secretagogue receptor agonists/antagonists; 3) melanocortin agonists; 4) Mc4r (melanocortin 4 receptor) agonists; 5) .beta.-3 agonists; 7) 5HT2C (serotonin receptor 2C) agonists; 8) orexin antagonists; 9) melanin concentrating hormone antagonists; 10) melanin-concentrating hormone 1 receptor (MCH1R) antagonists; 11) melanin-concentrating hormone 2 receptor (MCH2R) agonist/antagonists; 12) galanin antagonists; 13) CCK agonists; 14) CCK-A (cholecystokinin-A) agonists; 16) corticotropin-releasing hormone agonists; 17) NPY 5 antagonists; 18) NPY 1 antagonists; 19) histamine receptor-3 (H3) modulators; 20) histamine receptor-3 (H3) blockers; 21) β-hydroxy steroid dehydrogenase-1 inhibitors (.beta.-HSD-1); 22) PDE (phosphodiesterase) inhibitors; 23) phosphodiesterase-3B (PDE3B) inhibitors; 24) NE (norepinephrine) transport inhibitors; 25) non-selective serotonin/norepinephrine transport inhibitors, such as sibutramine, phentermine, or fenfluramine; 26) ghrelin antagonists; 28) leptin derivatives; 29) BRS3 (bombesin receptor subtype 3) agonists; 30) CNTF (Ciliary neurotrophic factors); 31) CNTF derivatives, such as axokine (Regeneron); 32) monoamine reuptake inhibitors; 33) UCP-1 (uncoupling protein-1), 2, or 3 activators; 34) thyroid hormone .beta. agonists; 35) FAS (fatty acid synthase) inhibitors; 37) DGAT2 (diacylglycerol acyltransferase 2) inhibitors; 38) ACC2 (acetyl-CoA carboxylase-2) inhibitors; 39) glucocorticoid antagonists; 40) acyl-estrogens; 41) lipase inhibitors, such as orlistat (Xenical®); 42) fatty acid transporter inhibitors; 43) dicarboxylate transporter inhibitors; 44) glucose transporter inhibitors; 45) phosphate transporter inhibitors; 46) serotonin reuptake inhibitors; 47) Metformin (Glucophage®); 48) Topiramate (Topimax®); 49) opiate antagonists such as naltrexone, 50) the non-selective transport inhibitor bupropion, and/or 51) MAO inhibitors.

Examples of MAO inhibitors include Moclobemide; Brofaromine; BW A616U; Ro 41-1049; RS-2232; SR 95191; Harmaline; Harman; Amiflamine; BW 1370U87; FLA 688; FLA 788; Bifemelane; Clorgyline; LY 51641; MDL 72,394; 544-Benzyloxyphenyl)-3-(2-cyanoethyl)-(3H)-1,3,4-oxadiazol-2-one; 5-(4-Arylmethoxyphenyl)-2-(2-cyanoethyl) tetrazoles; Lazabemide; Ro 16-6491; Almoxatone; XB308; RS-1636; RS-1653; NW-1015; SL 340026; L-selegiline; Rasagiline; Pargyline; AGN 1135; MDL 72,974; MDL 72,145; MDL 72,638; LY 54761; MD 780236; MD 240931; Bifemelane; Toloxatone; Cimoxatone; Iproniazid; Phenelzine; Nialamide; Phenylhydrazine; 1-Phenylcyclopropylamine; Isocarboxazid; and, Tranylcypromine. Additional examples of MAO inhibitors can be found in USPA 2007/0004683; U.S. Ser. No. 11/445,044; USPA 2007/0015734; and U.S. Ser. No. 11/424,274.

Examples of diabetes disorders include treating Type 1 diabetes, Type 2 diabetes, inadequate glucose tolerance, and insulin resistance.

Examples of second components useful for treating diabetes include (a) insulin sensitizers including (i) PPAR-γ agonists such as the glitazones (e.g. troglitazone, pioglitazone, englitazone, MCC-555, rosiglitazone), and compounds disclosed in WO97/27857, 97/28115, 97/28137, and 97/27847; and (ii) biguanides such as metformin and phenformin; (b) insulin or insulin mimetics; (c) sulfonylureas such as tolbutamide and glipizide, or related materials; (d) α-glucosidase inhibitors (e.g., acarbose); (e) cholesterol lowering agents such as (i) HMG-CoA reductase inhibitors (lovastatin, simvastatin, pravastatin, fluvastatin, atorvastatin, rivastatin, and other statins), (ii) sequestrants (e.g., cholestyramine, colestipol, and dialkylaminoalkyl derivatives of a cross-linked dextran), (iii) nicotinyl alcohol, nicotinic acid or a salt thereof, (iv) PPAR-α agonists (e.g., fenofibric acid derivatives including gemfibrozil, clofibrate, fenofibrate, and bezafibrate), (v) inhibitors of cholesterol absorption (e.g., β-sitosterol) and acyl CoA:cholesterol acyltransferase inhibitors (e.g., melinamide), and (vi) probucol; (f) PPAR-α/γ agonists; (g) antiobesity compounds (described previously); (h) ileal bile acid transporter inhibitors; (i) insulin receptor activators, (j) dipeptidyl peptidase IV, or DPP-4 inhibitors (sitagliptin, vildagliptin and other DPP-4 inhibitors (k) exenatide, (l) pramLintide, (m) FBPase inhibitors, (n) glucagon receptor antagonists, (o) glucagon-like peptide-1, and (p) the glucagon-like peptide-1 analogues (liraglutide, and others).

The compounds of the present invention are expected to be CB1 receptor blockers and are expected to be useful for treating diseases mediated by the $CB_1$ receptor. The compounds of the present are expected to possess an affinity in vitro for the central and/or peripheral cannabinoid receptors under the experimental conditions described by Devane et al., *Molecular Pharmacology,* 1988, 34, 605-613. The compounds according to the invention are also expected to possess an affinity for the cannabinoid receptors present on preparations of electrically stimulated isolated organs. These tests can be performed on guinea-pig ileum and on mouse vas deferens according to Roselt et al., *Acta Physiologica Scandinavia* 1975, 94, 142-144, and according to Nicolau et al., *Arch. Int. Pharmacodyn,* 1978, 236, 131-136.

CB1 receptor affinities can be determined using membrane preparations of Chinese hamster ovary (CHO) cells in which the human cannabinoid CB1 receptor is stably transfected (*Biochem J.* 1991, 279, 129-134) in conjunction with [3H] CP-55,940 as radioligand. After incubation of a freshly prepared cell membrane preparation with the [3H]-radioligand, with or without addition of test compound, separation of bound and free ligand is performed by filtration over glass fiber filters. Radioactivity on the filter is measured by liquid scintillation counting. The $IC_{50}$ values can be determined from at least three independent measurements.

Formulations and Dosages

In the present invention, the compound(s) of the present invention can be administered in any convenient manner (e.g., enterally or parenterally). Examples of methods of administration include orally and transdermally. One skilled in this art is aware that the routes of administering the compounds of the present invention may vary significantly. In addition to other oral administrations, sustained release compositions may be favored. Other acceptable routes may include injections (e.g., intravenous, intramuscular, subcutaneous, and intraperitoneal); subdermal implants; and, buccal, sublingual, topical, rectal, vaginal, and intranasal administrations. Bioerodible, non-bioerodible, biodegradable, and non-biodegradable systems of administration may also be used. Examples of oral formulations include tablets, coated tablets, hard and soft gelatin capsules, solutions, emulsions, and suspensions.

If a solid composition in the form of tablets is prepared, the main active ingredient can be mixed with a pharmaceutical vehicle, examples of which include silica, starch, lactose, magnesium stearate, and talc. The tablets can be coated with sucrose or another appropriate substance or they can be treated so as to have a sustained or delayed activity and so as to release a predetermined amount of active ingredient continuously. Gelatin capsules can be obtained by mixing the active ingredient with a diluent and incorporating the resulting mixture into soft or hard gelatin capsules. A syrup or elixir can contain the active ingredient in conjunction with a sweetener, which is typically calorie-free, an antiseptic (e.g., methylparaben and/or propylparaben), a flavoring, and an appropriate color. Water-dispersible powders or granules can contain the active ingredient mixed with dispersants or wetting agents or with suspending agents such as polyvinylpyrrolidone, as well as with sweeteners or taste correctors. Rectal administration can be effected using suppositories, which are prepared with binders melting at the rectal temperature (e.g., cocoa butter and/or polyethylene glycols). Parenteral administration can be effected using aqueous suspensions, isotonic saline solutions, or injectable sterile solutions, which contain pharmacologically compatible dispersants and/or wetting agents (e.g., propylene glycol and/or polyethylene glycol). The active ingredient can also be formulated as microcapsules or microspheres, optionally with one or more carriers or additives. The active ingredient can also be presented in the form of a complex with a cyclodextrin, for example α-, β-, or γ-cyclodextrin, 2-hydroxypropyl-β-cyclodextrin, and/or methyl-β-cyclodextrin.

The dose of the compound of the present invention administered daily will vary on an individual basis and to some extent may be determined by the severity of the disease being treated (e.g., obesity, diabetes, liver diseases, cardiometabolic disorders, and cancers). The dose of the compound of the present invention will also vary depending on the compound administered. Examples of dosages of compounds of the present invention include from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 15, 20, 25, 30, 35, 40, 45, 50, 55, 60, 65, 70, 76, 80, 85, 90, 95, to 100 mg/kg of mammal body weight. The compound can be administered in a single dose or in a number of smaller doses over a period of time. The length of time during which the compound is administered varies on an individual basis, and can continue until the desired results are achieved (i.e., reduction of body fat, or prevention of a gain in body fat). Therapy could, therefore, last from 1 day to weeks, months, or even years depending upon the subject being treated, the desired results, and how quickly the subject responds to treatment in accordance with the present invention.

A possible example of a tablet of the present invention is as follows.

| Ingredient | mg/Tablet |
| --- | --- |
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

A possible example of a capsule of the present invention is as follows.

| Ingredient | mg/Capsule |
| --- | --- |
| Active ingredient | 50 |
| Crystalline lactose | 60 |
| Microcrystalline cellulose | 34 |
| Talc | 5 |
| Magnesium stearate | 1 |
| Capsule fill weight | 150 |

In the above capsule, the active ingredient has a suitable particle size. The crystalline lactose and the microcrystalline cellulose are homogeneously mixed with one another, sieved, and thereafter the talc and magnesium stearate are admixed. The final mixture is filled into hard gelatin capsules of suitable size.

A possible example of an injection solution of the present invention is as follows.

| Ingredient | mg/Solution |
| --- | --- |
| Active substance | 1.0 mg |
| 1N HCl | 20.0 µl |
| acetic acid | 0.5 mg |
| NaCl | 8.0 mg |
| Phenol | 10.0 mg |
| 1N NaOH | q.s. ad pH 5 |
| $H_2O$ | q.s. ad 1 mL |

Synthesis

The compounds of the present invention can be prepared in a number of ways known to one skilled in the art of organic synthesis (e.g., see U.S. Pat. No. 6,476,060 B2, *Biorg Med Chem Lett,* 2005, 15, 4793 and U.S. Pat. No. 6,974,810). The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

Scheme 1

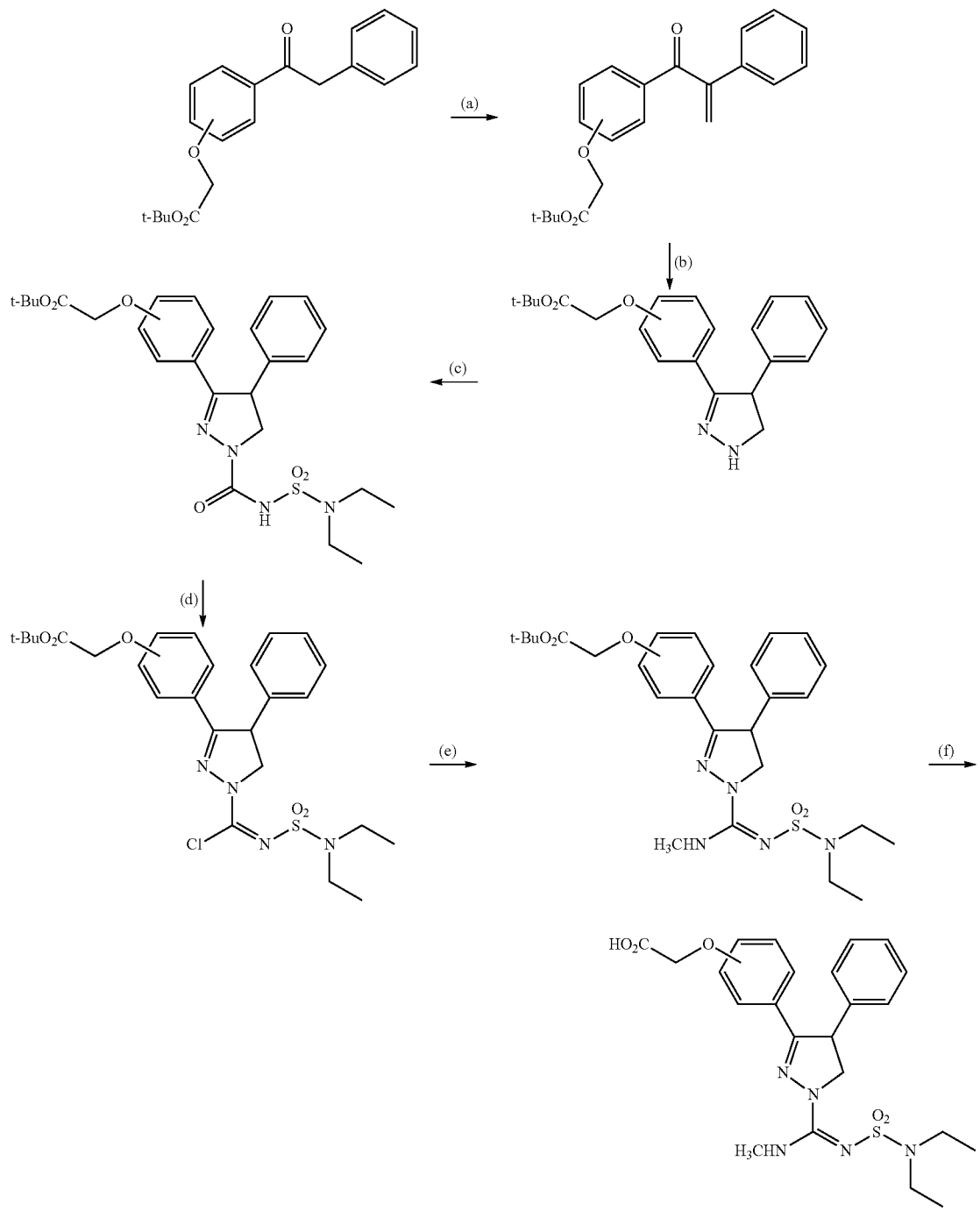

Scheme 1 shows how to convert 2'-, 3'-, or 4'-(carbo-t-butoxymethoxy)-2-phenylacetophenones, prepared from commercially available 2'-, 3'-, or 4'-methoxy-2-phenylacetophenones via O-demethylation using HBr/HOAc or BBr₃/CH₂Cl₂ and alkylation of the resultant phenol with t-butyl bromoacetate in the presence of base, in 37% aqueous formaldehyde containing piperidine under reflux to the corresponding acrylophenones (step a). Treatment of the acrylophenones with hydrazine hydrate in ethanol can produce the 3,4-diarylpyrazolines (step b). The diarylpyrazolines can be further treated with chlorosulfonylisocynanate in a solvent such as methylene chloride at about 0° C. to ambient temperature followed by an amine such as diethylamine to yield the diethylaminosulfonamide (step c). Conversion of these carbonyl compounds to the imidoyl chlorides could be carried out using phosphorus pentachloride in chlorobenzene at elevated temperatures (step d). Further exposure of these imidoyl chlorides to methylamine in methylene chloride at room temperature should afford the pyrazoline-1-carboxamidines (step e). Hydrolysis of the ester using TFA/CH₂Cl₂ should produce the carboxylic acid (step f).

Scheme 2

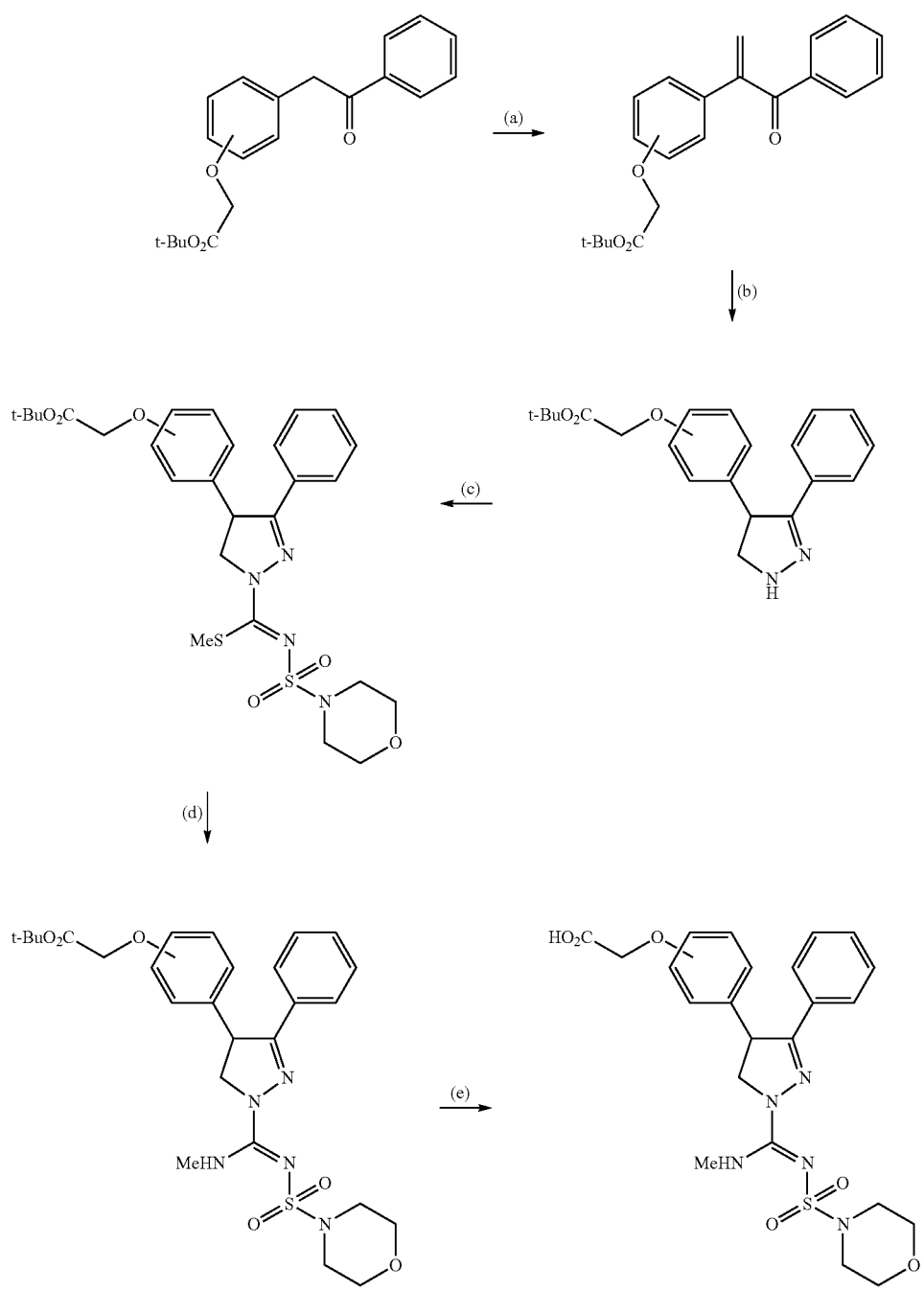

Scheme 2 describes how 2-(2'-, 3'- or 4'-carbo-t-butoxymethoxyphenyl)acetophenones (prepared similarly to scheme 1) should provide the corresponding acrylophenones by treatment with formalin as previously described (step a). Treatment of the acrylophenones with hydrazine hydrate in ethanol can produce the 3,4-diarylpyrazolines (step b). The diarylpyrazolines can be further treated with morpholinosulfonyldithioimidocarbonic acid methyl ester (prepared from the morpholino-N-sulfonamide and carbon disulfide/methyl iodide (as described in Biorg Med Chem Lett 2005, 15, 4794; J. Med. Chem., 47, 627 (2004); Chem. Ber. 1966, 99, 2885) in a solvent like pyridine at elevated temperature to yield pyrazole-1-carboximidothioic acid methyl esters (step c). Further exposure of these iminothioethers to an aqueous solution of methylamine in methanol at room temperature should afford the pyrazoline-1-carboxamidines (step d). Hydrolysis of the ester using TFA/CH$_2$Cl$_2$ should produce the carboxylic acid (step e).

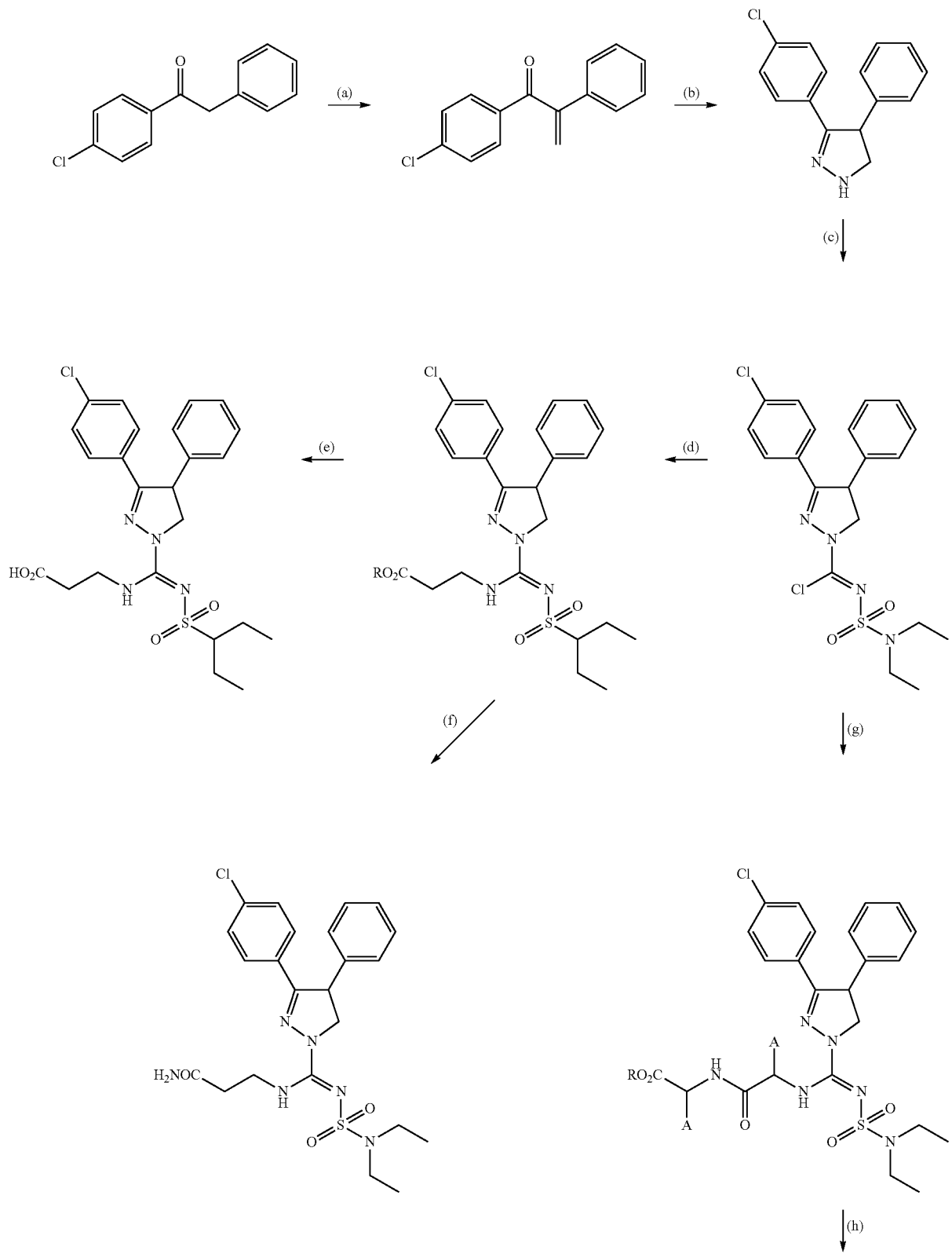
Scheme 3

-continued

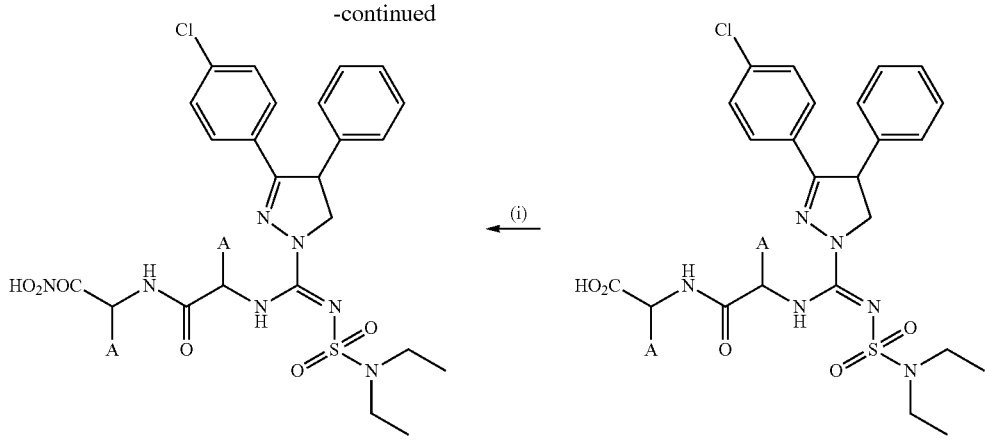

(i)

Scheme 3 shows the conversion of 4'-chloro-2-phenylacetophenone in 37% aqueous formalin and MeOH containing piperidine and acetic acid at reflux that should occur affording the acrylophenone (*J. Agric. Food Chem.* 1979, 27(2), 406) (step a). Treatment of the acrylophenone with hydrazine hydrate in ethanol can produce the 3,4-diarylpyrazolines (step b). The diarylpyrazoline can be further treated with chlorosulfonylisocynanate followed by diethyl amine to give the sulfonamide and chlorinated with phosphorus pentachloride, as previously described, to yield the imidoyl chloride (step c). Further exposure of these imidoyl chlorides to beta-alanine ethyl ester in ethanol or methylene chloride should yield the pyrazoline-esters (step d). Hydrolysis of the ester using lithium hydroxide in aqueous THF solution should produce the carboxylic acid (step e). Treatment of the ester with anhydrous ammonia in methanol at about 0° C. to room temperature can afford the carboxamido compound (step f). Alternatively, the iminothioethers can be coupled with di-amino acid esters to give adducts (step g) that can be hydrolyzed to carboxylic acids (step h). These acids may be converted to the carboxamides using oxalyl chloride in dichloroethane followed by anhydrous ammonia, or Boc$_2$O in pyridine/THF followed by anhydrous ammonia (step i).

Scheme 4

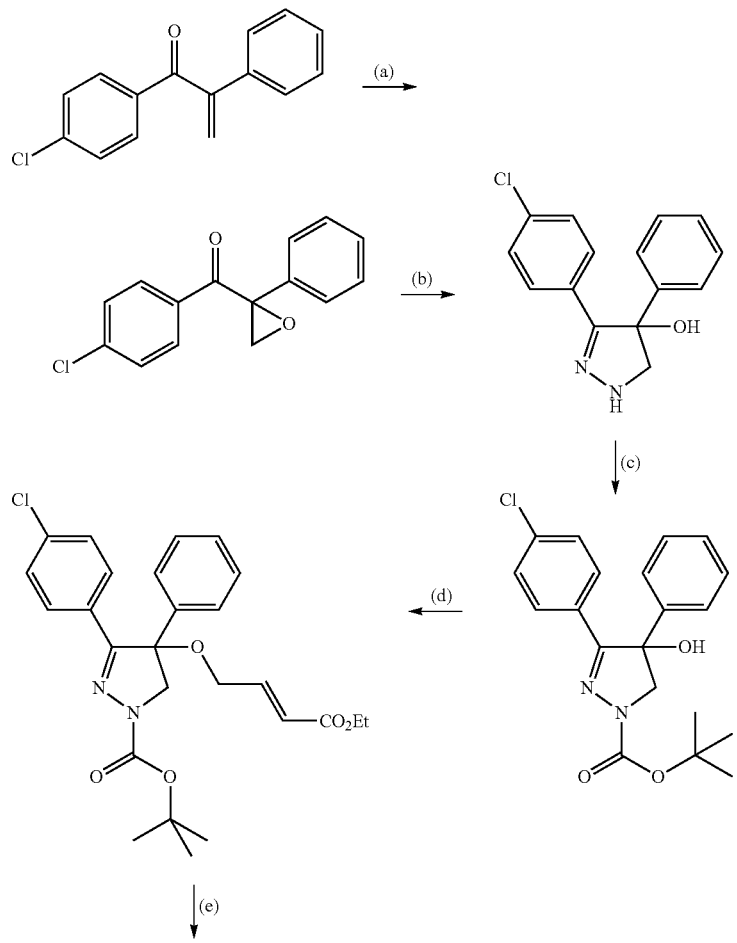

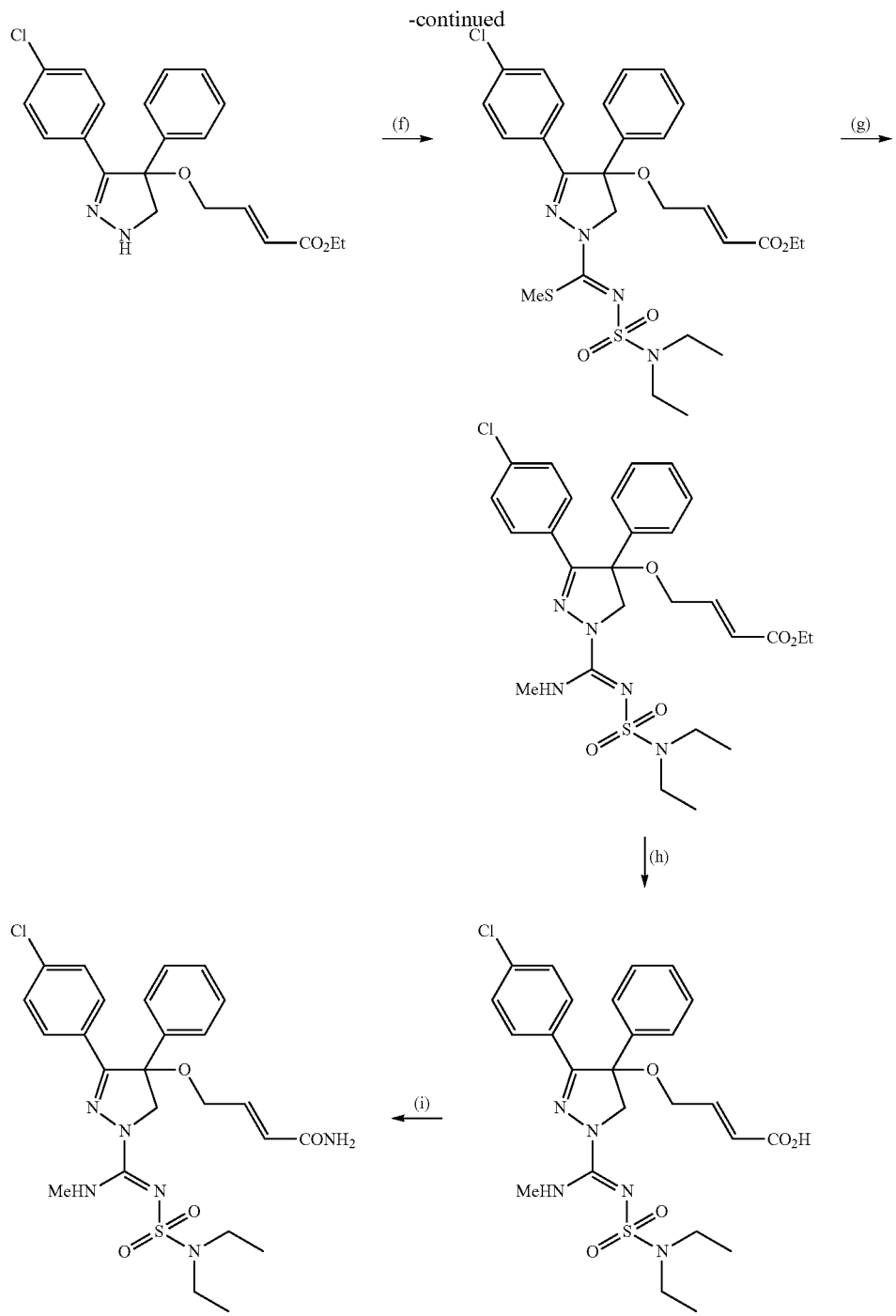

Scheme 4 illustrates how oxidation of 4'-chloro-2-phenylacrylophenone in methylene chloride with m-chloroperbenzoic acid should provide the epoxide (step a), which upon treatment with hydrazine hydrate in ethanol solution at about 35-40° C. can give the 3,4-diarylpyrazoline alcohol (step b). The pyrazoline can be protected using di-t-butyl-dicarbonate (t-Boc anhydride) in the presence of a base to give the N-t-BOC-pyrazoline (step c). The carbamate alcohol can then be deprotonated with sodium hydride in a solvent like DMF, or lithium hexamethylsilazide in THF, followed by alkylation with ethyl 4-bromocrotonate to yield the ester (step d). Removal of the t-BOC group can be achieved via treatment with TFA (step e). The pyrazoline can then be reacted with dialkylaminosulfonyldithioimidocarbonic acid methyl esters in a solvent like acetonitrile in the presence of triethylamine at reflux to yield the pyrazole-1-carboximidothioic acid methyl ether (step f). Further exposure of these iminothioethers to a solution of methylamine at 0 degrees to room temperature can afford the pyrazoline-1-carboxamidines (step g), and hydrolysis of the ester using LiOH in aqueous THF solution can produce the carboxylic acid (step h). The carbxoamides can be prepared by treatment of the acid with isobutylchloroformate (IBCF) in the presence of N-methylmorpholine (NMM) in dichloromethane and anhydrous ammonia (step i).

Scheme 5

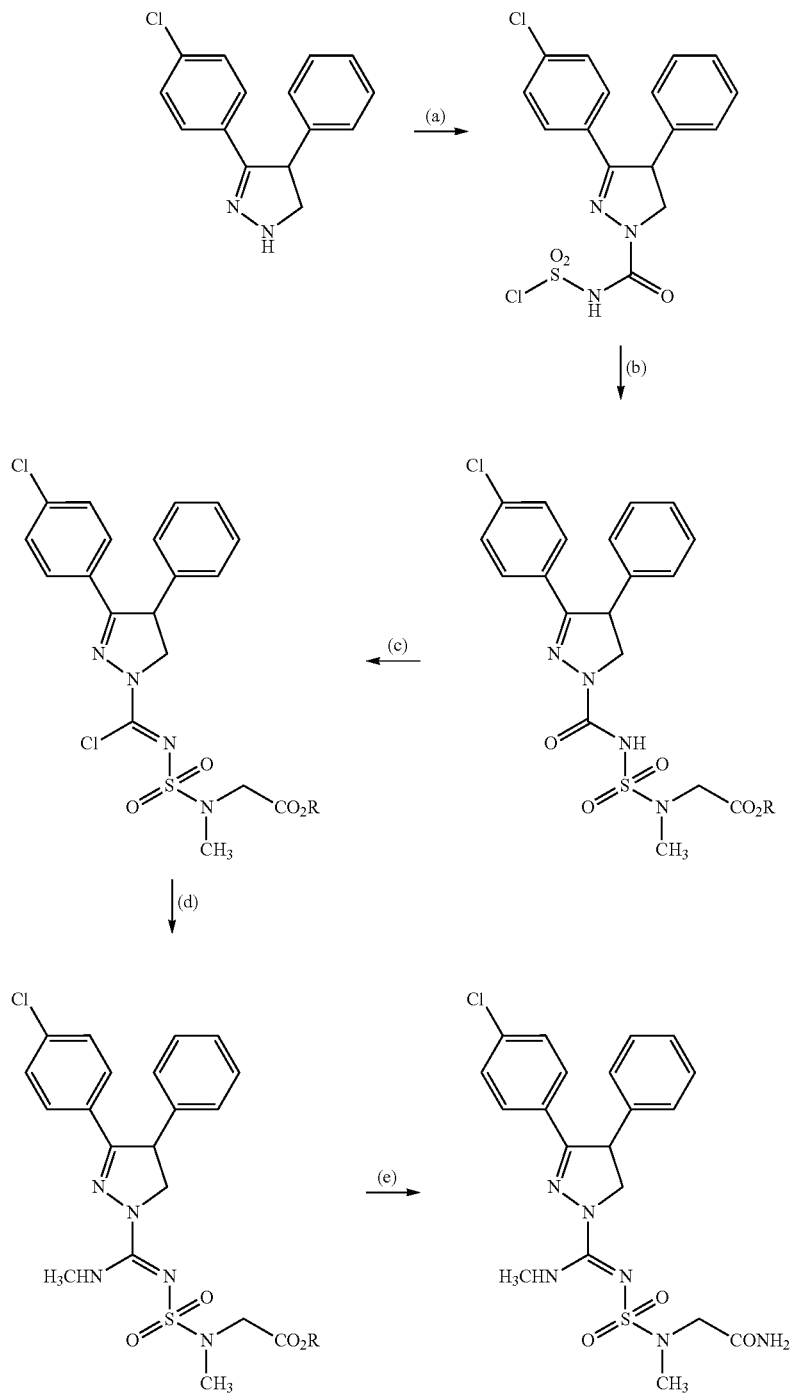

Scheme 5 shows how treatment of a solution of the 3,4-diarylpyrazoline and chlorosulfonylisocyanate in dichloromethane at 0° C. to ambient temperature can form the chlorosulfonamide adduct (step a). Treatment of this sulfonyl chloride with an amino acid ester such as ethyl sarcosine in dichloromethane in the presence of triethylamine can give the sulfonamide ester adduct (step b). Conversion of this intermediate to the imidoyl chloride can be accomplished using phosphorus pentachloride in chlorobenzene at elevated temperature (step c), followed by treatment with methyl amine in MeOH at about 0° C. to room temperature can afford the N-methylamine adduct (step d). The carboxamide may be prepared by further conversion of the ester to the acid, and subsequent treatment with IBCF, NMM and ammonia as previously described (step e).

Scheme 6
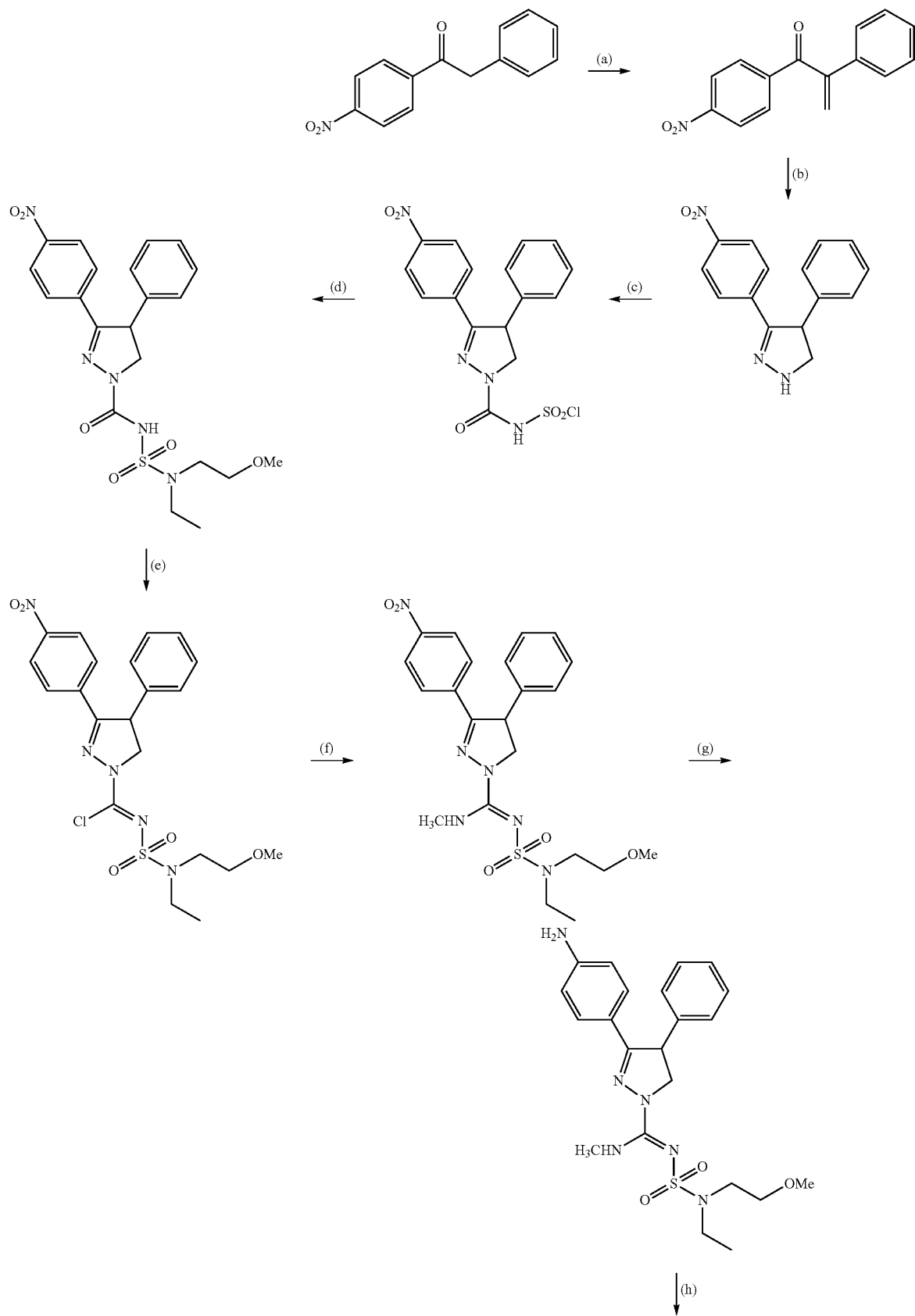

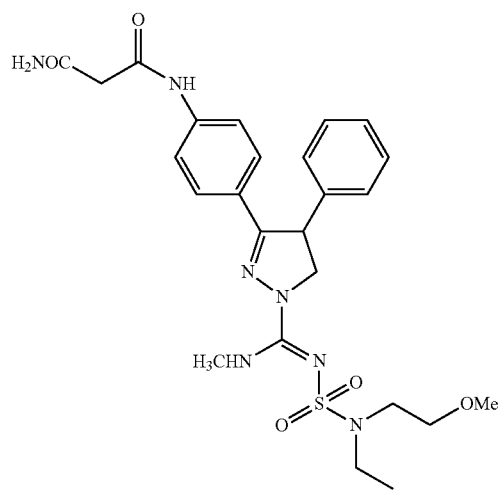
47

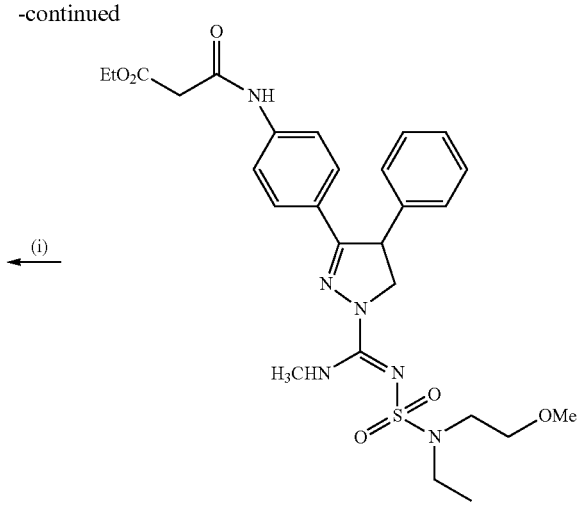
48

-continued

Scheme 6 depicts how condensation of a solution of 4'-nitro-2-phenylacetophenone in 37% aqueous formalin and MeOH containing piperidine and acetic acid should afford after heating at reflux, the corresponding acrylophenone (step a). Treatment of the acrylophenone with hydrazine hydrate in ethanol can produce the 3,4-diarylpyrazoline (step b). The pyrazoline can then be reacted with chlorosulfonylisocyanate in a solvent like dichloromethane at 0° C. to ambient temperature to yield the corresponding sulfonyl chloride (step c). Condensation of this intermediate with (methoxyethyl)ethylamine will afford the sulfonamide adduct (step d). Treatment of this intermediate with phosphorus pentachloride in chlorobenzene at elevated temperature should produce the imidoyl chloride (step e), and subsequent treatment with methyl amine in methanol can provide the methyl amino adduct (step f). The nitro group can be reduced using sodium dithionite in aqueous basic solution or with Fe in hydrochloric acid solution, to produce the aniline compound (step g). Acylation of the aniline with ethyl malonyl chloride in the presence of base should produce the amide (step h). Treatment of the amidoester with anhydrous ammonia in a solvent such as methanol or at zero degrees to room temperature should afford the pyrazole-1-carboxamidines with the terminal carboxamido group (step i).

Scheme 7

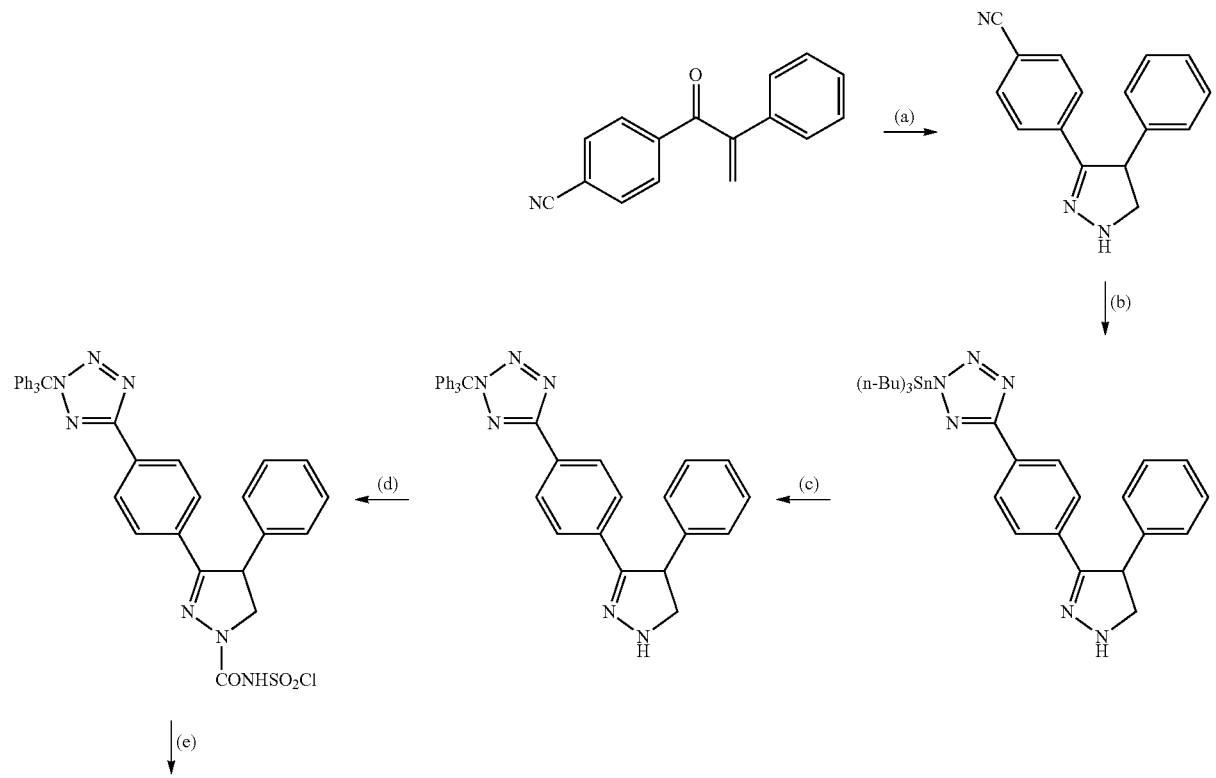

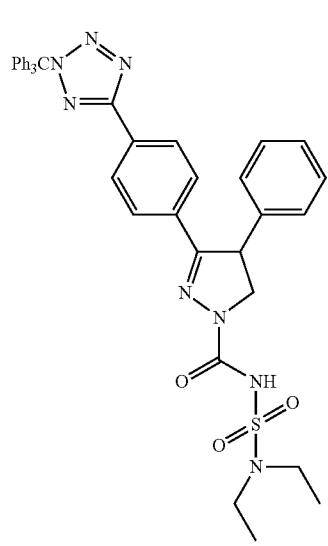
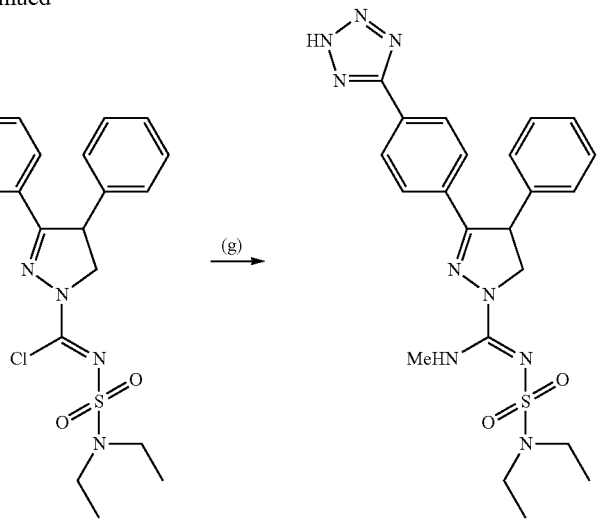

Scheme 7 illustrates how treatment of 4'-cyano-2-phenylacrylophenone with hydrazine hydrate in ethanol will produce the 3,4-diarylpyrazoline (step a). The pyrazoline can then be reacted with tri-n-butyltin azide, conveniently prepared in situ by the reaction of one equivalent of sodium azide and one equivalent of tri-n-butyltin chloride (*J. Med. Chem.* 1991, 56, 2395), in reluxing toluene or xylene to afford the tri-n-butyltin-tetrazole adduct (step b). The tri-n-butyltin-adduct can be converted to the trityl-tetrazole adduct by treatment with one equivalent of aqueous sodium hydroxide solution and one equivalent of trityl chloride at about ambient temperature or above (step c). Reaction of this adduct with chlorosulfonylisocyanate in a solvent like dichoromethane at 0° C. to ambient temperature should yield sulfonyl chloride (step d). Condensation of this intermediate with diethylamine will afford the sulfonamide adduct (step e). Treatment of this sulfonamide with phosphorus pentachloride in chlorobenzene at elevated temperature should produce the imidoyl chloride (step f). Subsequent treatment with methyl amine in methanol can provide the methyl amino adduct, and removal of the trityl group with aqueous TFA in THF at room temperature should yield the unprotected tetrazole (step g).

One stereoisomer of a compound of the present invention may be a more potent cannabinoid receptor antagonist than its counterpart(s). Thus, stereoisomers are included in the present invention. When required, separation of the racemic material can be achieved by HPLC using a chiral column or by a resolution using a resolving agent such as described in Wilen, S. H. *Tables of Resolving Agents and Optical Resolutions* 1972, 308 or using enantiomerically pure acids and bases. A chiral compound of the present invention may also be directly synthesized using a chiral catalyst or a chiral ligand, e.g., Jacobsen, E. *Acc. Chem. Res.* 2000, 33, 421-431 or using other enantio- and diastereo-selective reactions and reagents known to one skilled in the art of asymmetric synthesis. Examples of stereoisomers include compounds shown below.

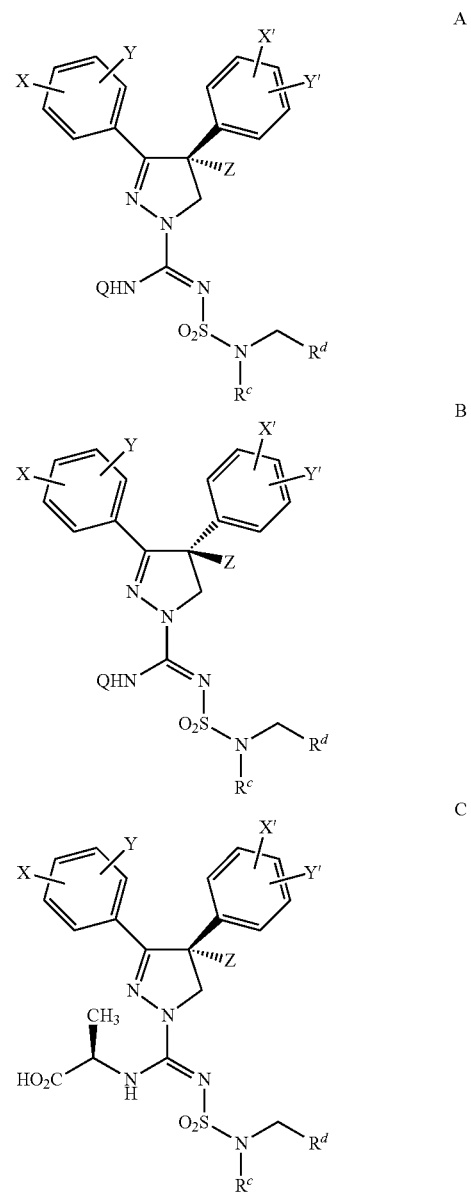

-continued

D
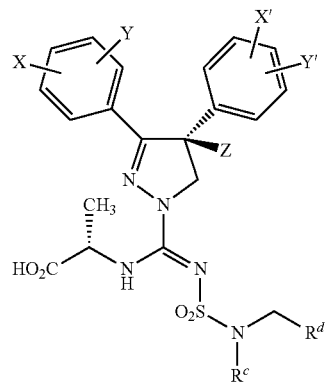

F
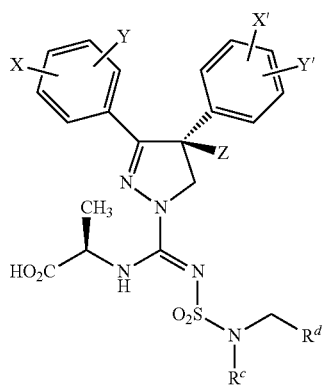

E
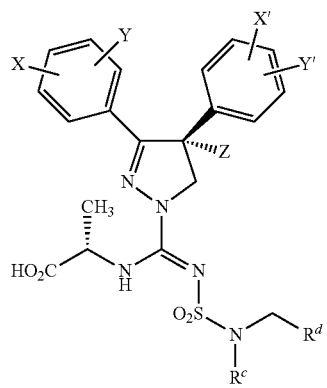

Other features of the invention will become apparent in the course of the following descriptions of exemplary embodiments that are given for illustration of the invention and are not intended to be limiting thereof.

EXAMPLES

Tables A-C list compounds of the present invention that have been made. Table A shows compounds of the invention synthesized by the route described in Scheme 3. Table B shows additional compounds of the invention synthesized by the route described in Scheme 3 or 5. The $CB_1$ $IC_{50}$ values for tested compounds are as follows.
+ 1000-10,000 nM
++ 100-1,000 nM
+++ <100 nM

TABLE A

| Ex. # | Q | $R^{c'}$ | $R^{d'}$ | CB1 $IC_{50}$ | NMR ppm |
|---|---|---|---|---|---|
| 1 | CHCH$_3$CONH$_2$ | H | H | +++ | (CDCl$_3$) |
|   |   |   |   |   | CH$_3$, 1.18, (6H, 2t) |
|   |   |   |   |   | CH$_3$, 1.61, (3H, 2d) |
|   |   |   |   |   | NCH$_2$, 3.22 (4H, 2q) |
|   |   |   |   |   | CH, 4.01, 4.10, (1H, 2dd) |
|   |   |   |   |   | CH, 4.49, 4.50 (1H, 2t) |
|   |   |   |   |   | CH, 4.62 (1H, m) |
|   |   |   |   |   | CH, 4.72, 4.81 (1H, 2t) |
|   |   |   |   |   | NH, 5.63, 5.80 (1H, 2 brd s) |
|   |   |   |   |   | NH, 6.70, 6.85 (1H, 2 brd s) |
|   |   |   |   |   | aromatic Hs, 7.14-7.52 (9H) |
| 2 | CH$_2$CONH$_2$ | H | H | ++ | (CDCl$_3$) |
|   |   |   |   |   | CH$_3$, 1.18, (3H, t) |
|   |   |   |   |   | NCH$_2$, 3.21 (4H, q) |
|   |   |   |   |   | CH, 4.03 (1H, dd) |

TABLE A-continued

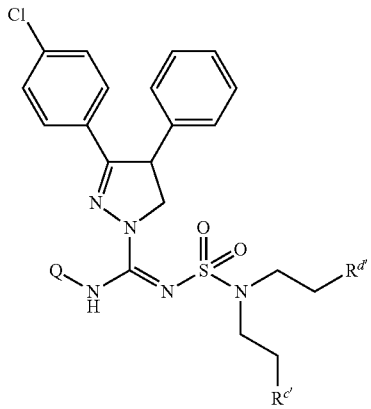

| Ex. # | Q | $R^{c'}$ | $R^{d'}$ | CB1 $IC_{50}$ | NMR ppm |
|---|---|---|---|---|---|
| | | | | | $CH_2$, 4.37 (2H, collapsed q) |
| | | | | | CH, 4.50 (1H, t) |
| | | | | | CH, 4.68 (1H, dd) |
| | | | | | NH, 5.66 (1H, brd s) |
| | | | | | NH, 6.52 (1H, brd s) |
| | | | | | aromatic Hs, 7.13-7.53 (9H) |
| | | | | | NH, 7.45 (1H, brd T) |
| 3 | $CHCH_3CONH_2$ | $OCH_3$ | $OCH_3$ | +++ | $(CDCl_3)$ |
| | | | | | $CH_3$, 1.63, (3H, 2d) |
| | | | | | $OCH_3$, 3.32 (6H, s) |
| | | | | | $NCH_2$, 3.48 (4H, m) |
| | | | | | $OCH_2$, 3.58 (4H, s) |
| | | | | | CH, 4.09, (1H, m) |
| | | | | | CH, 4.53 (1H, m) |
| | | | | | CH, 4.63 (1H, m) |
| | | | | | CH, 4.75, 4.91 (1H, 2m) |
| | | | | | NH, 5.44, 5.54 (1H, 2 brd s) |
| | | | | | NH, 6.90, 7.08 (1H, 2 brd s) |
| | | | | | aromatic Hs, 7.10-7.55 (9H) |
| 4 | $CH_2CO_2CH_3$ | H | $OCH_3$ | +++ | $(CDCl_3)$ |
| | | | | | $CH_3$, 1.19, (3H, t) |
| | | | | | $NCH_2$, 3.27 (4H, 2q) |
| | | | | | $OCH_3$, 3.33 (3H, s) |
| | | | | | $OCH_2$, 3.57 (2H, t) |
| | | | | | $OCH_3$, 3.79 (3H, s) |
| | | | | | CH, 4.11 (1H, m) |
| | | | | | $CH_2$, 4.41 (2H, d) |
| | | | | | CH, 4.55 (1H, brd t) |
| | | | | | CH, 4.65 (1H, dd) |
| | | | | | aromatic Hs, 7.13-7.52 (9H) |
| 5 | $CHCH_3CO_2CH_3$ | H | $OCH_3$ | +++ | $(CDCl_3)$ |
| | | | | | $CH_3$, 1.20, (3H, 2t) |
| | | | | | $CH_3$, 1.58, (3H, 2d) |
| | | | | | $NCH_2$, 3.27 (4H, m) |
| | | | | | $OCH_3$, 3.32, 3.34 (3H, 2s) |
| | | | | | $OCH_2$, 3.58 (2H, t) |
| | | | | | $OCH_3$, 3.75 (3H, s) |
| | | | | | CH, 4.13 (1H, dd) |
| | | | | | $CH_2$, 4.62 (2H, m) |
| | | | | | CH, 4.89 (1H, m) |
| | | | | | aromatic Hs, 7.12-7.52 (9H |
| 6 | $CH_2CONH_2$ | H | $OCH_3$ | +++ | $(CDCl_3)$ |
| | | | | | $CH_3$, 1.20, (3H, t) |
| | | | | | $NCH_2$, 3.27 (4H, 2q) |
| | | | | | $OCH_3$, 3.35 (3H, s) |
| | | | | | $OCH_2$, 3.57 (2H, t) |
| | | | | | CH, 4.07 (1H, dd) |
| | | | | | $CH_2$, 4.38 (2H, dq) |
| | | | | | CH, 4.50 (1H, t) |
| | | | | | CH, 4.65 (1H, dd) |
| | | | | | NH, 5.60 (1H, brd s) |
| | | | | | NH, 6.70 (1H, brd s) |
| | | | | | aromatic Hs, 7.12-7.54 (9H) |
| 7 | $CHCH_3CONH_2$ | H | $OCH_3$ | +++ | $(CDCl_3)$ |
| | | | | | $CH_3$, 1.20, (3H, t) |
| | | | | | $CH_3$, 1.62, (3H, 2d) |
| | | | | | $NCH_2$, 3.30 (4H, m) |

TABLE A-continued

[Structure: 3-(4-chlorophenyl)-4-phenyl-4,5-dihydro-1H-pyrazole linked at N1 to C(=NQ-NH-)-N=S(=O)(=O)-N(CH₂CH₂R^{d'})(CH₂CH₂R^{c'})]

| Ex. # | Q | R^{c'} | R^{d'} | CB1 IC₅₀ | NMR ppm |
|---|---|---|---|---|---|
| | | | | | OCH₃, 3.32, 3.33 (3H, 2s) |
| | | | | | OCH₂, 3.56 (2H, t) |
| | | | | | CH, 4.08, (1H, dq) |
| | | | | | CH, 4.52 (1H, t) |
| | | | | | CH, 4.64 (1H, dd) |
| | | | | | CH, 4.75, 4.92 (1H, 2 qnt) |
| | | | | | NH, 5.47, 5.57 (1H, 2 brd s) |
| | | | | | NH, 6.76, 6.96 (1H, 2 brd s) |
| | | | | | aromatic Hs, 7.12-7.56 (9H) |
| 8 | CH(CH(CH₃)₂)—CONH₂ | H | OCH₃ | +++ | (CDCl₃) |
| | | | | | CH₃, 1.11 (3H, m) |
| | | | | | CH₃, 1.18 (6H, m) |
| | | | | | CH, 2.45 (1H, brd m) |
| | | | | | NCH₂, 3.30 (4H, m) |
| | | | | | OCH₃, 3.31, 3.32 (3H, 2s) |
| | | | | | OCH₂, 3.56 (2H, 2t) |
| | | | | | CH, 4.08, (1H, brd m) |
| | | | | | CH, 4.50 (1H, brd t) |
| | | | | | CH, 4.64 (1H, dd) |
| | | | | | CH, 4.75, 4.60 (1H, 2m) |
| | | | | | NH, 5.60, 5.76 (1H, 2 brd s) |
| | | | | | NH, 6.75, 6.88 (1H, 2 brd s) |
| | | | | | aromatic Hs, 7.11-7.54 (9H) |
| 9 | CH(CHOHCH₃)—CONH₂ | H | OCH₃ | +++ | (CD₃OD) |
| | | | | | CH₃, 1.18 (3H, 2t) |
| | | | | | CH₃, 1.36 (3H, 2d) |
| | | | | | NCH₂, ~3.30 (4H, m) |
| | | | | | OCH₃, 3.30, 3.31 (3H, 2s) |
| | | | | | OCH₂, 3.55 (2H, 2t) |
| | | | | | CH, 4.10, (1H, brd m) |
| | | | | | CH, 4.39 (2H, m) |
| | | | | | CH, 4.51, 4.62 (1H, 2m) |
| | | | | | CH, ~4.9 (1H m) |
| | | | | | aromatic Hs, 7.21-7.71 (9H) |
| 10 | CH₂CH₂SO₂NH₂ | H | OCH₃ | +++ | (CDCl₃) |
| | | | | | CH₃, 1.18 (3H, t) |
| | | | | | NCH₂, 3.29 (4H, m) |
| | | | | | OCH₃, 3.35 (3H, s) |
| | | | | | OCH₂, 3.55 (2H, 2t) |
| | | | | | CH, 4.10, (1H, dd) |
| | | | | | CH₂, 4.21 (2H, m) |
| | | | | | CH, 4.54 (1H, t) |
| | | | | | CH, 4.70 (1H, dd) |
| | | | | | NH, 5.24 (2H, brd s) |
| | | | | | NH, 6.75, 6.88 (1H, 2 brd s) |
| | | | | | aromatic Hs, 7.11-7.54 (9H) |
| 11 | CH₂CHCH₃—CONH₂ | H | OCH₃ | ++ | (CDCl₃) |
| | | | | | CH₃, 1.19 (3H, 2t) |
| | | | | | CH₃, 1.26 (3H, 2d) |
| | | | | | CH, 2.85 (1H, brd m) |
| | | | | | NCH₂, 3.27 (4H, m) |
| | | | | | OCH₃, 3.33 (3H, s) |
| | | | | | OCH₂, 3.57 (2H, 2t) |
| | | | | | CH, 3.72, (1H, m) |
| | | | | | CH, 3.90, (1H, 2dd) |
| | | | | | CH, 4.53 (1H, 2t) |
| | | | | | CH, 4.65 (1H, 2dd) |

TABLE A-continued

| Ex. # | Q | $R^{c'}$ | $R^{d'}$ | CB1 IC$_{50}$ | NMR ppm |
|---|---|---|---|---|---|
| 12 | CH(CH(CH$_3$)$_2$)—CONH$_2$ | H | H | +++ | NH, 5.50 (1H, brd s)<br>NH, 6.15 (1H, brd s)<br>aromatic Hs, 7.16-7.54 (9H) (CDCl$_3$)<br>CH$_3$, 1.18, (6H, 2t)<br>CH$_3$, 1.20, (6H, 2d)<br>CH, 2.47, (1H, m)<br>NCH$_2$, 3.23 (4H, m)<br>CH, 3.98, 4.03, (1H, 2 brd s)<br>CH, 4.46 (1H, brd m)<br>CH, 4.62 (1H, m)<br>CH, 4.62, 4.80 (1H, 2 brd s)<br>NH, 5.63, 5.80 (1H, 2 brd s)<br>NH, 6.62, 6.80 (1H, 2 brd s)<br>aromatic Hs, 7.12-7.55 (9H) |
| 13 | CH(CHOHCH$_3$)—CONH$_2$ | H | H | +++ | (CD$_3$OD)<br>CH$_3$, 1.18, (6H, m)<br>CH$_3$, 1.35, (3H, m)<br>CH, 2.47, (1H, m)<br>NCH$_2$, 3.23 (4H, m)<br>CH, 3.97-4.20, (1H, 2 brd m)<br>CH, 4.40 (1H, brd s)<br>CH, 4.52 (1H, brd m)<br>CH, 4.52, 4.68 (1H, 2 brd m)<br>CH, ~4.85 (1H, m)<br>aromatic Hs, 7.32-7.70 (9H) |
| 14 | CH$_2$CH$_2$CONH$_2$ | H | OCH$_3$ | +++ | (CDCl$_3$)<br>CH$_3$, 1.19 (3H, 2t)<br>CH$_3$, 1.26 (3H, 2d)<br>CH, 2.85 (1H, brd m)<br>NCH$_2$, 3.27 (4H, m)<br>OCH$_3$, 3.33 (3H, s)<br>OCH$_2$, 3.57 (2H, 2t)<br>CH, 3.72, (1H, m)<br>CH, 3.90, (1H, 2dd)<br>CH, 4.53 (1H, 2t)<br>CH, 4.65 (1H, 2dd)<br>NH, 5.50 (1H, brd s)<br>NH, 6.15 (1H, brd s)<br>aromatic Hs, 7.16-7.54 (9H) |
| 15 | CH$_2$CH$_2$CH$_2$—SO$_2$NH$_2$ | H | H | +++ | (CDCl$_3$)<br>CH$_3$, 1.16 (3H, t)<br>CH$_2$, 2.29 (2H, m)<br>NCH$_2$, 3.20 (4H, q)<br>SO$_2$CH2, 3.33 (2H, t)<br>NCH$_2$, 3.86 (2H, m)<br>CH, 4.06, (1H, dd)<br>CH, 4.52 (1H, t)<br>CH, 4.66 (1H, dd)<br>NH, 5.06 (2H, s)<br>NH, 7.03 (1H, brd s)<br>aromatic Hs, 7.15-7.51 (9H) |
| 16 | CH$_2$CONHCH$_2$—CH$_2$SO$_2$NH$_2$ | H | H | +++ | (CDCl$_3$)<br>CH$_3$, 1.16 (3H, t)<br>NCH$_2$, 3.18 (4H, q)<br>SO$_2$CH$_2$, 3.30 (2H, brd s)<br>NCH$_2$, 3.79 (2H, brd s) |

TABLE A-continued

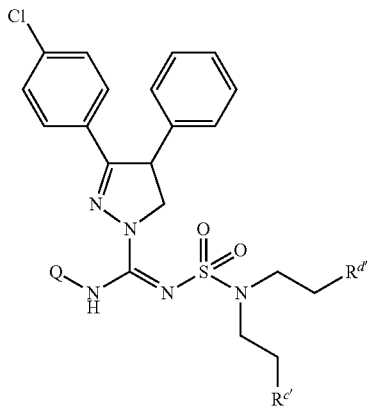

| Ex. # | Q | $R^{c'}$ | $R^{d'}$ | CB1 $IC_{50}$ | NMR ppm |
|---|---|---|---|---|---|
| 17 | $CH_2CHOHCH_2$—$CONH_2$ | H | H | | $NCH_2CO$, 4.30, (2H, brd s)<br>CH, 4.58 (1H, t)<br>CH, 4.71 (1H, dd)<br>NH, 5.51 (2H, s)<br>NH, 7.40 (1H, brd s)<br>aromatic Hs, 7.16-7.55 (9H)<br>($CD_3OD$) |
| 18 | $CH(C_6H_5)CONH_2$ | H | H | | $CH_3$, 1.16, (6H, t)<br>$CH_2CO$, 2.46, (2H, t)<br>$OCH_3/NCH_2$, 3.23-3.31 (5H, m)<br>$OCH_2$, 3.55 (2H, t)<br>CH, 3.58 (1H, d)<br>CH, 3.82 (1H, d)<br>CH, 4.12 (1H, brd s)<br>CH, 4.26 (1H, brd m)<br>CH, 4.54, (1H, t)<br>CH, ~4.9 (1H, m)<br>aromatic Hs, 7.24-7.72 (9H)<br>($CDCl_3$) |
| 19 | $CH_2CHOHCH_2$—$CH_2CONH_2$ | H | $OCH_3$ | | $CH_3$, 1.14 (6H, 2t)<br>$NCH_2$, 3.16 (4H, 2q)<br>CH, 3.80, 4.12 (1H, 2m)<br>CH, 4.48 (H, brd s)<br>CH, 4.50, 4.65 (1H, 2m)<br>CH, 5.70, 5.80 (1H, 2 brd s)<br>NH, 5.90, 6.10 (1H, 2 brd s)<br>NH, 6.57, 6.75 (1H, 2 brd s)<br>aromatic Hs, 7.13-7.57 (9H)<br>NH, 7.71 (~1H, brd s)<br>($CD_3OD$)<br>$CH_3$, 1.18, (6H, t)<br>$CH_2CO$, 2.47, (2H, d)<br>$NCH_2$, 3.20 (4H, q)<br>CH, 3.60 (1H, m)<br>CH, 3.83 (1H, m)<br>CH, 4.12 (1H, brd s)<br>CH, 4.27 (1H, brd m)<br>CH, 4.54, (1H, t)<br>CH, ~4.9 (1H, m)<br>aromatic Hs, 7.23-7.71 (9H) |

TABLE B

| Ex. # | Q | U | R$^e$ | CB$_1$ IC$_{50}$ | NMR ppm |
|---|---|---|---|---|---|
| 1. | CH$_3$ | CH$_2$ | CHCO$_2$Et | +++ | (CDCl$_3$) CH$_3$, 1.23, (3H, 2t); CH, 1.4-1.85, (3H); CH, 2.00, (1H, m); CH$_2$, 2.62, (4H, brd m); NCH$_3$, 3.25 (3H, 2d); CH, 3.6, 3.87 (1H, 2m); OCH$_2$, 4.11 (2H, m); CH, 4.64 (1H, 2 brd t); NH, 6.85 (1H, brd s); aromatic Hs, 7.15-7.55 (9H) |
| 2 | CH$_3$ | O | CHCO$_2$Et | ++ | (CDCl$_3$) CH$_3$, 1.27, (3H, 2t); CH$_2$, 2.87, (2H, m); NCH$_3$, 3.25 (3H, 2d); CH, 3.42 (1H, d); CH, ~3.77 (1H); CH, 3.79 (1H, 2t); CH$_2$, 4.11 (2H, m); CH$_2$, 4.23 (2H, 2q); CH$_2$, ~4.24 (1H, m); CH, 4.58 (1H, brd t); CH, 4.70 (1H, brd m); NH, 6.78 (1H, brd s); aromatic Hs, 7.14-7.54 (9H) |
| 3 | CH$_3$ | O | CHCONH$_2$ | + | (CDCl$_3$) CH, 2.57, (1H, t); CH, 2.77 (1H, m); NCH$_3$, 3.24 (3H, 2d); CH, 3.52 (1H, brd d); CH, 3.76 (1H, 2t); CH, 3.79 (1H, 2t); CH$_2$, 4.00 (2H, brd d); CH$_2$, ~4.24 (1H, m); CH, 4.60 (1H, m); CH, 4.69 (1H, m); NH, 5.63 (1H, brd d); NH, 6.50 (1H, brd s); NH, 6.85 (1H, brd s); aromatic Hs, 7.14-7.55 (9H) |
| 4 | CH$_3$ | CHCO$_2$Et | H | +++ | (CDCl$_3$) CH$_3$, 1.23, (3H, t); CH$_2$, 1.85, (2H, m); CH$_2$, 1.97, (2H, m); CH, 2.33, (1H, m); NCH, 2.70, (2H, brd t); NCH$_3$, 3.24 (3H, d); NCH$_2$, 3.62 (2H, 2t); CH, ~4.10 (1H); OCH$_2$, 4.11 (2H, q); CH, 4.57 (1H, 2t); CH, 4.65 (1H, dd); NH, 6.85 (1H, brd s); aromatic Hs, 7.15 ~7.55 (9H) |

TABLE B-continued

| Ex. # | Q | U | $R^e$ | $CB_1$ $IC_{50}$ | NMR ppm |
|---|---|---|---|---|---|
| 5 | $CH_3$ | $CHCONH_2$ | H | + | (CDCl$_3$) CH$_3$, 1.25, (3H, t) CH$_2$, 1.84, (2H, m) CH$_2$, 1.94, (2H, brd s) CH, 2.21, (1H, m) NCH, 2.65, (2H, brd s) NCH$_3$, 3.24 (3H, d) NCH$_2$, 3.74 (2H, brd d) CH, 4.13 (1H) CH, 4.57 (1H, 2t) CH, 4.65 (1H, brd dd) NH, 5.48, 5.56 (1H, 2 brd s) NH, 6.85 (1H, brd s) aromatic Hs, 7.15-7.54 (9H) |
| 6 | $CH_2CONH_2$ | O | H | +++ | (CDCl$_3$) NCH$_2$, 3.12, (4H, t) OCH$_2$, 3.76 (4H, t) CH, 4.11 (1H, dd) CH$_{2+1}$ $_C$O, 4.42 (2H, d) CH, 4.57 (1H, t) CH, 4.72 (1H, dd) NH, 5.78 (1H, brd s) NH, 6.35 (1H, brd s) aromatic Hs, 7.14-7.57 (9H) |
| 7 | $CHCH_3CO_2CH_3$ | O | H | +++ | (CDCl$_3$) CH$_3$, 1.58, (3H, 2d) NCH$_2$, 3.13, (4H, t) OCH, 3.77 (7H, m) CH, 4.24 (1H, brd s) CH 4.62 (1H, brd m) CH, 4.67 (1H, brd t) CH, 4.93 (1H, m) NH, 6.35 (1H, brd s) aromatic Hs, 7.13 ~7.53 (9H) |
| 8 | $CHCH_3CONH_2$ | O | H | +++ | (CDCl$_3$) CH$_3$, 1.62, (3H, 2d) NCH$_2$, 3.13, (4H, m) OCH$_2$, 3.77 (4H, m) CH, 4.10 (1H, brd s) CH 4.58 (1H, brd t) CH, 4.70 (1H, m) CH, 4.80 (1H, m) NH, 5.55 (1H, brd s) NH, 6.45 (1H, brd s) aromatic Hs, 7.13-7.54 (9H) |
| 9 | $CH(CHOH—(CH_3))CO_2CH_3$ | O | H | | (CDCl$_3$) CH$_3$, 1.41, (3H, 2d) NCH$_2$, 3.14, (4H, m) OCH$_2$, 3.77 (4H, m) OCH$_3$, 3.82, 3.83 (3H, 2s) CH 4.19 (1H, brd m) CH, 4.42 (1H, brd s) CH, 4.65 (1H, m) CH, 4.69 (1H, m) CH, 4.89 (1H, m) aromatic Hs, 7.14-7.54 (9H) NH, 7.60 (1H, brd s) |

TABLE B-continued

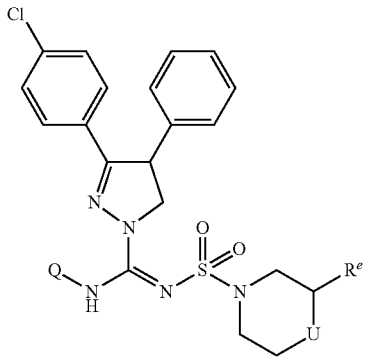

| Ex. # | Q | U | R$^e$ | CB$_1$ IC$_{50}$ | NMR ppm |
|---|---|---|---|---|---|
| 10 | CHCH(CH$_3$)$_2$CO$_2$CH$_3$ | O | H | | (CDCl$_3$) |
| | | | | | CH$_3$, 1.10 (6H, m) |
| | | | | | CH, 2.35 (1H, m) |
| | | | | | NCH$_2$, 3.14, (4H, m) |
| | | | | | OCH$_2$, 3.77 (4H, m) |
| | | | | | OCH$_3$, 3.78, 3.79 (3H, 2s) |
| | | | | | CH 4.18 (1H, brd m) |
| | | | | | CH, 4.42 (1H, brd s) |
| | | | | | CH, 4.64 (2H, brd s) |
| | | | | | CH, 4.80 (1H, brd s) |
| | | | | | aromatic Hs, 7.13-7.53 (9H) |
| 11 | CHCH(CH$_3$)$_2$CONH$_2$ | O | H | | (CDCl$_3$) |
| | | | | | CH$_3$, 1.12 (6H, m) |
| | | | | | CH, 2.42 (1H, brd s) |
| | | | | | NCH$_2$, 3.13, (4H, m) |
| | | | | | OCH$_2$, 3.76 (4H, m) |
| | | | | | CH 4.05 (1H, brd s) |
| | | | | | CH, 4.53 (1H, brd s) |
| | | | | | CH, 4.65 (1H, m) |
| | | | | | CH, 4.70 (1H, brd s) |
| | | | | | aromatic Hs, 7.13-7.53 (9H) |
| | | | | | NH, 5.55, 5.65 (1H, 2 brd s) |
| | | | | | NH, 6.50, 6.60 (1H, 2 brd s) |
| 12 | CHCHOHCH$_3$CONH$_2$ | O | H | | (CDCl$_3$) |
| | | | | | CH$_3$, 1.36, (3H, 2d) |
| | | | | | NCH$_2$, 3.12, (4H, m) |
| | | | | | OCH$_2$, 3.76 (4H, m) |
| | | | | | CH 4.11 (1H, brd m) |
| | | | | | CH, 4.50 (1H, brd s) |
| | | | | | CH, 4.58 (1H, m) |
| | | | | | CH, 4.72 (1H, m) |
| | | | | | CH, 4.87, 4.72 (1H, 2m) |
| | | | | | NH, 5.97 (1H, brd s) |
| | | | | | aromatic Hs, 7.14-7.53 (9H) |
| | | | | | NH, 7.67 (1H, brd s) |

TABLE C

CB1

| Ex # | R' | IC$_{50}$ | NMR ppm |
|---|---|---|---|
| 1 | N(CH$_3$)CH$_2$CONH$_2$ | + | (CDCl$_3$) |
|  |  |  | NCH$_3$, 2.85, (3H, s) |
|  |  |  | NCH$_3$, 3.24 (3H, d) |
|  |  |  | CH$_2$, 3.71 (2H, collapsed q) |
|  |  |  | CH, 4.13 (1H, m) |
|  |  |  | CH, 4.58 (1H, t) |
|  |  |  | CH, 4.70 (1H, m) |
|  |  |  | NH, 5.65 (1H, brd s) |
|  |  |  | NH, 6.88 (2H, 2 brd s) |
|  |  |  | aromatic Hs, 7.14-7.57 (9H) |
| 2 | N(CH$_3$)CH$_2$CO$_2$CH$_3$ |  | (CDCl$_3$) |
|  |  |  | NCH$_3$, 2.88, (3H, s) |
|  |  |  | NCH$_3$, 3.28 (3H, d) |
|  |  |  | OCH$_3$, 3.72 (3H, s) |
|  |  |  | CH$_2$, 3.91 (2H, q) |
|  |  |  | CH, 4.13 (1H, m) |
|  |  |  | CH, 4.61 (2H, m) |
|  |  |  | aromatic Hs, 7.14-7.54 (9H) |

Tables 1a-2b show a variety of examples of compounds of the present invention that are expected to be synthesized using the routes described above.

The preparation of the diphenyl pyrazolines with optional substituents on the 3-phenyl group can be prepared according to the procedures previously described [see Biorg Med Chem Lett, 2005, 15, 4793; U.S. Pat. No. 6,974,810; J. Med. Chem., 2004, 47, 627; and, J. Agric. Food Chem., 1979, 27, 406]. The pyrazolines can be condensed with chlorosulfonylisocyanate and dialkyl amines as previously described. Chlorination of the product sulfonamides with phosphorus pentachloride in heated cholorbenzene can produce the imidoylchlorides which were readily converted to the various amino ester adducts as previously described Biorg Med Chem Lett, 2005, 15, 4793; [J. Med. Chem., 2004, 47, 627]. Conversion of these esters to acids, carboxamides, substituted carboxamides, or di-amino acid variants can be carried via conventional methodology.

TABLE 1a

| Ex. # | X | Z | R$^d$ |
|---|---|---|---|
| 1. | C(NH)NH$_2$ | H | H |
| 2. | OCH$_2$-tetrazole | H | H |
| 3. | tetrazole | H | H |
| 4. | NHSO$_2$CH$_3$ | H | H |
| 5. | OCH$_2$CO$_2$Et | H | H |
| 6. | OCH$_2$CO$_2$H | H | H |
| 7. | OCH$_2$CH=CHCO$_2$Et | H | H |
| 8. | OCH$_2$CH=CHCO$_2$H | H | H |
| 9. | NHCOCH$_2$CO$_2$Et | H | H |
| 10. | NHCOCH$_2$CO$_2$H | H | H |
| 11. | OCH$_2$C$_6$H$_4$-2-CO$_2$Et | H | H |
| 12. | OCH$_2$C$_6$H$_4$-3-CO$_2$Et | H | H |
| 13. | OCH$_2$C$_6$H$_4$-4-CO$_2$Et | H | H |
| 14. | OCH$_2$C$_6$H$_4$-2-CO$_2$H | H | H |
| 15. | OCH$_2$C$_6$H$_4$-3-CO$_2$H | H | H |
| 16. | OCH$_2$C$_6$H$_4$-4-CO$_2$H | H | H |
| 17. | OCH$_2$C$_6$H$_4$-2-tetrazole | H | H |
| 18. | OCH$_2$C$_6$H$_4$-3-tetrazole | H | H |
| 19. | OCH$_2$C$_6$H$_4$-4-tetrazole | H | H |
| 20. | C(NH)NH$_2$ | OH | H |
| 21. | OCH$_2$-tetrazole | OH | H |
| 22. | tetrazole | OH | H |
| 23. | NHSO$_2$CH$_3$ | OH | H |
| 24. | OCH$_2$CO$_2$Et | OH | H |
| 25. | OCH$_2$CO$_2$H | OH | H |
| 26. | OCH$_2$CH=CHCO$_2$Et | OH | H |
| 27. | OCH$_2$CH=CHCO$_2$H | OH | H |
| 28. | NHCOCH$_2$CO$_2$Et | OH | H |
| 29. | NHCOCH$_2$CO$_2$H | OH | H |
| 30. | OCH$_2$C$_6$H$_4$-2-CO$_2$Et | OH | H |
| 31. | OCH$_2$C$_6$H$_4$-3-CO$_2$Et | OH | H |
| 32. | OCH$_2$C$_6$H$_4$-4-CO$_2$Et | OH | H |
| 33. | OCH$_2$C$_6$H$_4$-2-CO$_2$H | OH | H |
| 34. | OCH$_2$C$_6$H$_4$-3-CO$_2$H | OH | H |
| 35. | OCH$_2$C$_6$H$_4$-4-CO$_2$H | OH | H |
| 36. | OCH$_2$C$_6$H$_4$-2-tetrazole | OH | H |
| 37. | OCH$_2$C$_6$H$_4$-3-tetrazole | OH | H |
| 38. | OCH$_2$C$_6$H$_4$-4-tetrazole | OH | H |
| 39. | C(NH)NH$_2$ | H | CH$_2$OCH$_3$ |
| 40. | OCH$_2$-tetrazole | H | CH$_2$OCH$_3$ |
| 41. | tetrazole | H | CH$_2$OCH$_3$ |
| 42. | NHSO$_2$CH$_3$ | H | CH$_2$OCH$_3$ |
| 43. | OCH$_2$CO$_2$Et | H | CH$_2$OCH$_3$ |
| 44. | OCH$_2$CO$_2$H | H | CH$_2$OCH$_3$ |
| 45. | OCH$_2$CH=CHCO$_2$Et | H | CH$_2$OCH$_3$ |
| 46. | OCH$_2$CH=CHCO$_2$H | H | CH$_2$OCH$_3$ |
| 47. | NHCOCH$_2$CO$_2$Et | H | CH$_2$OCH$_3$ |
| 48. | NHCOCH$_2$CO$_2$H | H | CH$_2$OCH$_3$ |
| 49. | OCH$_2$C$_6$H$_4$-2-CO$_2$Et | H | CH$_2$OCH$_3$ |
| 50. | OCH$_2$C$_6$H$_4$-3-CO$_2$Et | H | CH$_2$OCH$_3$ |
| 51. | OCH$_2$C$_6$H$_4$-4-CO$_2$Et | H | CH$_2$OCH$_3$ |
| 52. | OCH$_2$C$_6$H$_4$-2-CO$_2$H | H | CH$_2$OCH$_3$ |
| 53. | OCH$_2$C$_6$H$_4$-3-CO$_2$H | H | CH$_2$OCH$_3$ |
| 54. | OCH$_2$C$_6$H$_4$-4-CO$_2$H | H | CH$_2$OCH$_3$ |
| 55. | OCH$_2$C$_6$H$_4$-2-tetrazole | H | CH$_2$OCH$_3$ |
| 56. | OCH$_2$C$_6$H$_4$-3-tetrazole | H | CH$_2$OCH$_3$ |
| 57. | OCH$_2$C$_6$H$_4$-4-tetrazole | H | CH$_2$OCH$_3$ |

TABLE 1a-continued

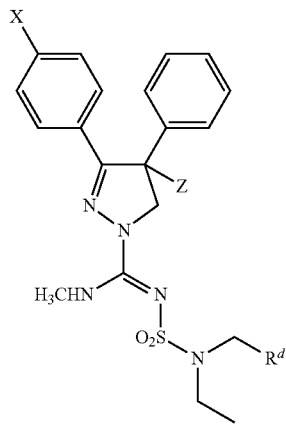

| Ex. # | X | Z | R$^d$ |
|---|---|---|---|
| 58. | C(NH)NH$_2$ | OH | CH$_2$OCH$_3$ |
| 59. | OCH$_2$-tetrazole | OH | CH$_2$OCH$_3$ |
| 60. | tetrazole | OH | CH$_2$OCH$_3$ |
| 61. | NHSO$_2$CH$_3$ | OH | CH$_2$OCH$_3$ |
| 62. | OCH$_2$CO$_2$Et | OH | CH$_2$OCH$_3$ |
| 63. | OCH$_2$CO$_2$H | OH | CH$_2$OCH$_3$ |
| 64. | OCH$_2$CH=CHCO$_2$Et | OH | CH$_2$OCH$_3$ |
| 65. | OCH$_2$CH=CHCO$_2$H | OH | CH$_2$OCH$_3$ |
| 66. | NHCOCH$_2$CO$_2$Et | OH | CH$_2$OCH$_3$ |
| 67. | NHCOCH$_2$CO$_2$H | OH | CH$_2$OCH$_3$ |
| 68. | OCH$_2$C$_6$H$_4$-2-CO$_2$Et | OH | CH$_2$OCH$_3$ |
| 69. | OCH$_2$C$_6$H$_4$-3-CO$_2$Et | OH | CH$_2$OCH$_3$ |
| 70. | OCH$_2$C$_6$H$_4$-4-CO$_2$Et | OH | CH$_2$OCH$_3$ |
| 71. | OCH$_2$C$_6$H$_4$-2-CO$_2$H | OH | CH$_2$OCH$_3$ |
| 72. | OCH$_2$C$_6$H$_4$-3-CO$_2$H | OH | CH$_2$OCH$_3$ |
| 73. | OCH$_2$C$_6$H$_4$-4-CO$_2$H | OH | CH$_2$OCH$_3$ |
| 74. | OCH$_2$C$_6$H$_4$-2-tetrazole | OH | CH$_2$OCH$_3$ |
| 75. | OCH$_2$C$_6$H$_4$-3-tetrazole | OH | CH$_2$OCH$_3$ |
| 76. | OCH$_2$C$_6$H$_4$-4-tetrazole | OH | CH$_2$OCH$_3$ |

TABLE 1b

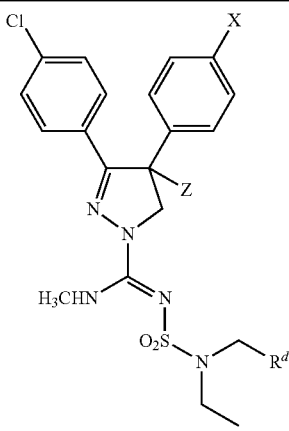

| Ex. # | X | Z | R$^d$ |
|---|---|---|---|
| 1. | C(NH)NH$_2$ | H | H |
| 2. | OCH$_2$-tetrazole | H | H |
| 3. | tetrazole | H | H |
| 4. | NHSO$_2$CH$_3$ | H | H |
| 5. | OCH$_2$CO$_2$Et | H | H |
| 6. | OCH$_2$CO$_2$H | H | H |
| 7. | OCH$_2$CH=CHCO$_2$Et | H | H |
| 8. | OCH$_2$CH=CHCO$_2$H | H | H |
| 9. | NHCOCH$_2$CO$_2$Et | H | H |
| 10. | NHCOCH$_2$CO$_2$H | H | H |

TABLE 1b-continued

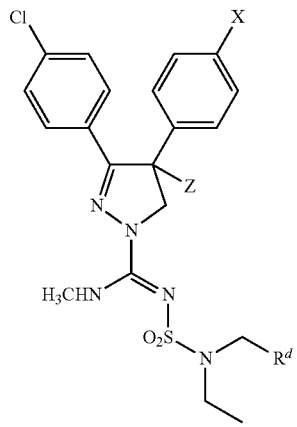

| Ex. # | X | Z | R$^d$ |
|---|---|---|---|
| 11. | OCH$_2$C$_6$H$_4$-2-CO$_2$Et | H | H |
| 12. | OCH$_2$C$_6$H$_4$-3-CO$_2$Et | H | H |
| 13. | OCH$_2$C$_6$H$_4$-4-CO$_2$Et | H | H |
| 14. | OCH$_2$C$_6$H$_4$-2-CO$_2$H | H | H |
| 15. | OCH$_2$C$_6$H$_4$-3-CO$_2$H | H | H |
| 16. | OCH$_2$C$_6$H$_4$-4-CO$_2$H | H | H |
| 17. | OCH$_2$C$_6$H$_4$-2-tetrazole | H | H |
| 18. | OCH$_2$C$_6$H$_4$-3-tetrazole | H | H |
| 19. | OCH$_2$C$_6$H$_4$-4-tetrazole | H | H |
| 20. | C(NH)NH2 | OH | H |
| 21. | OCH$_2$-tetrazole | OH | H |
| 22. | tetrazole | OH | H |
| 23. | NHSO$_2$CH$_3$ | OH | H |
| 24. | OCH$_2$CO$_2$Et | OH | H |
| 25. | OCH$_2$CO$_2$H | OH | H |
| 26. | OCH$_2$CH=CHCO$_2$Et | OH | H |
| 27. | OCH$_2$CH=CHCO$_2$H | OH | H |
| 28. | NHCOCH$_2$CO$_2$Et | OH | H |
| 29. | NHCOCH$_2$CO$_2$H | OH | H |
| 30. | OCH$_2$C$_6$H$_4$-2-CO$_2$Et | OH | H |
| 31. | OCH$_2$C$_6$H$_4$-3-CO$_2$Et | OH | H |
| 32. | OCH$_2$C$_6$H$_4$-4-CO$_2$Et | OH | H |
| 33. | OCH$_2$C$_6$H$_4$-2-CO$_2$H | OH | H |
| 34. | OCH$_2$C$_6$H$_4$-3-CO$_2$H | OH | H |
| 35. | OCH$_2$C$_6$H$_4$-4-CO$_2$H | OH | H |
| 36. | OCH$_2$C$_6$H$_4$-2-tetrazole | OH | H |
| 37. | OCH$_2$C$_6$H$_4$-3-tetrazole | OH | H |
| 38. | OCH$_2$C$_6$H$_4$-4-tetrazole | OH | H |
| 39. | C(NH)NH$_2$ | H | CH$_2$OCH$_3$ |
| 40. | OCH$_2$-tetrazole | H | CH$_2$OCH$_3$ |
| 41. | tetrazole | H | CH$_2$OCH$_3$ |
| 42. | NHSO$_2$CH$_3$ | H | CH$_2$OCH$_3$ |
| 43. | OCH$_2$CO$_2$Et | H | CH$_2$OCH$_3$ |
| 44. | OCH$_2$CO$_2$H | H | CH$_2$OCH$_3$ |
| 45. | OCH$_2$CH=CHCO$_2$Et | H | CH$_2$OCH$_3$ |
| 46. | OCH$_2$CH=CHCO$_2$H | H | CH$_2$OCH$_3$ |
| 47. | NHCOCH$_2$CO$_2$Et | H | CH$_2$OCH$_3$ |
| 48. | NHCOCH$_2$CO$_2$H | H | CH$_2$OCH$_3$ |
| 49. | OCH$_2$C$_6$H$_4$-2-CO$_2$Et | H | CH$_2$OCH$_3$ |
| 50. | OCH$_2$C$_6$H$_4$-3-CO$_2$Et | H | CH$_2$OCH$_3$ |
| 51. | OCH$_2$C$_6$H$_4$-4-CO$_2$Et | H | CH$_2$OCH$_3$ |
| 52. | OCH$_2$C$_6$H$_4$-2-CO$_2$H | H | CH$_2$OCH$_3$ |
| 53. | OCH$_2$C$_6$H$_4$-3-CO$_2$H | H | CH$_2$OCH$_3$ |
| 54. | OCH$_2$C$_6$H$_4$-4-CO$_2$H | H | CH$_2$OCH$_3$ |
| 55. | OCH$_2$C$_6$H$_4$-2-tetrazole | H | CH$_2$OCH$_3$ |
| 56. | OCH$_2$C$_6$H$_4$-3-tetrazole | H | CH$_2$OCH$_3$ |
| 57. | OCH$_2$C$_6$H$_4$-4-tetrazole | H | CH$_2$OCH$_3$ |
| 58. | C(NH)NH$_2$ | OH | CH$_2$OCH$_3$ |
| 59. | OCH$_2$-tetrazole | OH | CH$_2$OCH$_3$ |
| 60. | tetrazole | OH | CH$_2$OCH$_3$ |
| 61. | NHSO$_2$CH$_3$ | OH | CH$_2$OCH$_3$ |
| 62. | OCH$_2$CO$_2$Et | OH | CH$_2$OCH$_3$ |
| 63. | OCH$_2$CO$_2$H | OH | CH$_2$OCH$_3$ |
| 64. | OCH$_2$CH=CHCO$_2$Et | OH | CH$_2$OCH$_3$ |
| 65. | OCH$_2$CH=CHCO$_2$H | OH | CH$_2$OCH$_3$ |
| 66. | NHCOCH$_2$CO$_2$Et | OH | CH$_2$OCH$_3$ |
| 67. | NHCOCH$_2$CO$_2$H | OH | CH$_2$OCH$_3$ |

TABLE 1b-continued

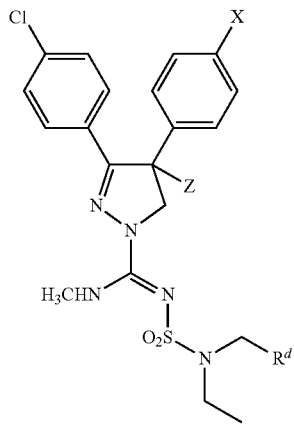

| Ex. # | X | Z | R$^d$ |
|---|---|---|---|
| 68. | OCH$_2$C$_6$H$_4$-2-CO$_2$Et | OH | CH$_2$OCH$_3$ |
| 69. | OCH$_2$C$_6$H$_4$-3-CO$_2$Et | OH | CH$_2$OCH$_3$ |
| 70. | OCH$_2$C$_6$H$_4$-4-CO$_2$Et | OH | CH$_2$OCH$_3$ |
| 71. | OCH$_2$C$_6$H$_4$-2-CO$_2$H | OH | CH$_2$OCH$_3$ |
| 72. | OCH$_2$C$_6$H$_4$-3-CO$_2$H | OH | CH$_2$OCH$_3$ |
| 73. | OCH$_2$C$_6$H$_4$-4-CO$_2$H | OH | CH$_2$OCH$_3$ |
| 74. | OCH$_2$C$_6$H$_4$-2-tetrazole | OH | CH$_2$OCH$_3$ |
| 75. | OCH$_2$C$_6$H$_4$-3-tetrazole | OH | CH$_2$OCH$_3$ |
| 76. | OCH$_2$C$_6$H$_4$-4-tetrazole | OH | CH$_2$OCH$_3$ |

TABLE 1c

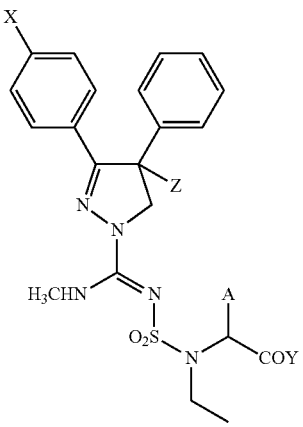

| Ex. # | A | X | Y | Z |
|---|---|---|---|---|
| 1. | H | Cl | OEt | H |
| 2. | H | OCH$_3$ | OEt | H |
| 3. | H | NHSO$_2$CH$_3$ | OEt | H |
| 4. | H | CN | OEt | H |
| 5. | H | C(NH)NH2 | OEt | H |
| 6. | H | OCH$_2$CONH$_2$ | OEt | H |
| 7. | H | Cl | OH | H |
| 8. | H | OCH$_3$ | OH | H |
| 9. | H | NHSO$_2$CH$_3$ | OH | H |
| 10. | H | CN | OH | H |
| 11. | H | C(NH)NH$_2$ | OH | H |
| 12. | H | OCH$_2$CONH$_2$ | OH | H |
| 13. | H | Cl | NH$_2$ | H |
| 14. | H | OCH$_3$ | NH$_2$ | H |
| 15. | H | NHSO$_2$CH$_3$ | NH$_2$ | H |
| 16. | H | CN | NH$_2$ | H |
| 17. | H | C(NH)NH$_2$ | NH$_2$ | H |
| 18. | H | OCH$_2$CONH$_2$ | NH$_2$ | H |
| 19. | H | Cl | NHCH$_2$CONH$_2$ | H |
| 20. | H | OCH$_3$ | NHCH$_2$CONH$_2$ | H |

TABLE 1c-continued

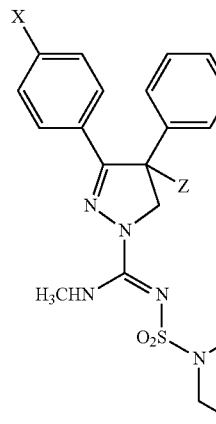

| Ex. # | A | X | Y | Z |
|---|---|---|---|---|
| 21. | H | NHSO$_2$CH$_3$ | NHCH$_2$CONH$_2$ | H |
| 22. | H | CN | NHCH$_2$CONH$_2$ | H |
| 23. | H | C(NH)NH2 | NHCH$_2$CONH$_2$ | H |
| 24. | H | OCH$_2$CONH$_2$ | NHCH$_2$CONH$_2$ | H |
| 25. | H | OCH$_3$ | OEt | H |
| 26. | H | NHSO$_2$CH$_3$ | OEt | H |
| 27. | H | CN | OEt | H |
| 28. | H | C(NH)NH2 | OEt | H |
| 29. | H | OCH$_2$CONH$_2$ | OEt | H |
| 30. | H | OCH$_2$CONH$_2$ | OEt | OH |
| 31. | H | Cl | OH | OH |
| 32. | H | OCH$_3$ | OH | OH |
| 33. | H | NHSO$_2$CH$_3$ | OH | OH |
| 34. | H | CN | OH | OH |
| 35. | H | C(NH)NH2 | OH | OH |
| 36. | H | OCH$_2$CONH$_2$ | OH | OH |
| 37. | H | Cl | NH$_2$ | OH |
| 38. | H | OCH$_3$ | NH$_2$ | OH |
| 39. | H | NHSO$_2$CH$_3$ | NH$_2$ | OH |
| 40. | H | CN | NH$_2$ | OH |
| 41. | H | C(NH)NH2 | NH$_2$ | OH |
| 42. | H | OCH$_2$CONH$_2$ | NH$_2$ | OH |
| 43. | H | Cl | NHCH$_2$CONH$_2$ | OH |
| 44. | H | OCH$_3$ | NHCH$_2$CONH$_2$ | OH |
| 45. | H | NHSO$_2$CH$_3$ | NHCH$_2$CONH$_2$ | OH |
| 46. | H | CN | NHCH$_2$CONH$_2$ | OH |
| 47. | H | C(NH)NH2 | NHCH$_2$CONH$_2$ | OH |
| 48. | H | OCH$_2$CONH$_2$ | NHCH$_2$CONH$_2$ | OH |
| 49. | CH(CH$_3$)OH | Cl | OEt | H |
| 50. | CH(CH$_3$)OH | OCH$_3$ | OEt | H |
| 51. | CH(CH$_3$)OH | NHSO$_2$CH$_3$ | OEt | H |
| 52. | CH(CH$_3$)OH | CN | OEt | H |
| 53. | CH(CH$_3$)OH | C(NH)NH2 | OEt | H |
| 54. | CH(CH$_3$)OH | OCH$_2$CONH$_2$ | OEt | H |
| 55. | CH(CH$_3$)OH | Cl | OH | H |
| 56. | CH(CH$_3$)OH | OCH$_3$ | OH | H |
| 57. | CH(CH$_3$)OH | NHSO$_2$CH$_3$ | OH | H |
| 58. | CH(CH$_3$)OH | CN | OH | H |
| 59. | CH(CH$_3$)OH | C(NH)NH2 | OH | H |
| 60. | CH(CH$_3$)OH | OCH$_2$CONH$_2$ | OH | H |
| 61. | CH(CH$_3$)OH | Cl | NH$_2$ | H |
| 62. | CH(CH$_3$)OH | OCH$_3$ | NH$_2$ | H |
| 63. | CH(CH$_3$)OH | NHSO$_2$CH$_3$ | NH$_2$ | H |
| 64. | CH(CH$_3$)OH | CN | NH$_2$ | H |
| 65. | CH(CH$_3$)OH | C(NH)NH2 | NH$_2$ | H |
| 66. | CH(CH$_3$)OH | OCH$_2$CONH$_2$ | NH$_2$ | H |
| 67. | CH(CH$_3$)OH | Cl | NHCH$_2$CONH$_2$ | H |
| 68. | CH(CH$_3$)OH | OCH$_3$ | NHCH$_2$CONH$_2$ | H |
| 69. | CH(CH$_3$)OH | NHSO$_2$CH$_3$ | NHCH$_2$CONH$_2$ | H |
| 70. | CH(CH$_3$)OH | CN | NHCH$_2$CONH$_2$ | H |
| 71. | CH(CH$_3$)OH | C(NH)NH2 | NHCH$_2$CONH$_2$ | H |
| 72. | CH(CH$_3$)OH | OCH$_2$CONH$_2$ | NHCH$_2$CONH$_2$ | H |
| 73. | CH(CH$_3$)OH | OCH$_3$ | OEt | H |
| 74. | CH(CH$_3$)OH | NHSO$_2$CH$_3$ | OEt | H |
| 75. | CH(CH$_3$)OH | CN | OEt | H |
| 76. | CH(CH$_3$)OH | C(NH)NH2 | OEt | H |
| 77. | CH(CH$_3$)OH | OCH$_2$CONH$_2$ | OEt | H |

TABLE 1c-continued

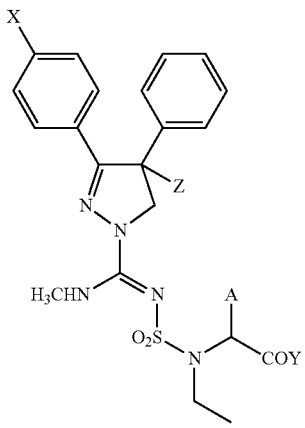

| Ex. # | A | X | Y | Z |
|---|---|---|---|---|
| 78. | CH(CH₃)OH | OCH₂CONH₂ | OEt | OH |
| 79. | CH(CH₃)OH | Cl | OH | OH |
| 80. | CH(CH₃)OH | OCH₃ | OH | OH |
| 81. | CH(CH₃)OH | NHSO₂CH₃ | OH | OH |
| 82. | CH(CH₃)OH | CN | OH | OH |
| 83. | CH(CH₃)OH | C(NH)NH2 | OH | OH |
| 84. | CH(CH₃)OH | OCH₂CONH₂ | OH | OH |
| 85. | CH(CH₃)OH | Cl | NH₂ | OH |
| 86. | CH(CH₃)OH | OCH₃ | NH₂ | OH |
| 87. | CH(CH₃)OH | NHSO₂CH₃ | NH₂ | OH |
| 88. | CH(CH₃)OH | CN | NH₂ | OH |
| 89. | CH(CH₃)OH | C(NH)NH2 | NH₂ | OH |
| 90. | CH(CH₃)OH | OCH₂CONH₂ | NH₂ | OH |
| 91. | CH(CH₃)OH | Cl | NHCH₂CONH₂ | OH |
| 92. | CH(CH₃)OH | OCH₃ | NHCH₂CONH₂ | OH |
| 93. | CH(CH₃)OH | NHSO₂CH₃ | NHCH₂CONH₂ | OH |
| 94. | CH(CH₃)OH | CN | NHCH₂CONH₂ | OH |
| 95. | CH(CH₃)OH | C(NH)NH2 | NHCH₂CONH₂ | OH |
| 96. | CH(CH₃)OH | OCH₂CONH₂ | NHCH₂CONH₂ | OH |

TABLE 1d

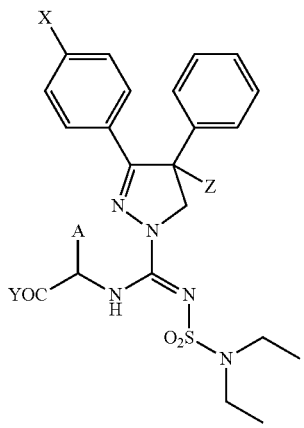

| Ex. # | A | X | Y | Z |
|---|---|---|---|---|
| 1. | H | Cl | OEt | H |
| 2. | H | OCH₃ | OEt | H |
| 3. | H | NHSO₂CH₃ | OEt | H |
| 4. | H | CN | OEt | H |
| 5. | H | C(NH)NH2 | OEt | H |
| 6. | H | OCH₂CONH₂ | OEt | H |
| 7. | H | Cl | OH | H |
| 8. | H | OCH₃ | OH | H |
| 9. | H | NHSO₂CH₃ | OH | H |
| 10. | H | CN | OH | H |

TABLE 1d-continued

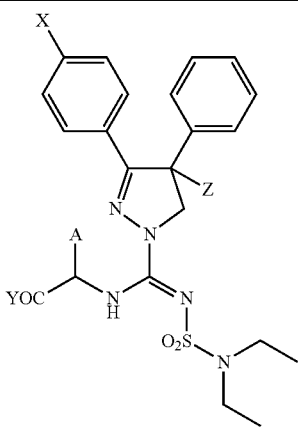

| Ex. # | A | X | Y | Z |
|---|---|---|---|---|
| 11. | H | C(NH)NH₂ | OH | H |
| 12. | H | OCH₂CONH₂ | OH | H |
| 13. | H | Cl | NH₂ | H |
| 14. | H | OCH₃ | NH₂ | H |
| 15. | H | NHSO₂CH₃ | NH₂ | H |
| 16. | H | CN | NH₂ | H |
| 17. | H | C(NH)NH₂ | NH₂ | H |
| 18. | H | OCH₂CONH₂ | NH₂ | H |
| 19. | H | Cl | NHCH₂CONH₂ | H |
| 20. | H | OCH₃ | NHCH₂CONH₂ | H |
| 21. | H | NHSO₂CH₃ | NHCH₂CONH₂ | H |
| 22. | H | CN | NHCH₂CONH₂ | H |
| 23. | H | C(NH)NH₂ | NHCH₂CONH₂ | H |
| 24. | H | OCH₂CONH₂ | CH₂CONH₂ | H |
| 25. | H | OCH₃ | OEt | H |
| 26. | H | NHSO₂CH₃ | OEt | H |
| 27. | H | CN | OEt | H |
| 28. | H | C(NH)NH₂ | OEt | H |
| 29. | H | OCH₂CONH₂ | OEt | H |
| 30. | H | OCH₂CONH₂ | OEt | OH |
| 31. | H | Cl | OH | OH |
| 32. | H | OCH₃ | OH | OH |
| 33. | H | NHSO₂CH₃ | OH | OH |
| 34. | H | CN | OH | OH |
| 35. | H | C(NH)NH₂ | OH | OH |
| 36. | H | OCH₂CONH₂ | OH | OH |
| 37. | H | Cl | NH₂ | OH |
| 38. | H | OCH₃ | NH₂ | OH |
| 39. | H | NHSO₂CH₃ | NH₂ | OH |
| 40. | H | CN | NH₂ | OH |
| 41. | H | C(NH)NH₂ | NH₂ | OH |
| 42. | H | OCH₂CONH₂ | NH₂ | OH |
| 43. | H | Cl | NHCH₂CONH₂ | OH |
| 44. | H | OCH₃ | NHCH₂CONH₂ | OH |
| 45. | H | NHSO₂CH₃ | NHCH₂CONH₂ | OH |
| 46. | H | CN | NHCH₂CONH₂ | OH |
| 47. | H | C(NH)NH₂ | NHCH₂CONH₂ | OH |
| 48. | H | OCH₂CONH₂ | NHCH₂CONH₂ | OH |
| 49. | CH(CH₃)OH | Cl | OEt | H |
| 50. | CH(CH₃)OH | OCH₃ | OEt | H |
| 51. | CH(CH₃)OH | NHSO₂CH₃ | OEt | H |
| 52. | CH(CH₃)OH | CN | OEt | H |
| 53. | CH(CH₃)OH | C(NH)NH2 | OEt | H |
| 54. | CH(CH₃)OH | OCH₂CONH₂ | OEt | H |
| 55. | CH(CH₃)OH | Cl | OH | H |
| 56. | CH(CH₃)OH | OCH₃ | OH | H |
| 57. | CH(CH₃)OH | NHSO₂CH₃ | OH | H |
| 58. | CH(CH₃)OH | CN | OH | H |
| 59. | CH(CH₃)OH | C(NH)NH2 | OH | H |
| 60. | CH(CH₃)OH | OCH₂CONH₂ | OH | H |

TABLE 1d-continued

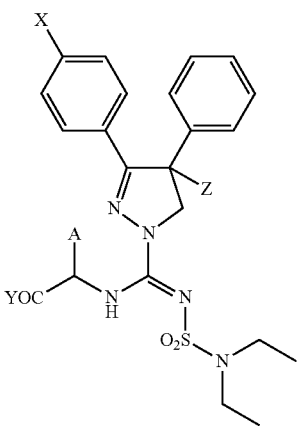

| Ex. # | A | X | Y | Z |
|---|---|---|---|---|
| 61. | CH(CH₃)OH | Cl | NH₂ | H |
| 62. | CH(CH₃)OH | OCH₃ | NH₂ | H |
| 63. | CH(CH₃)OH | NHSO₂CH₃ | NH₂ | H |
| 64. | CH(CH₃)OH | CN | NH₂ | H |
| 65. | CH(CH₃)OH | C(NH)NH₂ | NH₂ | H |
| 66. | CH(CH₃)OH | OCH₂CONH₂ | NH₂ | H |
| 67. | CH(CH₃)OH | Cl | NHCH₂CONH₂ | H |
| 68. | CH(CH₃)OH | OCH₃ | NHCH₂CONH₂ | H |
| 69. | CH(CH₃)OH | NHSO₂CH₃ | NHCH₂CONH₂ | H |
| 70. | CH(CH₃)OH | CN | NHCH₂CONH₂ | H |
| 71. | CH(CH₃)OH | C(NH)NH₂ | NHCH₂CONH₂ | H |
| 72. | CH(CH₃)OH | OCH₂CONH₂ | NHCH₂CONH₂ | H |
| 73. | CH(CH₃)OH | Cl | OEt | H |
| 74. | CH(CH₃)OH | OCH₃ | OEt | H |
| 75. | CH(CH₃)OH | NHSO₂CH₃ | OEt | H |
| 76. | CH(CH₃)OH | CN | OEt | H |
| 77. | CH(CH₃)OH | C(NH)NH₂ | OEt | H |
| 78. | CH(CH₃)OH | OCH₂CONH₂ | OEt | H |
| 79. | CH(CH₃)OH | Cl | OH | OH |
| 80. | CH(CH₃)OH | OCH₃ | OH | OH |
| 81. | CH(CH₃)OH | NHSO₂CH₃ | OH | OH |
| 82. | CH(CH₃)OH | CN | OH | OH |
| 83. | CH(CH₃)OH | C(NH)NH₂ | OH | OH |
| 84. | CH(CH₃)OH | OCH₂CONH₂ | OH | OH |
| 85. | CH(CH₃)OH | Cl | NH₂ | OH |
| 86. | CH(CH₃)OH | OCH₃ | NH₂ | OH |
| 87. | CH(CH₃)OH | NHSO₂CH₃ | NH₂ | OH |
| 88. | CH(CH₃)OH | CN | NH₂ | OH |
| 89. | CH(CH₃)OH | C(NH)NH₂ | NH₂ | OH |
| 90. | CH(CH₃)OH | OCH₂CONH₂ | NH₂ | OH |
| 91. | CH(CH₃)OH | Cl | NHCH₂CONH₂ | OH |
| 92. | CH(CH₃)OH | OCH₃ | NHCH₂CONH₂ | OH |
| 93. | CH(CH₃)OH | NHSO₂CH₃ | NHCH₂CONH₂ | OH |
| 94. | CH(CH₃)OH | CN | NHCH₂CONH₂ | OH |
| 95. | CH(CH₃)OH | C(NH)NH₂ | NHCH₂CONH₂ | OH |
| 96. | CH(CH₃)OH | OCH₂CONH₂ | NHCH₂CONH₂ | OH |

TABLE 2a

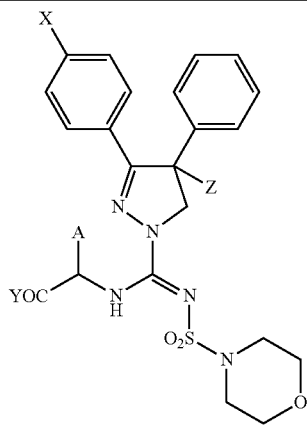

| Ex. # | A | X | Y | Z |
|---|---|---|---|---|
| 1. | H | Cl | OEt | H |
| 2. | H | OCH₃ | OEt | H |
| 3. | H | NHSO₂CH₃ | OEt | H |
| 4. | H | CN | OEt | H |
| 5. | H | C(NH)NH₂ | OEt | H |
| 6. | H | OCH₂CONH₂ | OEt | H |
| 7. | H | Cl | OH | H |
| 8. | H | OCH₃ | OH | H |
| 9. | H | NHSO₂CH₃ | OH | H |
| 10. | H | CN | OH | H |
| 11. | H | C(NH)NH2 | OH | H |
| 12. | H | OCH₂CONH₂ | OH | H |
| 13. | H | Cl | NH₂ | H |
| 14. | H | OCH₃ | NH₂ | H |
| 15. | H | NHSO₂CH₃ | NH₂ | H |
| 16. | H | CN | NH₂ | H |
| 17. | H | C(NH)NH2 | NH₂ | H |
| 18. | H | OCH₂CONH₂ | NH₂ | H |
| 19. | H | Cl | NHCH₂CONH₂ | H |
| 20. | H | OCH₃ | NHCH₂CONH₂ | H |
| 21. | H | NHSO₂CH₃ | NHCH₂CONH₂ | H |
| 22. | H | CN | NHCH₂CONH₂ | H |
| 23. | H | C(NH)NH2 | NHCH₂CONH₂ | H |
| 24. | H | OCH₂CONH₂ | NHCH₂CONH₂ | H |
| 25. | H | Cl | OEt | H |
| 26. | H | OCH₃ | OEt | H |
| 27. | H | NHSO₂CH₃ | OEt | H |
| 28. | H | CN | OEt | H |
| 29. | H | C(NH)NH2 | OEt | H |
| 30. | H | OCH₂CONH₂ | OEt | OH |
| 31. | H | Cl | OH | OH |
| 32. | H | OCH₃ | OH | OH |
| 33. | H | NHSO₂CH₃ | OH | OH |
| 34. | H | CN | OH | OH |
| 35. | H | C(NH)NH2 | OH | OH |
| 36. | H | OCH₂CONH₂ | OH | OH |
| 37. | H | Cl | NH₂ | OH |
| 38. | H | OCH₃ | NH₂ | OH |
| 39. | H | NHSO₂CH₃ | NH₂ | OH |
| 40. | H | CN | NH₂ | OH |
| 41. | H | C(NH)NH2 | NH₂ | OH |
| 42. | H | OCH₂CONH₂ | NH₂ | OH |
| 43. | H | Cl | NHCH₂CONH₂ | OH |
| 44. | H | OCH₃ | NHCH₂CONH₂ | OH |
| 45. | H | NHSO₂CH₃ | NHCH₂CONH₂ | OH |
| 46. | H | CN | NHCH₂CONH₂ | OH |
| 47. | H | C(NH)NH2 | NHCH₂CONH₂ | OH |
| 48. | H | OCH₂CONH₂ | NHCH₂CONH₂ | OH |
| 49. | CH(CH₃)OH | Cl | OEt | H |
| 50. | CH(CH₃)OH | OCH₃ | OEt | H |
| 51. | CH(CH₃)OH | NHSO₂CH₃ | OEt | H |
| 52. | CH(CH₃)OH | CN | OEt | H |
| 53. | CH(CH₃)OH | C(NH)NH2 | OEt | H |
| 54. | CH(CH₃)OH | OCH₂CONH₂ | OEt | H |
| 55. | CH(CH₃)OH | Cl | OH | H |
| 56. | CH(CH₃)OH | OCH₃ | OH | H |
| 57. | CH(CH₃)OH | NHSO₂CH₃ | OH | H |

TABLE 2a-continued

| Ex. # | A | X | Y | Z |
|---|---|---|---|---|
| 58. | CH(CH₃)OH | CN | OH | H |
| 59. | CH(CH₃)OH | C(NH)NH2 | OH | H |
| 60. | CH(CH₃)OH | OCH₂CONH₂ | OH | H |
| 61. | CH(CH₃)OH | Cl | NH₂ | H |
| 62. | CH(CH₃)OH | OCH₃ | NH₂ | H |
| 63. | CH(CH₃)OH | NHSO₂CH₃ | NH₂ | H |
| 64. | CH(CH₃)OH | CN | NH₂ | H |
| 65. | CH(CH₃)OH | C(NH)NH2 | NH₂ | H |
| 66. | CH(CH₃)OH | OCH₂CONH₂ | NH₂ | H |
| 67. | CH(CH₃)OH | Cl | NHCH₂CONH₂ | H |
| 68. | CH(CH₃)OH | OCH₃ | NHCH₂CONH₂ | H |
| 69. | CH(CH₃)OH | NHSO₂CH₃ | NHCH₂CONH₂ | H |
| 70. | CH(CH₃)OH | CN | NHCH₂CONH₂ | H |
| 71. | CH(CH₃)OH | C(NH)NH2 | NHCH₂CONH₂ | H |
| 72. | CH(CH₃)OH | OCH₂CONH₂ | NHCH₂CONH₂ | H |
| 73. | CH(CH₃)OH | Cl | OEt | H |
| 74. | CH(CH₃)OH | OCH₃ | OEt | H |
| 75. | CH(CH₃)OH | NHSO₂CH₃ | OEt | H |
| 76. | CH(CH₃)OH | CN | OEt | H |
| 77. | CH(CH₃)OH | C(NH)NH2 | OEt | H |
| 78. | CH(CH₃)OH | OCH₂CONH₂ | OEt | OH |
| 79. | CH(CH₃)OH | Cl | OH | OH |
| 80. | CH(CH₃)OH | OCH₃ | OH | OH |
| 81. | CH(CH₃)OH | NHSO₂CH₃ | OH | OH |
| 82. | CH(CH₃)OH | CN | OH | OH |
| 83. | CH(CH₃)OH | C(NH)NH2 | OH | OH |
| 84. | CH(CH₃)OH | OCH₂CONH₂ | OH | OH |
| 85. | CH(CH₃)OH | Cl | NH₂ | OH |
| 86. | CH(CH₃)OH | OCH₃ | NH₂ | OH |
| 87. | CH(CH₃)OH | NHSO₂CH₃ | NH₂ | OH |
| 88. | CH(CH₃)OH | CN | NH₂ | OH |
| 89. | CH(CH₃)OH | C(NH)NH2 | NH₂ | OH |
| 90. | CH(CH₃)OH | OCH₂CONH₂ | NH₂ | OH |
| 91. | CH(CH₃)OH | Cl | NHCH₂CONH₂ | OH |
| 92. | CH(CH₃)OH | OCH₃ | NHCH₂CONH₂ | OH |
| 93. | CH(CH₃)OH | NHSO₂CH₃ | NHCH₂CONH₂ | OH |
| 94. | CH(CH₃)OH | CN | NHCH₂CONH₂ | OH |
| 95. | CH(CH₃)OH | C(NH)NH2 | NHCH₂CONH₂ | OH |
| 96. | CH(CH₃)OH | OCH₂CONH₂ | NHCH₂CONH₂ | OH |

TABLE 2b

| Ex. # | X | Y (ring position) | Z |
|---|---|---|---|
| 1. | Cl | OEt (3) | H |
| 2. | OCH₃ | OEt (3) | H |
| 3. | NHSO₂CH₃ | OEt (3) | H |
| 4. | CN | OEt (3) | H |
| 5. | C(NH)NH2 | OEt (3) | H |
| 6. | OCH₂CONH₂ | OEt (3) | H |
| 7. | Cl | OH (3) | H |
| 8. | OCH₃ | OH (3) | H |
| 9. | NHSO₂CH₃ | OH (3) | H |
| 10. | CN | OH (3) | H |
| 11. | C(NH)NH2 | OH (3) | H |
| 12. | OCH₂CONH₂ | OH (3) | H |
| 13. | Cl | NH₂ (3) | H |
| 14. | OCH₃ | NH₂ (3) | H |
| 15. | NHSO₂CH₃ | NH₂ (3) | H |
| 16. | CN | NH₂ (3) | H |
| 17. | C(NH)NH2 | NH₂ (3) | H |
| 18. | OCH₂CONH₂ | NH₂ (3) | H |
| 19. | Cl | NHCH₂CONH₂ (3) | H |
| 20. | OCH₃ | NHCH₂CONH₂ (3) | H |
| 21. | NHSO₂CH₃ | NHCH₂CONH₂ (3) | H |
| 22. | CN | NHCH₂CONH₂ (3) | H |
| 23. | C(NH)NH2 | NHCH₂CONH₂ (3) | H |
| 24. | OCH₂CONH₂ | NHCH₂CONH₂ (3) | H |
| 25. | OCH₃ | OEt (4) | H |
| 26. | NHSO₂CH₃ | OEt (4) | H |
| 27. | CN | OEt (4) | H |
| 28. | C(NH)NH2 | OEt (4) | H |
| 29. | OCH₂CONH₂ | OEt (4) | H |
| 30. | OCH₂CONH₂ | OEt (4) | H |
| 31. | Cl | OH (4) | H |
| 32. | OCH₃ | OH (4) | H |
| 33. | NHSO₂CH₃ | OH (4) | H |
| 34. | CN | OH (4) | H |
| 35. | C(NH)NH2 | OH (4) | H |
| 36. | OCH₂CONH₂ | OH (4) | H |
| 37. | Cl | NH₂ (4) | H |
| 38. | OCH₃ | NH₂ (4) | H |
| 39. | NHSO₂CH₃ | NH₂ (4) | H |
| 40. | CN | NH₂ (4) | H |
| 41. | C(NH)NH2 | NH₂ (4) | H |
| 42. | OCH₂CONH₂ | NH₂ (4) | H |
| 43. | Cl | NHCH₂CONH₂ (4) | H |
| 44. | OCH₃ | NHCH₂CONH₂ (4) | H |
| 45. | NHSO₂CH₃ | NHCH₂CONH₂ (4) | H |
| 46. | CN | NHCH₂CONH₂ (4) | H |
| 47. | C(NH)NH2 | NHCH₂CONH₂ (4) | H |
| 48. | OCH₂CONH₂ | NHCH₂CONH₂ (4) | H |
| 49. | Cl | OEt (3) | OH |
| 50. | OCH₃ | OEt (3) | OH |
| 51. | NHSO₂CH₃ | OEt (3) | OH |
| 52. | CN | OEt (3) | OH |
| 53. | C(NH)NH2 | OEt (3) | OH |
| 54. | OCH₂CONH₂ | OEt (3) | OH |
| 55. | Cl | OH (3) | OH |
| 56. | OCH₃ | OH (3) | OH |
| 57. | NHSO₂CH₃ | OH (3) | OH |

TABLE 2b-continued

| Ex. # | X | Y (ring position) | Z |
|---|---|---|---|
| 58. | CN | OH (3) | OH |
| 59. | C(NH)NH2 | OH (3) | OH |
| 60. | OCH$_2$CONH$_2$ | OH (3) | OH |
| 61. | Cl | NH$_2$ (3) | OH |
| 62. | OCH$_3$ | NH$_2$ (3) | OH |
| 63. | NHSO$_2$CH$_3$ | NH$_2$ (3) | OH |
| 64. | CN | NH$_2$ (3) | OH |
| 65. | C(NH)NH2 | NH$_2$ (3) | OH |
| 66. | OCH$_2$CONH$_2$ | NH$_2$ (3) | OH |
| 67. | Cl | NHCH$_2$CONH$_2$ (3) | OH |
| 68. | OCH$_3$ | NHCH$_2$CONH$_2$ (3) | OH |
| 69. | NHSO$_2$CH$_3$ | NHCH$_2$CONH$_2$ (3) | OH |
| 70. | CN | NHCH$_2$CONH$_2$ (3) | OH |
| 71. | C(NH)NH2 | NHCH$_2$CONH$_2$ (3) | OH |
| 72. | OCH$_2$CONH$_2$ | NHCH$_2$CONH$_2$ (3) | OH |
| 73. | OCH$_3$ | OEt (4) | OH |
| 74. | NHSO$_2$CH$_3$ | OEt (4) | OH |
| 75. | CN | OEt (4) | OH |
| 76. | C(NH)NH2 | OEt (4) | OH |
| 77. | OCH$_2$CONH$_2$ | OEt (4) | OH |
| 78. | OCH$_2$CONH$_2$ | OEt (4) | OH |
| 79. | Cl | OH (4) | OH |
| 80. | OCH$_3$ | OH (4) | OH |
| 81. | NHSO$_2$CH$_3$ | OH (4) | OH |
| 82. | CN | OH (4) | OH |
| 83. | C(NH)NH2 | OH (4) | OH |
| 84. | OCH$_2$CONH$_2$ | OH (4) | OH |
| 85. | Cl | NH$_2$ (4) | OH |
| 86. | OCH$_3$ | NH$_2$ (4) | OH |
| 87. | NHSO$_2$CH$_3$ | NH$_2$ (4) | OH |
| 88. | CN | NH$_2$ (4) | OH |
| 89. | C(NH)NH2 | NH$_2$ (4) | OH |
| 90. | OCH$_2$CONH$_2$ | NH$_2$ (4) | OH |
| 91. | Cl | NHCH$_2$CONH$_2$ (4) | OH |
| 92. | OCH$_3$ | NHCH$_2$CONH$_2$ (4) | OH |
| 93. | NHSO$_2$CH$_3$ | NHCH$_2$CONH$_2$ (4) | OH |
| 94. | CN | NHCH$_2$CONH$_2$ (4) | OH |
| 95. | C(NH)NH2 | NHCH$_2$CONH$_2$ (4) | OH |
| 96. | OCH$_2$CONH$_2$ | NHCH$_2$CONH$_2$ (4) | OH |

Numerous modifications and variations of the present invention are possible in light of the above teachings. It is therefore to be understood that within the scope of the appended claims, the invention may be practiced otherwise that as specifically described herein.

What is claimed is:

1. A compound of Formula I or a stereoisomer or pharmaceutically acceptable salt thereof:

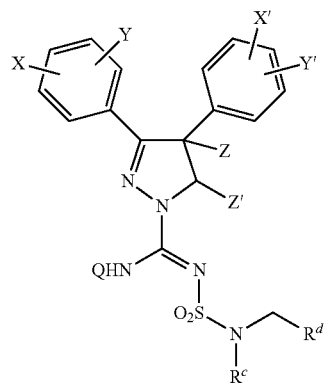

wherein:

X, Y, X', and Y', are independently selected from: H, $C_{1-6}$ alkyl, halogen, $CF_3$, O—$C_{1-6}$ alkyl, $NO_2$, $NR_2$, —CN, $O(CH_2)_nCO_2R$, $O(CH_2)_nCN$, $OCH_2CH=CHCO_2R$, $CH_2O(CH_2)_nCO_2R$, $CH_2OCH_2CH=CHCO_2R$, $O(CH_2)_nPO(OR)_2$, $CH_2O(CH_2)_nPO(OR)_2$, $NR^a(CH_2)_nCO_2R$, $NR^a(CH_2)_nPO(OR)_2$, $NR^aCH_2CH=CHCO_2R$, $NR^aSO_2R$, $NR^aCO(CH_2)_nCO_2R$, $NR^aCO(CH_2)_nCONR^a_2$, $O(CH_2)_nC_6H_4CO_2R$, $O(CH_2)_nC_6H_4(CH_2)_nCO_2R$, $CH_2O(CH_2)_nC_6H_4CO_2R$, $O(CH_2)_nC_6H_4CONR^a_2$, $O(CH_2)_nC_6H_4(CH_2)_nCONR^a_2$, $O(CH_2)_nC_6H_4$-tetrazole, $CH_2O(CH_2)_nC_6H_4CONR^a_2$, $CH_2O(CH_2)_nC_6H_4$-tetrazole, $O(CH_2)_nC_6H_4(CH_2)_n$-tetrazole, $NR^a(CH_2)_nC_6H_4CO_2R$, $CH_2NR^a(CH_2)_nC_6H_4CO_2R$, $NR^a(CH_2)_nC_6H_4(CH_2)_nCO_2R$, $NR^a(CH_2)_nC_6H_4CONR^a_2$, $CH_2NR^a(CH_2)_nC_6H_4CONR^a_2$, $NR^a(CH_2)_nC_6H_4(CH_2)_nCONR^a_2$, $NR^a(CH_2)_nC_6H_4$-tetrazole, $CH_2NR^a(CH_2)_nC_6H_4$-tetrazole, $NR^a(CH_2)_nC_6H_4(CH_2)_n$-tetrazole, CONHOH, $C(NH)NR^a_2$, $(CH_2)_nC(NH)NR^a_2$, $O(CH_2)_nCONR^a_2$, $O(CH_2)_nC(NH)NR^a_2$, $O(CH_2)_nC(NOH)NR^a_2$, $CH_2O(CH_2)_nCONR^a_2$, $NR^a(CH_2)_nCONR^a_2$, $OCH_2CH=CHCONR^a_2$, $CH_2OCH_2CH=CHCONR^a_2$, $NR^aCH_2CH=CHCONR^a_2$, $(CH_2)_m$-tetrazole, $O(CH_2)_n$-tetrazole, $O(CH_2CH_2O)_pR$, $NR^a(CH_2CH_2O)_pR$, and $SO_2NHCH_3$;

Z is selected from: H, $C_{1-6}$ alkyl, OH, O—$C_{1-6}$ alkyl, $O(CH_2CH_2O)_pR$, OC(O)—$C_{1-6}$ alkyl, $O(CH_2)_nCO_2R$, $OCH_2CH=CHCO_2R$, $O(CH_2)_nPO(OR)_2$, $O(CH_2)_nCONR^a_2$, $O(CH_2)_nC(NH)NH_2$, $O(CH_2)_nC(NOH)NR^a_2$, $OCH_2CH=CHCONR^a_2$, $O(CH_2)_n$-phenyl-$(CH_2)_mCO_2R$, and $O(CH_2)_n$-phenyl-$(CH_2)_m$-tetrazole;

Z' is selected from H, $CO_2R$, $CONR^a_2$, and $CONR^aCHA$-$CONR^a_2$;

Q is selected from: H, $C_{1-6}$ alkyl, $(CH_2CH_2O)_pR$, $(CH_2)_n$-aryl, $(CH_2)_m$-aryl-$(CH_2)_mCO_2R$, $(CH_2)_m$-aryl-$(CH_2)_mC(O)NR^a_2$, $(CH_2)_n$-heteroaryl, $(CH_2)_m$-heteroaryl-$(CH_2)_mCO_2R$, $(CH_2)_m$-heteroaryl-$(CH_2)_mC(O)NR^a_2$, $(CH_2)_mCHA(CH_2)_mC(O)NR^a_2$, $(CH_2)_mCAA''(CH_2)_mC(O)NR^a_2$, $(CH_2)_mCHA(CH_2)_mCO_2R$, $(CH_2)_mCAA''(CH_2)_mCO_2R$, $(CH_2)_mCHA(CH_2)_mSO_2NR^a_2$, $(CH_2)_mCHA(CH_2)_mSO_3R$, $(CH_2)_mCHA(CH_2)_nC(NH)NH_2$, $(CH_2)_mCHA(CH_2)_mC(NOH)NH_2$, $(CH_2)_mCHA$ $(CH_2)_mCONHCHA(CH_2)_mCO_2R$, $(CH_2)_mCAA''$ (CH₂)ₘCONHCHA(CH₂)ₘCO₂R, (CH₂)ₘCHA(CH₂)ₘCONHCHA(CH₂)ₘCONHCHA(CH₂)ₘCO₂R, (CH₂)ₘCHA(CH₂)ₘCONHCHA(CH₂)ₘCONR$^a$₂, (CH₂)ₘCAA"(CH₂)ₘCONHCHA(CH₂)ₘCONR$^a$₂, (CH₂)ₘCHA(CH₂)ₘCONHCHA(CH₂)ₘSO₂NR$^a$₂, (CH₂)ₘCAA"(CH₂)ₘCONHCHA(CH₂)ₘSO₂NR$^a$₂, (CH₂)ₘCHA(CH₂)ₘCONHCHA(CH₂)ₘCONHCHA (CH₂)ₘCONR$^a$₂, C₃-C₆-cyclic amino-(CH₂)ₘCO₂R, C₃-C₆-cyclic amino-(CH₂)ₘCONR$^a$₂, C₃-C₆-cycloalkylene-(CH₂)ₘCO₂R, and C₃-C₆-cycloalkylene-(CH₂)ₘCONR$^a$₂;

A is selected from H, C₁₋₆ alkyl, (CH₂)ₘC₃₋₆-cycloalkyl, OH, CH₂OH, CH(CH₃)OH, C(CH₃)₂OH, (CH₂)ₙCO₂R$^b$, (CH₂)ₙC(O)NR$^b$₂, and (CH₂)ₘ-phenyl, wherein the phenyl is substituted with 0-3 groups selected from H, C₁₋₄ alkyl, halogen, CF₃, OH, O—C₁₋₄ alkyl, NO₂, —CN, C(O)NH₂, C(NH)NH₂, and NHSO₂CH₃;

A" is C₁₋₆ alkyl;

alternatively, A and A" form a C₃₋₆ cycloalkyl group with the carbon to which they both are attached;

R is independently selected from H, (CH₂)ₘ(CHR$^b$)ₙ(CH₂)ₘOH, CH(CH₂OH)₂, C₁₋₆ alkyl, C₂₋₆ alkenyl, and C₂₋₆ alkynyl;

R$^a$ is independently selected from H, (CH₂)ₘ(CHR)ₙ(CH₂)ₘOH, C₁₋₆ alkyl, C₂₋₆ alkenyl, and C₂₋₆ alkynyl;

R$^b$ is independently selected from H, C₁₋₆ alkyl, C₂₋₆ alkenyl, and C₂₋₆ alkynyl;

R$^c$ is selected from H, C₁₋₆ alkyl, C₂₋₆ alkenyl, C₂₋₆ alkynyl, C₁₋₆ alkylidene-O—C₁₋₂ alkyl, (CH₂)ₘCHA(CH₂)ₙC(O)NR$^a$₂, (CH₂)ₘCAA"(CH₂)ₘC(O)NR$^a$₂, (CH₂)ₘCHA(CH₂)ₘCO₂R, (CH₂)ₘCAA"(CH₂)ₘCO₂R, (CH₂)ₘCHA(CH₂)ₘSO₂NR$^a$₂, (CH₂)ₘCHA(CH₂)ₘSO₃R, (CH₂)ₘCHA(CH₂)ₘC(NH)NH₂, (CH₂)ₘCHA(CH₂)ₘC(NOH)NH₂, (CH₂)ₘCHA(CH₂)ₘCONHCHA(CH₂)ₘCO₂R, (CH₂)ₘCAA"(CH₂)ₘCONHCHA(CH₂)ₘCO₂R, (CH₂)ₘCHA(CH₂)ₘCONHCHA(CH₂)ₘCONHCHA(CH₂)ₘCO₂R, (CH₂)ₘCHA(CH₂)ₘCONHCHA(CH₂)ₘCONR$^a$₂, (CH₂)ₘCAA"(CH₂)ₘCONHCHA(CH₂)ₘCONR$^a$₂, (CH₂)ₘCHA(CH₂)ₘCONHCHA(CH₂)ₘCONHCHA(CH₂)ₘCONR$^a$₂, C₃-C₆-cyclic amino-(CH₂)ₘCO₂R, C₃-C₆-cyclic amino-(CH₂)ₘCONR$^a$₂, C₃-C₆-cycloalkylene-(CH₂)ₘCO₂R, and C₃-C₆-cycloalkylene-(CH₂)ₘCONR$^a$₂;

R$^d$ is selected from H, C₁₋₆ alkyl, C₂₋₆ alkenyl, C₂₋₆ alkynyl, OC₃₋₄ alkenyl, OC₃₋₄ alkynyl, and C₁₋₆ alkylidene-O—C₁₋₂ alkyl;

alternatively, R$^c$ and R$^d$ taken together form —(CH₂)ₙ'—U—(CH₂)ₙ'—, and the ring formed by N(R$^c$)CH₂R$^d$ is substituted with 0-2 R$^e$ at other than group U;

U is selected from O, S, SO, SO₂, CHR$^e$, and NR$^e$;

R$^e$ is selected from H, C₁₋₆ alkyl, C₃₋₆ alkenyl, C₃₋₆ alkynyl, C₂₋₆ alkylidene-O—C₁₋₂ alkyl, (CH₂)ₘCO₂R, (CH₂)ₘCONR$^a$₂, (CH₂)ₘCONH(CH₂)ₘCHA(CH₂)ₘCONR$^a$₂, and (CH₂)ₘCONH(CH₂)ₘCHA(CH₂)ₘCONR$^a$₂;

p is independently selected from 2, 3, 4, 5, 6, 7, 8, 9, 10, 11, and 12;

m is independently selected from 0, 1, 2, 3, and 4; and, n is independently selected from 1, 2, 3, and 4; and n' is independently selected from 1 and 2;

provided that at least one of (a)-(f) is satisfied:
 a. at least one of X, Y, X', and Y' is other than H, C₁₋₆ alkyl, halogen, CF₃, O—C₁₋₆ alkyl, NO₂, NR₂, and SO₂NHCH₃;
 b. Z is other than H, C₁₋₆ alkyl, OH, O—C₁₋₆ alkyl, and OC(O)—C₁₋₆ alkyl;
 c. Z' is other than H;
 d. Q is other than H, C₁₋₆ alkyl, (CH₂)ₙ-aryl, and (CH₂)ₙ-heteroaryl;
 e. R$^c$ is other than H, C₁₋₆ alkyl, C₂₋₆ alkenyl, C₂₋₆ alkynyl, and C₁₋₆ alkylidene-O—C₁₋₂ alkyl; and/or
 f. R$^e$ is present and is other than H, C₁₋₆ alkyl, C₃₋₆ alkenyl, and C₃₋₆ alkynyl.

2. A compound of claim 1, wherein the compound is of Ia or a stereoisomer or pharmaceutically acceptable salt thereof:

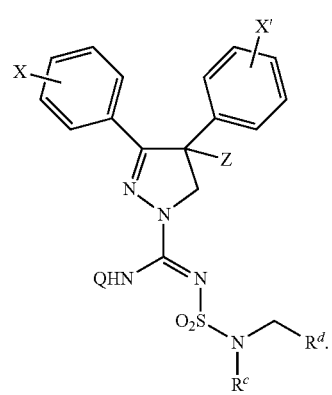

Ia

3. A compound of claim 1, wherein the compound is of Ib or a stereoisomer or pharmaceutically acceptable salt thereof:

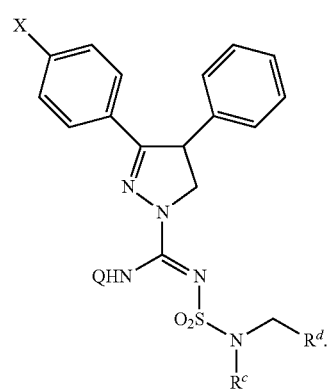

Ib

4. A compound of claim 1, wherein:

X, Y, X', and Y', are independently selected from: O(CH₂)ₙCO₂R, OCH₂CH=CHCO₂R, CH₂O(CH₂)ₙCO₂R, CH₂OCH₂CH=CHCO₂R, O(CH₂)ₙPO(OR)₂, CH₂O(CH₂)ₙPO(OR)₂, NR$^a$(CH₂)ₙCO₂R, NR$^a$(CH₂)ₙPO(OR)₂, NR$^a$CH₂CH=CHCO₂R, NR$^a$SO₂R, NR$^a$CO(CH₂)ₙCO₂R, NR$^a$CO(CH₂)ₙCONR$^a$₂, O(CH₂)ₙC₆H₄CO₂R, O(CH₂)ₙC₆H₄(CH₂)ₙCO₂R, CH₂O(CH₂)ₙC₆H₄CO₂R, O(CH₂)ₙC₆H₄CONR$^a$₂, O(CH₂)ₙC₆H₄(CH₂)ₙCONR$^a$₂, O(CH₂)ₙC₆H₄-tetrazole, CH₂O(CH₂)ₙC₆H₄CONR$^a$₂, CH₂O(CH₂)ₙC₆H₄-tetrazole, O(CH₂)ₙC₆H₄(CH₂)ₙ-tetrazole, NR$^a$(CH₂)ₙC₆H₄CO₂R, CH₂NR$^a$(CH₂)ₙC₆H₄CO₂R, NR$^a$(CH₂)ₙC₆H₄(CH₂)ₙCO₂R, NR$^a$(CH₂)ₙC₆H₄CONR$^a$₂, CH₂NR$^a$(CH₂)ₙC₆H₄CONR$^a$₂, NR$^a$(CH₂)ₙC₆H₄(CH₂)ₙCONR$^a$₂, NR$^a$(CH₂)ₙC₆H₄-tetrazole, CH₂NR$^a$(CH₂)ₙC₆H₄-tetrazole, NR$^a$(CH₂)ₙC₆H₄(CH₂)ₙ-tetrazole, CONHOH, C(NH)NR$^a$₂, (CH₂)ₙC(NH)NR$^a$₂, O(CH₂)ₙCONR$^a$₂, O(CH₂)ₙC(NH)NR$^a$₂, O(CH$_2$)$_n$C(NOH)NR$^a$$_2$, CH$_2$O(CH$_2$)$_n$CONR$^a$$_2$, NR$^a$(CH$_2$)$_n$CONR$^a$$_2$, OCH$_2$CH=CHCONR$^a$$_2$, CH$_2$OCH$_2$CH=CHCONR$^a$$_2$, NR$^a$CH$_2$CH=CHCONR$^a$$_2$, (CH$_2$)$_m$-tetrazole, O(CH$_2$)$_n$-tetrazole, O(CH$_2$CH$_2$O)$_p$R, NR$^a$(CH$_2$CH$_2$O)$_p$R, and SO$_2$NHCH$_3$;

Z is selected from: H, C$_{1-6}$ alkyl, OH, O—C$_{1-6}$ alkyl, O(CH$_2$CH$_2$O)$_p$R, and OC(O)—C$_{1-6}$ alkyl;

Q is selected from: H, C$_{1-6}$ alkyl, (CH$_2$)$_n$-aryl, (CH$_2$CH$_2$O)$_p$R, and (CH$_2$)$_n$-heteroaryl;

R is independently selected from H, (CH$_2$)$_m$(CHR$^b$)$_n$(CH$_2$)$_m$OH, CH(CH$_2$OH)$_2$, C$_{1-6}$ alkyl, C$_{2-6}$ alkenyl, and C$_{2-6}$ alkynyl;

R$^a$ is independently selected from H, (CH$_2$)$_m$(CHR)$_n$(CH$_2$)$_m$OH, C$_{1-6}$ alkyl, C$_{2-6}$ alkenyl, and C$_{2-6}$ alkynyl;

R$^c$ is selected from H, C$_{1-6}$ alkyl, C$_{2-6}$ alkenyl, C$_{2-6}$ alkynyl, C$_{1-6}$ alkylidene-O—C$_{1-2}$ alkyl;

R$^d$ is selected from H, C$_{1-6}$ alkyl, C$_{2-6}$ alkenyl, C$_{2-6}$ alkynyl, OC$_{3-4}$ alkenyl, OC$_{3-4}$ alkynyl, and C$_{1-6}$ alkylidene-O—C$_{1-2}$ alky;

alternatively, R$^c$ and R$^d$ taken together form —(CH$_2$)$_{n'}$—U—(CH$_2$)$_{n'}$—, and the ring formed by N(R$^c$)CH$_2$R$^d$ is substituted with 0-2 R$^e$ at other than group U;

U is selected from O, S, SO, SO$_2$, CHR$^e$, and NR$^e$;

R$^e$ is selected from H, C$_{1-6}$ alkyl, C$_{3-6}$ alkenyl, C$_{3-6}$ alkynyl, and C$_{2-6}$ alkylidene-O—C$_{1-2}$ alkyl;

p is independently selected from 2, 3, 4, 5, 6, 7, 8, 9, 10, 11, and 12;

m is independently selected from 0, 1, 2, 3, and 4;

n is independently selected from 1, 2, 3, and 4; and n' is independently selected from 1 and 2.

5. A compound of claim 1, wherein:

X, Y, X', and Y', are independently selected from: H, C$_{1-6}$ alkyl, halogen, CF$_3$, O—C$_{1-6}$ alkyl, NO$_2$, NR$_2$, —CN, O(CH$_2$)$_n$CN, NR$^a$SO$_2$R, and SO$_2$NHCH$_3$;

Z is selected from: O(CH$_2$)$_n$CO$_2$R, OCH$_2$CH=CHCO$_2$R, O(CH$_2$)$_n$PO(OR)$_2$, O(CH$_2$)$_n$CONR$^a$$_2$, O(CH$_2$)$_n$C(NH)NH$_2$, O(CH$_2$)$_n$C(NOH)NR$^a$$_2$, OCH$_2$CH=CHCONR$^a$$_2$, O(CH$_2$)$_n$-phenyl-(CH$_2$)$_m$CO$_2$R, and O(CH$_2$)$_n$-phenyl-(CH$_2$)$_m$-tetrazole;

Q is selected from: H, C$_{1-6}$ alkyl, (CH$_2$)$_n$-aryl, (CH$_2$CH$_2$O)$_p$R, and (CH$_2$)$_n$-heteroaryl;

R is independently selected from H, (CH$_2$)$_m$(CHR$^b$)$_n$(CH$_2$)$_m$OH, CH(CH$_2$OH)$_2$, C$_{1-6}$ alkyl, C$_{2-6}$ alkenyl, and C$_{2-6}$ alkynyl;

R$^a$ is independently selected from H, (CH$_2$)$_m$(CHR)$_n$(CH$_2$)$_m$OH, C$_{1-6}$ alkyl, C$_{2-6}$ alkenyl, and C$_{2-6}$ alkynyl;

R$^b$ is independently selected from H, C$_{1-6}$ alkyl, C$_{2-6}$ alkenyl, and C$_{2-6}$ alkynyl;

R$^c$ is selected from H, C$_{1-6}$ alkyl, C$_{2-6}$ alkenyl, C$_{2-6}$ alkynyl, and C$_{1-6}$ alkylidene-O—C$_{1-2}$ alkyl;

R$^d$ is selected from H, C$_{1-6}$ alkyl, C$_{2-6}$ alkenyl, C$_{2-6}$ alkynyl, OC$_{3-4}$ alkenyl, OC$_{3-4}$ alkynyl, and C$_{1-6}$ alkylidene-O—C$_{1-2}$ alkyl;

alternatively, R$^c$ and R$^d$ taken together form —(CH$_2$)$_{n'}$—U—(CH$_2$)$_{n'}$—, and the ring formed by N(R$^c$)CH$_2$R$^d$ is substituted with 0-2 R$^e$ at other than group U;

U is selected from O, S, SO, SO$_2$, CHR$^e$, and NR$^e$;

R$^e$ is selected from H, C$_{1-6}$ alkyl, C$_{3-6}$ alkenyl, C$_{3-6}$ alkynyl, and C$_{2-6}$ alkylidene-O—C$_{1-2}$ alkyl;

p is independently selected from 2, 3, 4, 5, 6, 7, 8, 9, 10, 11, and 12;

m is independently selected from 0, 1, 2, 3, and 4;

n is independently selected from 1, 2, 3, and 4; and, n' is independently selected from 1 and 2.

6. A compound of claim 1, wherein:

X, Y, X', and Y', are independently selected from: H, C$_{1-6}$ alkyl, halogen, CF$_3$, O—C$_{1-6}$ alkyl, NO$_2$, NR$_2$, —CN, O(CH$_2$)$_n$CN, NR$^a$SO$_2$R, O(CH$_2$CH$_2$O)$_p$R, NR$^a$(CH$_2$CH$_2$O)$_p$R, and SO$_2$NHCH$_3$;

Z is selected from: H, C$_{1-6}$ alkyl, OH, O—C$_{1-6}$ alkyl, and O(CH$_2$CH$_2$O)$_p$R, OC(O)—C$_{1-6}$ alkyl;

Z' is selected from CO$_2$R and CONR$^a$$_2$;

Q is selected from: H, C$_{1-6}$ alkyl, (CH$_2$)$_n$-aryl, (CH$_2$CH$_2$O)$_p$R, and (CH$_2$)$_n$-heteroaryl;

R is independently selected from H, (CH$_2$)$_m$(CHR$^b$)$_n$(CH$_2$)$_m$OH, CH(CH$_2$OH)$_2$, C$_{1-6}$ alkyl, C$_{2-6}$ alkenyl, and C$_{2-6}$ alkynyl;

R$^a$ is independently selected from H, (CH$_2$)$_m$(CHR)$_n$(CH$_2$)$_m$OH, C$_{1-6}$ alkyl, C$_{2-6}$ alkenyl, and C$_{2-6}$ alkynyl;

R$^b$ is independently selected from H, C$_{1-6}$ alkyl, C$_{2-6}$ alkenyl, and C$_{2-6}$ alkynyl;

R$^c$ is selected from H, C$_{1-6}$ alkyl, C$_{2-6}$ alkenyl, C$_{2-6}$ alkynyl, and C$_{1-6}$ alkylidene-O—C$_{1-2}$ alkyl;

R$^d$ is selected from H, C$_{1-6}$ alkyl, C$_{2-6}$ alkenyl, C$_{2-6}$ alkynyl, OC$_{3-4}$ alkenyl, OC$_{3-4}$ alkynyl, and C$_{1-6}$ alkylidene-O—C$_{1-2}$ alkyl;

alternatively, R$^c$ and R$^d$ taken together form —(CH$_2$)$_{n'}$—U—(CH$_2$)$_{n'}$—, and the ring formed by N(R$^c$)CH$_2$R$^d$ is substituted with 0-2 R$^e$ at other than group U;

U is selected from O, S, SO, SO$_2$, CHR$^e$, and NR$^e$;

R$^e$ is selected from H, C$_{1-6}$ alkyl, C$_{3-6}$ alkenyl, and C$_{3-6}$ alkynyl, C$_{2-6}$ alkylidene-O—C$_{1-2}$ alkyl;

p is independently selected from 2, 3, 4, 5, 6, 7, 8, 9, 10, 11, and 12;

m is independently selected from 0, 1, 2, 3, and 4;

n is independently selected from 1, 2, 3, and 4; and, n' is independently selected from 1 and 2.

7. A compound of claim 1, wherein the compound is of formula Ic or a stereoisomer or pharmaceutically acceptable salt thereof:

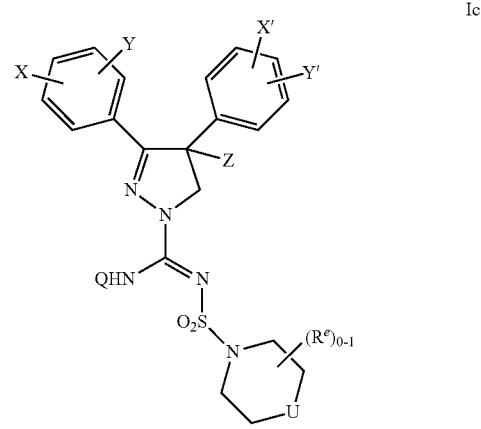

Ic wherein:

X, Y, X', and Y' are individually selected from the following: H, C$_{1-4}$ alkyl, halogen, CF$_3$, O—C$_{1-4}$ alkyl, NO$_2$, —CN, O(CH$_2$CH$_2$O)$_p$R, NR$^a$(CH$_2$CH$_2$O)$_p$R, and NR$_2$;

Z is selected from: H, C$_{1-4}$ alkyl, OH, O—C$_{1-4}$ alkyl, acetyloxy, and propionyloxy;

Q is selected from: H, C$_{1-6}$ alkyl, (CH$_2$CH$_2$O)$_p$R, (CH$_2$)$_n$-aryl, (CH$_2$)$_m$-aryl-(CH$_2$)$_m$CO$_2$R, (CH$_2$)$_m$-aryl-(CH$_2$)$_m$C(O)NR$^a$$_2$, (CH$_2$)$_n$-heteroaryl, (CH$_2$)$_m$-heteroaryl-(CH$_2$)$_m$CO$_2$R, (CH$_2$)$_m$-heteroaryl-(CH$_2$)$_m$C(O)NR$^a$$_2$, (CH$_2$)$_m$CHA(CH$_2$)$_m$C(O)NR$^a$$_2$, (CH$_2$)$_m$CAA"(CH$_2$)$_m$C (O)NR$^a_2$, (CH$_2$)$_m$CHA(CH$_2$)$_m$SO$_2$NR$^a_2$, (CH$_2$)$_m$CHA(CH$_2$)$_m$CONHCHA(CH$_2$)$_m$CONR$^a_2$, (CH$_2$)$_m$CAA"(CH$_2$)$_m$CONHCHA(CH$_2$)$_m$CONR$^a_2$, (CH$_2$)$_m$CHA(CH$_2$)$_m$CONHCHA(CH$_2$)$_m$SO$_2$NR$^a_2$, (CH$_2$)$_m$CAA"(CH$_2$)$_m$CONHCHA(CH$_2$)$_m$SO$_2$NR$^a_2$, (CH$_2$)$_m$CHA(CH$_2$)$_m$CONHCHA(CH$_2$)$_m$CONHCHA(CH$_2$)$_m$CONR$^a_2$, C$_3$-C$_6$-cyclic amino-(CH$_2$)$_m$CONR$^a_2$, and C$_3$-C$_6$-cycloalkylene-(CH$_2$)$_m$CONR$^a_2$;

A is selected from H, C$_{1-4}$ alkyl, (CH$_2$)$_m$C$_{3-6}$-cycloalkyl, OH, CH$_2$OH, CH(CH$_3$)OH, C(CH$_3$)$_2$OH, (CH$_2$)$_n$CO$_2$R$^b$, (CH$_2$)$_n$C(O)NR$^b_2$, and (CH$_2$)$_m$-phenyl, wherein the phenyl is substituted with 0-3 groups selected from H, C$_{1-4}$ alkyl, halogen, CF$_3$, OH, O—C$_{1-4}$ alkyl, NO$_2$, —CN, C(O)NH$_2$, C(NH)NH$_2$, and NHSO$_2$CH$_3$;

R is independently selected from H, C$_{1-6}$ alkyl, C$_{2-6}$ alkenyl, and C$_{2-6}$ alkynyl;

R$^b$ is independently selected from H, C$_{1-6}$ alkyl, C$_{2-6}$ alkenyl, and C$_{2-6}$ alkynyl;

U is selected from O, SO, SO$_2$, CHR$^e$, and NR$^e$;

R$^e$ is selected from (CH$_2$)$_m$CO$_2$R, (CH$_2$)$_m$CONR$^a_2$, (CH$_2$)$_m$CONH(CH$_2$)$_m$CHA(CH$_2$)$_m$CONR$^a_2$, and (CH$_2$)$_m$CONH(CH$_2$)$_m$CHA(CH$_2$)$_m$CONR$^a_2$;

p is independently selected from 2, 3, 4, 5, 6, 7, and 8;

m is independently selected from 0, 1, 2, and 3;

n is independently selected from 1, 2, and 3;

n' is independently selected from 1 and 2; and/or provided that at least one of (a)-(c) is satisfied:
 a. at least one of X, Y, X', and Y' is other than H, C$_{1-6}$ alkyl, halogen, CF$_3$, O—C$_{1-6}$ alkyl, NO$_2$, and NR$_2$;
 b. Q is other than H, C$_{1-6}$ alkyl, (CH$_2$)$_n$-aryl, and (CH$_2$)$_n$-heteroaryl; and/or
 c. R$^e$ is present.

8. A compound of claim 1, wherein:

X, Y, X', and Y', are independently selected from: H, C$_{1-6}$ alkyl, halogen, CF$_3$, O—C$_{1-6}$ alkyl, NO$_2$, NR$_2$, —CN, O(CH$_2$)$_n$CN, NR$^a$SO$_2$R, O(CH$_2$CH$_2$O)$_p$R, NR$^a$(CH$_2$CH$_2$O)$_p$R, and SO$_2$NHCH$_3$;

Z is selected from: H, C$_{1-6}$ alkyl, OH, O—C$_{1-6}$ alkyl, O(CH$_2$CH$_2$O)$_p$R, and OC(O)—C$_{1-6}$ alkyl;

Q is selected from: H, C$_{1-6}$ alkyl, (CH$_2$)$_n$-aryl, (CH$_2$CH$_2$O)$_p$R, and (CH$_2$)$_n$-heteroaryl;

A is selected from H, C$_{1-6}$ alkyl, (CH$_2$)$_m$C$_{3-6}$-cycloalkyl, OH, CH$_2$OH, CH(CH$_3$)OH, C(CH$_3$)$_2$OH, (CH$_2$)$_n$CO$_2$R$^b$, (CH$_2$)$_n$C(O)NR$^b_2$, and (CH$_2$)$_m$-phenyl, wherein the phenyl is substituted with 0-3 groups selected from H, C$_{1-4}$ alkyl, halogen, CF$_3$, OH, O—C$_{1-4}$ alkyl, NO$_2$, —CN, C(O)NH$_2$, C(NH)NH$_2$, and NHSO$_2$CH$_3$;

A" is C$_{1-6}$ alkyl;

R is independently selected from H, (CH$_2$)$_m$(CHR$^b$)$_n$(CH$_2$)$_m$OH, CH(CH$_2$OH)$_2$, C$_{1-6}$ alkyl, C$_{2-6}$ alkenyl, and C$_{2-6}$ alkynyl;

R$^a$ is independently selected from H, (CH$_2$)$_m$(CHR)$_n$(CH$_2$)$_m$OH, C$_{1-6}$ alkyl, C$_{2-6}$ alkenyl, and C$_{2-6}$ alkynyl;

R$^b$ is independently selected from H, C$_{1-6}$ alkyl, C$_{2-6}$ alkenyl, and C$_{2-6}$ alkynyl;

R$^c$ is selected from (CH$_2$)$_m$CHA(CH$_2$)$_m$C(O)NR$^a_2$, (CH$_2$)$_m$CAA"(CH$_2$)$_m$C(O)NR$^a_2$, (CH$_2$)$_m$CHA(CH$_2$)$_m$CO$_2$R, (CH$_2$)$_m$CAA"(CH$_2$)$_m$CO$_2$R, (CH$_2$)$_m$CHA(CH$_2$)$_m$SO$_2$NR$^a_2$, (CH$_2$)$_m$CHA(CH$_2$)$_m$SO$_3$R, (CH$_2$)$_m$CHA(CH$_2$)$_m$C(NH)NH$_2$, (CH$_2$)$_m$CHA(CH$_2$)$_m$C(NOH)NH$_2$, (CH$_2$)$_m$CHA(CH$_2$)$_m$CONHCHA(CH$_2$)$_m$CO$_2$R, (CH$_2$)$_m$CAA"(CH$_2$)$_m$CONHCHA(CH$_2$)$_m$CO$_2$R, (CH$_2$)$_m$CHA(CH$_2$)$_m$CONHCHA(CH$_2$)$_m$CONHCHA(CH$_2$)$_m$CO$_2$R, (CH$_2$)$_m$CHA(CH$_2$)$_m$CONHCHA(CH$_2$)$_m$CONR$^a_2$, (CH$_2$)$_m$CAA"(CH$_2$)$_m$CONHCHA(CH$_2$)$_m$CONR$^a_2$, (CH$_2$)$_m$CHA(CH$_2$)$_m$CONHCHA(CH$_2$)$_m$CONHCHA(CH$_2$)$_m$CONR$^a_2$, C$_3$-C$_6$-cyclic amino-(CH$_2$)$_m$CO$_2$R, C$_3$-C$_6$-cyclic amino-(CH$_2$)$_m$CONR$^a_2$, C$_3$-C$_6$-cycloalkylene-(CH$_2$)$_m$CO$_2$R, and C$_3$-C$_6$-cycloalkylene-(CH$_2$)$_m$CONR$^a_2$;

R$^d$ is selected from H, C$_{1-6}$ alkyl, C$_{2-6}$ alkenyl, C$_{2-6}$ alkynyl, OC$_{3-4}$ alkenyl, OC$_{3-4}$ alkynyl, and C$_{1-6}$ alkylidene-O—C$_{1-2}$ alkyl;

p is independently selected from 2, 3, 4, 5, 6, 7, 8, 9, 10, 11, and 12;

m is independently selected from 0, 1, 2, 3, and 4; and, n is independently selected from 1, 2, 3, and 4.

9. A compound of claim 1, wherein:

X, Y, X', and Y', are independently selected from: H, C$_{1-6}$ alkyl, halogen, CF$_3$, O—C$_{1-6}$ alkyl, NO$_2$, NR$_2$, —CN, NR$^a$SO$_2$R, and SO$_2$NHCH$_3$;

Z is selected from: H, C$_{1-6}$ alkyl, OH, O—C$_{1-6}$ alkyl, O(CH$_2$CH$_2$O)$_p$R, and OC(O)—C$_{1-6}$ alkyl;

Q is selected from: (CH$_2$)$_m$CHA(CH$_2$)$_m$C(O)NR$^a_2$, (CH$_2$)$_m$CAA"(CH$_2$)$_m$C(O)NR$^a_2$, (CH$_2$)$_n$CHA(CH$_2$)$_m$CO$_2$R, (CH$_2$)$_m$CAA"(CH$_2$)$_m$CO$_2$R, (CH$_2$)$_m$CHA(CH$_2$)$_m$SO$_2$NR$^a_2$, (CH$_2$)$_m$CHA(CH$_2$)$_m$SO$_3$R, (CH$_2$)$_m$CHA(CH$_2$)$_m$C(NH)NH$_2$, (CH$_2$)$_m$CHA(CH$_2$)$_m$C(NOH)NH$_2$, (CH$_2$)$_m$CHA(CH$_2$)$_m$CONHCHA(CH$_2$)$_m$CO$_2$R, (CH$_2$)$_m$CAA"(CH$_2$)$_m$CONHCHA(CH$_2$)$_m$CO$_2$R, (CH$_2$)$_m$CHA(CH$_2$)$_m$CONHCHA(CH$_2$)$_m$CONHCHA(CH$_2$)$_m$CO$_2$R, (CH$_2$)$_m$CHA(CH$_2$)$_m$CONHCHA(CH$_2$)$_m$CONR$^a_2$, (CH$_2$)$_m$CAA"(CH$_2$)$_m$CONHCHA(CH$_2$)$_m$CONR$^a_2$, (CH$_2$)$_m$CHA(CH$_2$)$_m$CONHCHA(CH$_2$)$_m$SO$_2$NR$^a_2$, (CH$_2$)$_m$CAA"(CH$_2$)$_m$CONHCHA(CH$_2$)$_m$SO$_2$NR$^a_2$, (CH$_2$)$_m$CHA(CH$_2$)$_m$CONHCHA(CH$_2$)$_m$CONHCHA(CH$_2$)$_m$CONR$^a_2$, C$_3$-C$_6$-cyclic amino-(CH$_2$)$_m$CO$_2$R, C$_3$-C$_6$-cyclic amino-(CH$_2$)$_m$CONR$^a_2$, C$_3$-C$_6$-cycloalkylene-(CH$_2$)$_m$CO$_2$R, and C$_3$-C$_6$-cycloalkylene-(CH$_2$)$_m$CONR$^a_2$;

A is selected from H, C$_{1-6}$ alkyl, (CH$_2$)$_m$C$_{3-6}$-cycloalkyl, OH, CH$_2$OH, CH(CH$_3$)OH, C(CH$_3$)$_2$OH, (CH$_2$)$_n$CO$_2$R$^b$, (CH$_2$)$_n$C(O)NR$^b_2$, and (CH$_2$)$_m$-phenyl, wherein the phenyl is substituted with 0-3 groups selected from H, C$_{1-4}$ alkyl, halogen, CF$_3$, OH, O—C$_{1-4}$ alkyl, NO$_2$, —CN, C(O)NH$_2$, C(NH)NH$_2$, and NHSO$_2$CH$_3$;

A" is C$_{1-6}$ alkyl;

R is independently selected from H, (CH$_2$)$_m$(CHR$^b$)$_n$(CH$_2$)$_m$OH, CH(CH$_2$OH)$_2$, C$_{1-6}$ alkyl, C$_{2-6}$ alkenyl, and C$_{2-6}$ alkynyl;

R$^a$ is independently selected from H, (CH$_2$)$_m$(CHR)$_n$(CH$_2$)$_m$OH, C$_{1-6}$ alkyl, C$_{2-6}$ alkenyl, and C$_{2-6}$ alkynyl;

R$^b$ is independently selected from H, C$_{1-6}$ alkyl, C$_{2-6}$ alkenyl, and C$_{2-6}$ alkynyl;

R$^c$ is selected from H, C$_{1-6}$ alkyl, C$_{2-6}$ alkenyl, C$_{2-6}$ alkynyl, and C$_{1-6}$ alkylidene-O—C$_{1-2}$ alkyl;

R$^d$ is selected from H, C$_{1-6}$ alkyl, C$_{2-6}$ alkenyl, C$_{2-6}$ alkynyl, OC$_{3-4}$ alkenyl, OC$_{3-4}$ alkynyl, and C$_{1-6}$ alkylidene-O—C$_{1-2}$ alkyl;

alternatively, R$^c$ and R$^d$ taken together form —(CH$_2$)$_{n'}$—U—(CH$_2$)$_{n'}$—, and the ring formed by N(R$^c$)CH$_2$R$^d$ is substituted with 0-2 R$^e$ at other than group U;

U is selected from O, S, SO, SO$_2$, CHR$^e$, and NR$^e$;

R$^e$ is selected from H, C$_{1-6}$ alkyl, C$_{3-6}$ alkenyl, C$_{3-6}$ alkynyl, and C$_{2-6}$ alkylidene-O—C$_{1-2}$ alkyl;

p is independently selected from 2, 3, 4, 5, 6, 7, 8, 9, 10, 11, and 12;

m is independently selected from 0, 1, 2, 3, and 4;

n is independently selected from 1, 2, 3, and 4; and, n' is independently selected from 1 and 2.

10. A compound of claim 9, wherein the compound is of Formula Ia or a stereoisomer or pharmaceutically acceptable salt thereof, wherein:

X and X' are independently selected from: H, $C_{1-6}$ alkyl, halogen, $CF_3$, O—$C_{1-6}$ alkyl, $NO_2$, $NR_2$, —CN, $NR^aSO_2R$, and $SO_2NHCH_3$;

Z is selected from: H, $C_{1-6}$ alkyl, OH, and O—$C_{1-6}$ alkyl;

Q is selected from: $(CH_2)_mCHA(CH_2)_mC(O)NR^a{}_2$, $(CH_2)_mCAA''(CH_2)_mC(O)NR^a{}_2$, $(CH_2)_mCHA(CH_2)_mSO_2NR^a{}_2$, $(CH_2)_mCHA(CH_2)_mC(NH)NH_2$, $(CH_2)_mCHA(CH_2)_mCONHCHA(CH_2)_mCONR^a{}_2$, $(CH_2)_mCAA''(CH_2)_mCONHCHA(CH_2)_mCONR^a{}_2$, $(CH_2)_mCHA(CH_2)_mCONHCHA(CH_2)_mSO_2NR^a{}_2$, $(CH_2)_mCAA''(CH_2)_mCONHCHA(CH_2)_mSO_2NR^a{}_2$, $(CH_2)_mCHA(CH_2)_mCONHCHA(CH_2)_mCONHCHA(CH_2)_mCONR^a{}_2$, $C_3$-$C_6$-cyclic amino-$(CH_2)_mCO_2R$, $C_3$-$C_6$-cyclic amino-$(CH_2)_mCONR^a{}_2$, and $C_3$-$C_6$-cycloalkylene-$(CH_2)_mCONR^a{}_2$;

A is selected from H, $C_{1-6}$ alkyl, $(CH_2)_mC_{3-6}$-cycloalkyl, OH, $CH_2OH$, $CH(CH_3)OH$, $C(CH_3)_2OH$, $(CH_2)_nCO_2R^b$, and $(CH_2)_nC(O)NR^b{}_2$;

A" is $C_{1-6}$ alkyl;

R is independently selected from H, $(CH_2)_m(CHR^b)_n$ $(CH_2)_mOH$, $CH(CH_2OH)_2$, $C_{1-6}$ alkyl, $C_{2-6}$ alkenyl, and $C_{2-6}$ alkynyl;

$R^a$ is independently selected from H, $(CH_2)_m(CHR)_n$ $(CH_2)_mOH$, $C_{1-6}$ alkyl, $C_{2-6}$ alkenyl, and $C_{2-6}$ alkynyl;

$R^b$ is independently selected from H, $C_{1-6}$ alkyl, $C_{2-6}$ alkenyl, and $C_{2-6}$ alkynyl;

$R^c$ is selected from H, $C_{1-6}$ alkyl, $C_{2-6}$ alkenyl, $C_{2-6}$ alkynyl, and $C_{1-6}$ alkylidene-O—$C_{1-2}$ alkyl;

$R^d$ is selected from H, $C_{1-6}$ alkyl, $C_{2-6}$ alkenyl, $C_{2-6}$ alkynyl, $OC_{3-4}$ alkenyl, $OC_{3-4}$ alkynyl, and $C_{1-6}$ alkylidene-O—$C_{1-2}$ alkyl;

m is independently selected from 0, 1, and 2;
n is independently selected from 1 and 2; and,
n' is independently selected from 1 and 2.

11. A compound of claim 9, wherein the compound is of Formula Ib or a stereoisomer or pharmaceutically acceptable salt thereof, wherein:

X is selected from: H, $C_{1-6}$ alkyl, halogen, $CF_3$, O—$C_{1-6}$ alkyl, $NO_2$, $NR_2$, and —CN;

Q is selected from: $(CH_2)_mCHA(CH_2)_mC(O)NR^a{}_2$, $(CH_2)_mCAA''(CH_2)_mC(O)NR^a{}_2$, $(CH_2)_mCHA(CH_2)_mSO_2NR^a{}_2$, $(CH_2)_mCHA(CH_2)_mC(NH)NH_2$, $(CH_2)_mCHA(CH_2)_mCONHCHA(CH_2)_mCONR^a{}_2$, $(CH_2)_mCAA''(CH_2)_mCONHCHA(CH_2)_mCONR^a{}_2$, $(CH_2)_mCHA(CH_2)_mCONHCHA(CH_2)_mSO_2NR^a{}_2$, $(CH_2)_mCAA''(CH_2)_mCONHCHA(CH_2)_mSO_2NR^a{}_2$, $(CH_2)_mCHA(CH_2)_mCONHCHA(CH_2)_mCONHCHA(CH_2)_mCONR^a{}_2$, $C_3$-$C_6$-cyclic amino-$(CH_2)_mCO_2R$, $C_3$-$C_6$-cyclic amino-$(CH_2)_mCONR^a{}_2$, and $C_3$-$C_6$-cycloalkylene-$(CH_2)_mCONR^a{}_2$;

A is selected from H, $C_{1-6}$ alkyl, $(CH_2)_mC_{3-6}$-cycloalkyl, OH, $CH_2OH$, $CH(CH_3)OH$, and $C(CH_3)_2OH$;

A" is $C_{1-4}$ alkyl;

R is independently selected from H, $(CH_2)_m(CHR^b)_n$ $(CH_2)_mOH$, $CH(CH_2OH)_2$, $C_{1-4}$ alkyl, $C_{2-4}$ alkenyl, and $C_{2-4}$ alkynyl;

$R^a$ is independently selected from H, $(CH_2)_m(CHR)_n$ $(CH_2)_mOH$, $C_{1-4}$ alkyl, $C_{2-4}$ alkenyl, and $C_{2-4}$ alkynyl;

$R^b$ is independently selected from H, $C_{1-4}$ alkyl, $C_{2-4}$ alkenyl, and $C_{2-4}$ alkynyl;

$R^c$ is selected from H, $C_{1-4}$ alkyl, $C_{2-4}$ alkenyl, $C_{2-4}$ alkynyl, and $C_{1-4}$ alkylidene-O—$C_{1-2}$ alkyl;

$R^d$ is selected from H, $C_{1-4}$ alkyl, $C_{2-4}$ alkenyl, $C_{2-4}$ alkynyl, $OC_{3-4}$ alkenyl, $OC_{3-4}$ alkynyl, and $C_{1-4}$ alkylidene-O—$C_{1-2}$ alkyl;

m is independently selected from 0, 1, and 2;
n is independently selected from 1 and 2; and,
n' is independently selected from 1 and 2.

12. A compound of claim 1, wherein the compound is selected from formula

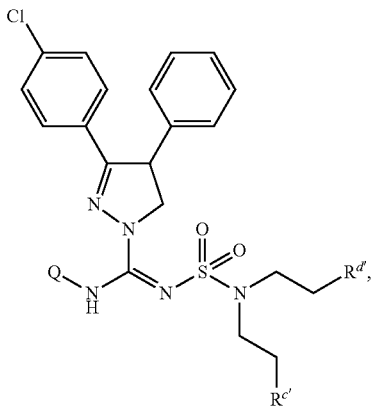

wherein Q, $R^{c'}$, and $R^{d'}$ are defined as follows:

| Ex. # | Q | $R^{c'}$ | $R^{d'}$ |
|---|---|---|---|
| 1 | $CHCH_3CONH_2$ | H | H |
| 2 | $CH_2CONH_2$ | H | H |
| 3 | $CHCH_3CONH_2$ | $OCH_3$ | $OCH_3$ |
| 4 | $CH_2CO_2CH_3$ | H | $OCH_3$ |
| 5 | $CHCH_3CO_2CH_3$ | H | $OCH_3$ |
| 6 | $CH_2CONH_2$ | H | $OCH_3$ |
| 7 | $CHCH_3CONH_2$ | H | $OCH_3$ |
| 8 | $CH(CH(CH_3)_2)$—$CONH_2$ | H | $OCH_3$ |
| 9 | $CH(CHOHCH_3)$—$CONH_2$ | H | $OCH_3$ |
| 10 | $CH_2CH_2SO_2NH_2$ | H | $OCH_3$ |
| 11 | $CH_2CHCH_3$—$CONH_2$ | H | $OCH_3$ |
| 12 | $CH(CH(CH_3)_2)$—$CONH_2$ | H | H |
| 13 | $CH(CHOHCH_3)$—$CONH_2$ | H | H |
| 14 | $CH_2CH_2CONH_2$ | H | $OCH_3$ |
| 15 | $CH_2CH_2CH_2$—$SO_2NH_2$ | H | H |
| 16 | $CH_2CONHCH_2$—$CH_2SO_2NH_2$ | H | H |
| 17 | $CH_2CHOHCH_2$—$CONH_2$ | H | H |

-continued

| Ex. # | Q | $R^{c'}$ | $R^{d'}$ |
|---|---|---|---|
| 18 | CH(C$_6$H$_5$)CONH$_2$ | H | H |
| 19 | CH$_2$CHOHCH$_3$—CH$_2$CONH$_2$ | H | OCH$_3$ | formula

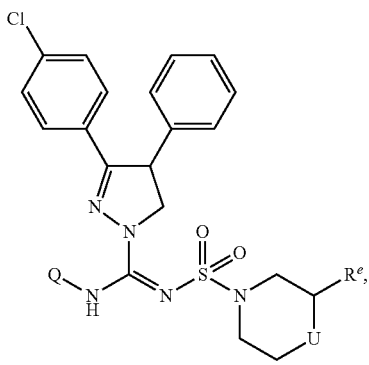

wherein Q, $R^e$, and U are defined as follows:

| Ex. # | Q | U | $R^e$ |
|---|---|---|---|
| 1. | CH$_3$ | CH$_2$ | CHCO$_2$Et |
| 2 | CH$_3$ | O | CHCO$_2$Et |
| 3 | CH$_3$ | O | CHCONH$_2$ |
| 4 | CH$_3$ | CHCO$_2$Et | H |
| 5 | CH$_3$ | CHCONH$_2$ | H |
| 6 | CH$_2$CONH$_2$ | O | H |
| 7 | CHCH$_3$CO$_2$CH$_3$ | O | H |
| 8 | CHCH$_3$CONH$_2$ | O | H |
| 9 | CH(CHOH—(CH$_3$))CO$_2$CH$_3$ | O | H |
| 10 | CHCH(CH$_3$)$_2$CO$_2$CH$_3$ | O | H |
| 11 | CHCH(CH$_3$)$_2$CONH$_2$ | O | H |
| 12 | CHCHOHCH$_3$CONH$_2$ | O | H | or
formula

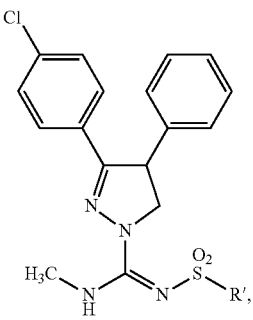

wherein R' is defined as follows:

| Ex # | R' |
|---|---|
| 1 | N(CH$_3$)CH$_2$CONH$_2$ |
| 2 | N(CH$_3$)CH$_2$CO$_2$CH$_3$ | and a stereoisomer or a pharmaceutically acceptable salt thereof.

13. A compound of claim 1, wherein the compound is selected from formula

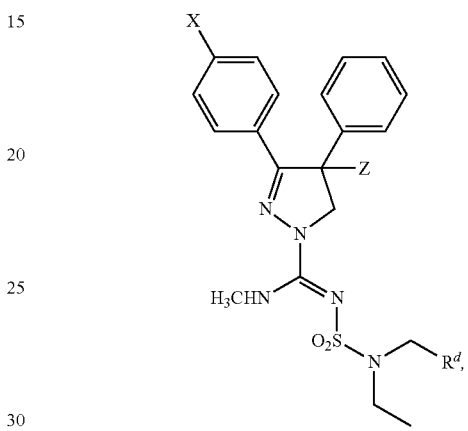

wherein X, Z, and $R^d$ are defined as follows:

| Ex. # | X | Z | $R^d$ |
|---|---|---|---|
| 1. | C(NH)NH$_2$ | H | H |
| 2. | OCH$_2$-tetrazole | H | H |
| 3. | tetrazole | H | H |
| 4. | NHSO$_2$CH$_3$ | H | H |
| 5. | OCH$_2$CO$_2$Et | H | H |
| 6. | OCH$_2$CO$_2$H | H | H |
| 7. | OCH$_2$CH=CHCO$_2$Et | H | H |
| 8. | OCH$_2$CH=CHCO$_2$H | H | H |
| 9. | NHCOCH$_2$CO$_2$Et | H | H |
| 10. | CHCOCH$_2$CO$_2$H | H | H |
| 11. | OCH$_2$C$_6$H$_4$-2-CO$_2$Et | H | H |
| 12. | OCH$_2$C$_6$H$_4$-3-CO$_2$Et | H | H |
| 13. | OCH$_2$C$_6$H$_4$-4-CO$_2$Et | H | H |
| 14. | OCH$_2$C$_6$H$_4$-2-CO$_2$H | H | H |
| 15. | OCH$_2$C$_6$H$_4$-3-CO$_2$H | H | H |
| 16. | OCH$_2$C$_6$H$_4$-4-CO$_2$H | H | H |
| 17. | OCH$_2$C$_6$H$_4$-2-tetrazole | H | H |
| 18. | OCH$_2$C$_6$H$_4$-3-tetrazole | H | H |
| 19. | OCH$_2$C$_6$H$_4$-4-tetrazole | H | H |
| 20. | C(NH)NH2 | OH | H |
| 21. | OCH$_2$-tetrazole | OH | H |
| 22. | tetrazole | OH | H |
| 23. | NHSO$_2$CH$_3$ | OH | H |
| 24. | OCH$_2$CO$_2$Et | OH | H |
| 25. | OCH$_2$CO$_2$H | OH | H |
| 26. | OCH$_2$CH=CHCO$_2$Et | OH | H |
| 27. | OCH$_2$CH=CHCOHD 2H | OH | H |
| 28. | NHCOCH$_2$CO$_2$Et | OH | H |
| 29. | NHCOCH$_2$CO$_2$H | OH | H |
| 30. | OCH$_2$C$_6$H$_4$-2-CO$_2$Et | OH | H |
| 31. | OCH$_2$C$_6$H$_4$-3-CO$_2$Et | OH | H |
| 32. | OCH$_2$C$_6$H$_4$-4-CO$_2$Et | OH | H |
| 33. | OCH$_2$C$_6$H$_4$-2-CO$_2$H | OH | H |
| 34. | OCH$_2$C$_6$H$_4$-3-CO$_2$H | OH | H |
| 35. | OCH$_2$CPHD 6H$_4$-4-CO$_2$H | OH | H |
| 36. | OCH$_2$C$_6$H$_4$-2-tetrazole | OH | H |
| 37. | OCH$_2$C$_6$H$_4$-3-tetrazole | OH | H |
| 38. | OCH$_2$C$_6$H$_4$-4-tetrazole | OH | H |

-continued

| Ex. # | X | Z | $R^d$ |
|---|---|---|---|
| 39. | C(NH)NH$_2$ | H | CH$_2$OCH$_3$ |
| 40. | OCH$_2$-tetrazole | H | CH$_2$OCH$_3$ |
| 41. | tetrazole | H | CH$_2$OCH$_3$ |
| 42. | NHSO$_2$CH$_3$ | H | CH$_2$OCH$_3$ |
| 43. | OCH$_2$CO$_2$Et | H | CH$_2$OCH$_3$ |
| 44. | OCH$_2$CO$_2$H | H | CH$_2$OCH$_3$ |
| 45. | OCH$_2$CH=CHCO$_2$Et | H | CH$_2$OCH$_3$ |
| 46. | OCH$_2$CH=CHCO$_2$H | H | CH$_2$OCH$_3$ |
| 47. | NHCOCH$_2$CO$_2$Et | H | CH$_2$OCH$_3$ |
| 48. | NHCOCH$_2$CO$_2$H | H | CH$_2$OCH$_3$ |
| 49. | OCH$_2$C$_6$H$_4$-4-CO$_2$Et | H | CH$_2$OCH$_3$ |
| 50. | OCH$_2$C$_6$H$_4$-3-CO$_2$Et | H | CH$_2$OCH$_3$ |
| 51. | OCH$_2$C$_6$H$_4$-4-CO$_2$Et | H | CH$_2$OCH$_3$ |
| 52. | OCH$_2$C$_6$H$_4$-2-CO$_2$H | H | CH$_2$OCH$_3$ |
| 53. | OCH$_2$C$_6$H$_4$-3-CO$_2$H | H | CH$_2$OCH$_3$ |
| 54. | OCH$_2$C$_6$H$_4$-4-CO$_2$H | H | CH$_2$OCH$_3$ |
| 55. | OCH$_2$C$_6$H$_4$-2-tetrazole | H | CH$_2$OCH$_3$ |
| 56. | OCH$_2$C$_6$H$_4$-3-tetrazole | H | CH$_2$OCH$_3$ |
| 57. | OCH$_2$C$_6$H$_4$-4-tetrazole | H | CH$_2$OCH$_3$ |
| 58. | C(NH)NH2 | OH | CH$_2$OCH$_3$ |
| 59. | OCH$_2$-tetrazole | OH | CH$_2$OCH$_3$ |
| 60. | tetrazole | OH | CH$_2$OCH$_3$ |
| 61. | NHSO$_2$CH$_3$ | OH | CH$_2$OCH$_3$ |
| 62. | OCH$_2$CO$_2$Et | OH | CH$_2$OCH$_3$ |
| 63. | OCH$_2$CO$_2$H | OH | CH$_2$OCH$_3$ |
| 64. | OCH$_2$CH=CHCO$_2$Et | OH | CH$_2$OCH$_3$ |
| 65. | OCH$_2$CH=CHCO$_2$H | OH | CH$_2$OCH$_3$ |
| 66. | NHCOCH$_2$CO$_2$Et | OH | CH$_2$OCH$_3$ |
| 67. | NHCOCH$_2$CO$_2$H | OH | CH$_2$OCH$_3$ |
| 68. | OCH$_2$C$_6$H$_4$-2-Co$_2$Et | OH | CH$_2$OCH$_3$ |
| 69. | OCH$_2$C$_6$H$_3$-3-CO$_2$Et | OH | CH$_2$OCH$_3$ |
| 70. | OCH$_2$C$_6$H$_4$-4-CO$_2$Et | OH | CH$_2$OCH$_3$ |
| 71. | OCH$_2$C$_6$H$_4$-2-CO$_2$H | OH | CH$_2$OCH$_3$ |
| 72. | OCH$_2$C$_6$H$_4$-3-CO$_2$H | OH | CH$_2$OCH$_3$ |
| 73. | OCH$_2$C$_6$H$_4$-4-CO$_2$H | OH | CH$_2$OCH$_3$ |
| 74. | OCH$_2$C$_6$H$_4$-2-tetrazole | OH | CH$_2$OCH$_3$ |
| 75. | OCH$_2$C$_6$H$_4$-3-tetrazole | OH | CH$_2$OCH$_3$ |
| 76. | OCH$_2$C$_6$H$_4$-4-tetrazole | OH | CH$_2$OCH$_3$ | formula

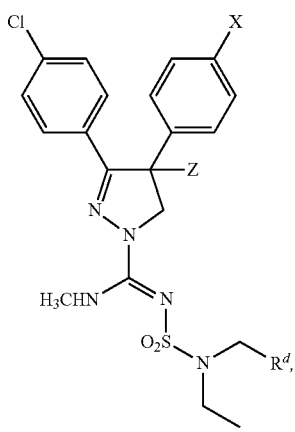

wherein X, Z, and $R^d$ are defined as follows:

| Ex. # | X | Z | $R^d$ |
|---|---|---|---|
| 1. | C(NH)NH$_2$ | H | H |
| 2. | OCH$_2$-tetrazole | H | H |
| 3. | tetrazole | H | H |
| 4. | NHSO$_2$CH$_3$ | H | H |
| 5. | OCH$_2$CO$_2$Et | H | H |
| 6. | OCH$_2$CO$_2$H | H | H |
| 7. | OCH$_2$CH=CHCO$_2$Et | H | H |
| 8. | OCH$_2$CH=CHCO$_2$H | H | H |
| 9. | NHCOCH$_2$CO$_2$Et | H | H |
| 10. | NHCOCH$_2$CO$_2$H | H | H |
| 11. | OCH$_2$C$_6$H$_4$-2-CO$_2$Et | H | H |
| 12. | OCH$_2$C$_6$H$_4$-3-CO$_2$Et | H | H |
| 13. | OCH$_2$C$_6$H$_4$-4-CO$_2$Et | H | H |
| 14. | OCH$_2$C$_6$H$_4$-2-CO$_2$H | H | H |
| 15. | OCH$_2$C$_6$H$_4$-3-CO$_2$H | H | H |
| 16. | OCH$_2$C$_6$H$_4$-4-CO$_2$H | H | H |
| 17. | OCH$_2$C$_6$H$_4$-2-tetrazole | H | H |
| 18. | OCH$_2$C$_6$H$_4$-3-tetrazole | H | H |
| 19. | OCH$_2$C$_6$H$_4$-4-tetrazole | H | H |
| 20. | C(NH)NH2 | OH | H |
| 21. | OCH$_2$-tetrazole | OH | H |
| 22. | tetrazole | OH | H |
| 23. | NHSO$_2$CH$_3$ | OH | H |
| 24. | OCH$_2$CO$_2$Et | OH | H |
| 25. | OCH$_2$CO$_2$H | OH | H |
| 26. | OCH$_2$CH=CHCO$_2$Et | OH | H |
| 27. | OCH$_2$CH=CHCO$_2$H | OH | H |
| 28. | NHCOCH$_2$CO$_2$Et | OH | H |
| 29. | NHCOCH$_2$CO$_2$H | OH | H |
| 30. | OCH$_2$C$_6$H$_4$-2-CO$_2$Et | OH | H |
| 31. | OCH$_2$C$_6$H$_4$-3-CO$_2$Et | OH | H |
| 32. | OCH$_2$C$_6$H$_4$-4-CO$_2$Et | OH | H |
| 33. | OCH$_2$C$_6$H$_4$-2-CO$_2$H | OH | H |
| 34. | OCH$_2$C$_6$H$_4$-3-CO$_2$H | OH | H |
| 35. | OCH$_2$C$_6$H$_4$-4-CO$_2$H | OH | H |
| 36. | OCH$_2$C$_6$H$_4$-2-tetrazole | OH | H |
| 37. | OCH$_2$C$_6$H$_4$-3-tetrazole | OH | H |
| 38. | OCH$_2$C$_6$H$_4$-4- tetrazole | OH | H |
| 39. | C(NH)NH$_2$ | H | CH$_2$OCH$_3$ |
| 40. | OCH$_2$-tetrazole | H | CH$_2$OCH$_3$ |
| 41. | tetrazole | H | CH$_2$OCH$_3$ |
| 42. | NHSO$_2$CH$_3$ | H | CH$_2$OCH$_3$ |
| 43. | OCH$_2$CO$_2$Et | H | CH$_2$OCH$_3$ |
| 44. | OCH$_2$CO$_2$H | H | CH$_2$OCH$_3$ |
| 45. | OCH$_2$CH=CHCO$_2$Et | H | CH$_2$OCH$_3$ |
| 46. | OCH$_2$CH=CHCO$_2$H | H | CH$_2$OCH$_3$ |
| 47. | NHCOCH$_2$CO$_2$Et | H | CH$_2$OCH$_3$ |
| 48. | NHCOCH$_2$CO$_2$H | H | CH$_2$OCH$_3$ |
| 49. | OCH$_2$C$_6$H$_4$-2-CO$_2$Et | H | CH$_2$OCH$_3$ |
| 50. | OCH$_2$C$_6$H$_4$-3-CO$_2$Et | H | CH$_2$OCH$_3$ |
| 51. | OCH$_2$C$_6$H$_4$-4-CO$_2$Et | H | CH$_2$OCH$_3$ |
| 52. | OCH$_2$C$_6$H$_4$-2-CO$_2$H | H | CH$_2$OCH$_3$ |
| 53. | OCH$_2$C$_6$H$_4$-3-CO$_2$H | H | CH$_2$OCH$_3$ |
| 54. | OCH$_2$C$_6$H$_4$-4-CO$_2$H | H | CH$_2$OCH$_3$ |
| 55. | OCH$_2$C$_6$H$_4$-2-tetrazole | H | CH$_2$OCH$_3$ |
| 56. | OCH$_2$C$_6$H$_4$-3-tetrazole | H | CH$_2$OCH$_3$ |
| 57. | OCH$_2$C$_6$H$_4$-4-tetrazole | H | CH$_2$OCH$_3$ |
| 58. | C(NH)NH2 | OH | CH$_2$OCH$_3$ |
| 59. | OCH$_2$-tetrazole | OH | CH$_2$OCH$_3$ |
| 60. | tetrazole | OH | CH$_2$OCH$_3$ |
| 61. | NHSO$_2$CH$_3$ | OH | CH$_2$OCH$_3$ |
| 62. | OCH$_2$CO$_2$Et | OH | CH$_2$OCH$_3$ |
| 63. | OCH$_2$CO$_2$H | OH | CH$_2$OCH$_3$ |
| 64. | OCH$_2$CH=CHCO$_2$Et | OH | CH$_2$OCH$_3$ |
| 65. | OCH$_2$CH=CHCO$_2$H | OH | CH$_2$OCH$_3$ |
| 66. | NHCOCH$_2$CO$_2$Et | OH | CH$_2$OCH$_3$ |
| 67. | NHCOCH$_2$CO$_2$H | OH | CH$_2$OCH$_3$ |
| 68. | OCH$_2$C$_6$H$_4$-2-CO$_2$Et | OH | CH$_2$OCH$_3$ |
| 69. | OCH$_2$C$_6$H$_4$-3-CO$_2$Et | OH | CH$_2$OCH$_3$ |
| 70. | OCH$_2$C$_6$H$_4$-4-CO$_2$Et | OH | CH$_2$OCH$_3$ |
| 71. | OCH$_2$C$_6$H$_4$-2-CO$_2$H | OH | CH$_2$OCH$_3$ |
| 72. | OCH$_2$C$_6$H$_4$-3-CO$_2$H | OH | CH$_2$OCH$_3$ |
| 73. | OCH$_2$C$_6$H$_4$-4-CO$_2$H | OH | CH$_2$OCH$_3$ |

-continued

| Ex. # | X | Z | R$^d$ |
|---|---|---|---|
| 74. | OCH$_2$C$_6$H$_4$-2-tetrazole | OH | CH$_2$OCH$_3$ |
| 75. | OCH$_2$C$_6$H$_4$-3-tetrazole | OH | CH$_2$OCH$_3$ |
| 76. | OCH$_2$C$_6$H$_4$-4-tetrazole | OH | CH$_2$OCH$_3$ | formula

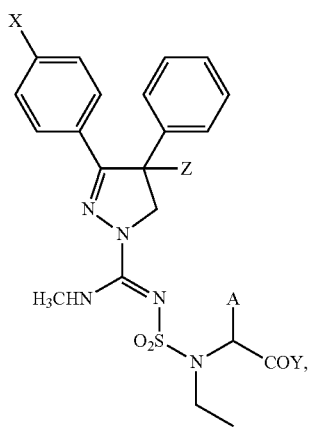

wherein X, Z, A, and Y are defined as follows:

| Ex. # | A | X | Y | Z |
|---|---|---|---|---|
| 1. | H | Cl | OEt | H |
| 2. | H | OCH$_3$ | OEt | H |
| 3. | H | NHSO$_2$CH$_3$ | OEt | H |
| 4. | H | CN | OEt | H |
| 5. | H | C(NH)NH2 | OEt | H |
| 6. | H | OCH$_2$CONH$_2$ | OEt | H |
| 7. | H | Cl | OH | H |
| 8. | H | OCH$_3$ | OH | H |
| 9. | H | NHSO$_2$CH$_3$ | OH | H |
| 10. | H | CN | OH | H |
| 11. | H | C(NH)NH2 | OH | H |
| 12. | H | OCH$_2$CONH$_2$ | OH | H |
| 13. | H | Cl | NH$_2$ | H |
| 14. | H | OCH$_3$ | NH$_2$ | H |
| 15. | H | NHSO$_2$CH$_3$ | NH$_2$ | H |
| 16. | H | CN | NH$_2$ | H |
| 17. | H | C(NH)NH2 | NH$_2$ | H |
| 18. | H | OCH$_2$CONH$_2$ | NH$_2$ | H |
| 19. | H | Cl | NHCH$_2$CONH$_2$ | H |
| 20. | H | OCH$_3$ | NHCH$_2$CONH$_2$ | H |
| 21. | H | NHSO$_2$CH$_3$ | NHCH$_2$CONH$_2$ | H |
| 22. | H | CN | NHCH$_2$CONH$_2$ | H |
| 23. | H | C(NH)NH2 | NHCH$_2$CONH$_2$ | H |
| 24. | H | OCH$_2$CONH$_2$ | NHCH$_2$CONH$_2$ | H |
| 25. | H | OCH$_3$ | OEt | H |
| 26. | H | NHSO$_2$CH$_3$ | OEt | H |
| 27. | H | CN | OEt | H |
| 28. | H | C(NH)NH$_2$ | OEt | H |
| 29. | H | OCH$_2$CONH$_2$ | OEt | H |
| 30. | H | OCH$_2$CONH$_2$ | OEt | OH |
| 31. | H | Cl | OH | OH |
| 32. | H | OCH$_3$ | OH | OH |
| 33. | H | NHSO$_2$CH$_3$ | OH | OH |
| 34. | H | CN | OH | OH |
| 35. | H | C(NH)NH$_2$ | OH | OH |
| 36. | H | OCH$_2$CONH$_2$ | OH | OH |
| 37. | H | Cl | NH$_2$ | OH |
| 38. | H | OCH$_3$ | NH$_2$ | OH |
| 39. | H | NHSO$_2$CH$_3$ | NH$_2$ | OH |
| 40. | H | CN | NH$_2$ | OH |
| 41. | H | C(NH)NH2 | NH$_2$ | OH |
| 42. | H | OCH$_2$CONH$_2$ | NH$_2$ | OH |
| 43. | H | Cl | NHCH$_2$CONH$_2$ | OH |
| 44. | H | OCH$_3$ | NHCH$_2$CONH$_2$ | OH |
| 45. | H | NHSO$_2$CH$_3$ | NHCH$_2$CONH$_2$ | OH |
| 46. | H | CN | NHCH$_2$CONH$_2$ | OH |
| 47. | H | C(NH)NH2 | NHCH$_2$CONH$_2$ | OH |
| 48. | H | OCH$_2$CONH$_2$ | NHCH$_2$CONH$_2$ | OH |
| 49. | CH(CH$_3$)OH | Cl | OEt | H |
| 50. | CH(CH$_3$)OH | OCH$_3$ | OEt | H |
| 51. | CH(CH$_3$)OH | NHSO$_2$CH$_3$ | OEt | H |
| 52. | CH(CH$_3$)OH | CN | OEt | H |
| 53. | CH(CH$_3$)OH | C(NH)NH2 | OEt | H |
| 54. | CH(CH$_3$)OH | OCH$_2$CONH$_2$ | OEt | H |
| 55. | CH(CH$_3$)OH | Cl | OH | H |
| 56. | CH(CH$_3$)OH | OCH$_3$ | OH | H |
| 57. | CH(CH$_3$)OH | NHSO$_2$CH$_3$ | OH | H |
| 58. | CH(CH$_3$)OH | CN | OH | H |
| 59. | CH(CH$_3$)OH | C(NH)NH2 | OH | H |
| 60. | CH(CH$_3$)OH | OCH$_2$CONH$_2$ | OH | H |
| 61. | CH(CH$_3$)OH | Cl | NH$_2$ | H |
| 62. | CH(CH$_3$)OH | OCH$_3$ | NH$_2$ | H |
| 63. | CH(CH$_3$)OH | NHSO$_2$CH$_3$ | NH$_2$ | H |
| 64. | CH(CH$_3$)OH | CN | NH$_2$ | H |
| 65. | CH(CH$_3$)OH | C(NH)NH2 | NH$_2$ | H |
| 66. | CH(CH$_3$)OH | OCH$_2$CONH$_2$ | NH$_2$ | H |
| 67. | CH(CH$_3$)OH | Cl | NHCH$_2$CONH$_2$ | H |
| 68. | CH(CH$_3$)OH | OCH$_3$ | NHCH$_2$CONH$_2$ | H |
| 69. | CH(CH$_3$)OH | NHSO$_2$CH$_3$ | NHCH$_2$CONH$_2$ | H |
| 70. | CH(CH$_3$)OH | CN | NHCH$_2$CONH$_2$ | H |
| 71. | CH(CH$_3$)OH | C(NH)NH2 | NHCH$_2$CONH$_2$ | H |
| 72. | CH(CH$_3$)OH | OCH$_2$CONH$_2$ | NHCH$_2$CONH$_2$ | H |
| 73. | CH(CH$_3$)OH | OCH$_3$ | OEt | H |
| 74. | CH(CH$_3$)OH | NHSO$_2$CH$_3$ | OEt | H |
| 75. | CH(CH$_3$)OH | CN | OEt | H |
| 76. | CH(CH$_3$)OH | C(NH)NH2 | OEt | H |
| 77. | CH(CH$_3$)OH | OCH$_2$CONH$_2$ | OEt | H |
| 78. | CH(CH$_3$)OH | OCH$_2$CONH$_2$ | OEt | OH |
| 79. | CH(CH$_3$)OH | Cl | OH | OH |
| 80. | CH(CH$_3$)OH | OCH$_3$ | OH | OH |
| 81. | CH(CH$_3$)OH | NHSO$_2$CH$_3$ | OH | OH |
| 82. | CH(CH$_3$)OH | CN | OH | OH |
| 83. | CH(CH)OH | C(NH)NH2 | OH | OH |
| 84. | CH(CH$_3$)OH | OCH$_2$CONH$_2$ | OH | OH |
| 85. | CH(CH$_3$)OH | Cl | NH$_2$ | OH |
| 86. | CH(CH$_3$)OH | OCH$_3$ | NH$_2$ | OH |
| 87. | CH(CH$_3$)OH | NHSO$_2$CH$_3$ | NH$_2$ | OH |
| 88. | CH(CH$_3$)OH | CN | NH$_2$ | OH |
| 89. | CH(CH$_3$)OH | C(NH)NH2 | NH$_2$ | OH |
| 90. | CH(CH$_3$)OH | OCH$_2$CONH$_2$ | NH$_2$ | OH |
| 91. | CH(CH$_3$)OH | Cl | NHCH$_2$CONH$_2$ | OH |
| 92. | CH(CH$_3$)OH | OCH$_3$ | NHCH$_2$CONH$_2$ | OH |
| 93. | CH(CH$_3$)OH | NHSO$_2$CH$_3$ | NHCH$_2$CONH$_2$ | OH |

-continued

| Ex. # | A | X | Y | Z |
|---|---|---|---|---|
| 94. | CH(CH₃)OH | CN | NHCH₂CONH₂ | OH |
| 95. | CH(CH₃)OH | C(NH)NH2 | NHCH₂CONH₂ | OH |
| 96. | CH(CH₃)OH | OCH₂CONH₂ | NHCH₂CONH₂ | OH | or formula

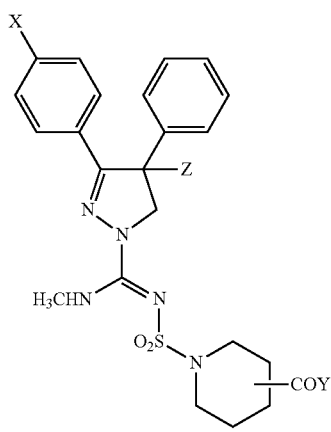

wherein X, Z, and Y are defined as follows:

| Ex. # | X | Y(ring position) | Z |
|---|---|---|---|
| 1. | Cl | OEt (3) | H |
| 2. | OCH₃ | OEt (3) | H |
| 3. | NHSO₂CH₃ | OEt (3) | H |
| 4. | CN | OEt (3) | H |
| 5. | C(NH)NH2 | OEt (3) | H |
| 6. | OCH₂CONH₂ | OEt (3) | H |
| 7. | Cl | OH (3) | H |
| 8. | OCH₃ | OH (3) | H |
| 9. | NHSO₂CH₃ | OH (3) | H |
| 10. | CN | OH (3) | H |
| 11. | C(NH)NH2 | OH (3) | H |
| 12. | OCH₂CONH₂ | OH (3) | H |
| 13. | Cl | NH₂ (3) | H |
| 14. | OCH₃ | NH₂ (3) | H |
| 15. | NHSO₂CH₃ | NH₂ (3) | H |
| 16. | CN | NH₂ (3) | H |
| 17. | C(NH)NH2 | NH₂ (3) | H |
| 18. | OCH₂CONH₂ | NH₂ (3) | H |
| 19. | Cl | NHCH₂CONH₂ (3) | H |
| 20. | OCH₃ | NHCH₂CONH₂ (3) | H |
| 21. | NHSO₂CH₃ | NHCH₂CONH₂ (3) | H |
| 22. | CN | NHCH₂CONH₂ (3) | H |
| 23. | C(NH)NH2 | NHCH₂CONH₂ (3) | H |
| 24. | OCH₂CONH₂ | NHCH₂CONH₂ (3) | H |
| 25. | OCH₃ | OEt (4) | H |
| 26. | NHSO₂CH₃ | OEt (4) | H |
| 27. | CN | OEt (4) | H |
| 28. | C(NH)NH2 | OEt (4) | H |
| 29. | OCH₂CONH₂ | OEt (4) | H |
| 30. | OCH₂CONH₂ | OEt (4) | H |
| 31. | Cl | OH (4) | H |
| 32. | OCH₃ | OH (4) | H |
| 33. | NHSO₂CH₃ | OH (4) | H |
| 34. | CN | OH (4) | H |
| 35. | C(NH)NH2 | OH (4) | H |
| 36. | OCH₂CONH₂ | OH (4) | H |
| 37. | Cl | NH₂ (4) | H |
| 38. | OCH₃ | NH₂ (4) | H |
| 39. | NHSO₂CH₃ | NH₂ (4) | H |
| 40. | CN | NH₂ (4) | H |
| 41. | C(NH)NH2 | NH₂ (4) | H |
| 42. | OCH₂CONH₂ | NH₂ (4) | H |
| 43. | Cl | NHCH₂CONH₂ (4) | H |
| 44. | OCH₃ | NHCH₂CONH₂ (4) | H |
| 45. | NHSO₂CH₃ | NHCH₂CONH₂ (4) | H |
| 46. | CN | NHCH₂CONH₂ (4) | H |
| 47. | C(NH)NH2 | NHCH₂CONH₂ (4) | H |
| 48. | OCH₂CONH₂ | NHCH₂CONH₂ (4) | H |
| 49. | Cl | OEt (3) | OH |
| 50. | OCH₃ | OEt (3) | OH |
| 51. | NHSO₂CH₃ | OEt (3) | OH |
| 52. | CN | OEt (3) | OH |
| 53. | C(NH)NH2 | OEt (3) | OH |
| 54. | OCH₂CONH₂ | OEt (3) | OH |
| 55. | Cl | OH (3) | OH |
| 56. | OCH₃ | OH (3) | OH |
| 57. | NHSO₂CH₃ | OH (3) | OH |
| 58. | CN | OH (3) | OH |
| 59. | C(NH)NH2 | OH (3) | OH |
| 60. | OCH₂CONH₂ | OH (3) | OH |
| 61. | Cl | NH₂ (3) | OH |
| 62. | OCH₃ | NH₂ (3) | OH |
| 63. | NHSO₂CH₃ | NH₂ (3) | OH |
| 64. | CN | NH₂ (3) | OH |
| 65. | C(NH)NH2 | NH₂ (3) | OH |
| 66. | OCH₂CONH₂ | NH₂ (3) | OH |
| 67. | Cl | NHCH₂CONH₂ (3) | OH |
| 68. | OCH₃ | NHCH₂CONH₂ (3) | OH |
| 69. | NHSO₂CH₃ | NHCH₂CONH₂ (3) | OH |
| 70. | CN | NHCH₂CONH₂ (3) | OH |
| 71. | C(NH)NH2 | NHCH₂CONH₂ (3) | OH |
| 72. | OCH₂CONH₂ | NHCH₂CONH₂ (3) | OH |
| 73. | OCH₃ | OEt (4) | OH |
| 74. | NHSO₂CH₃ | OEt (4) | OH |
| 75. | CN | OEt (4) | OH |
| 76. | C(NH)NH2 | OEt (4) | OH |
| 77. | OCH₂CONH₂ | OEt (4) | OH |
| 78. | OCH₂CONH₂ | OEt (4) | OH |
| 79. | Cl | OH (4) | OH |
| 80. | OCH₃ | OH (4) | OH |
| 81. | NHSO₂CH₃ | OH (4) | OH |
| 82. | CN | OH (4) | OH |
| 83. | C(NH)NH2 | OH (4) | OH |
| 84. | OCH₂CONH₂ | OH (4) | OH |
| 85. | Cl | NH₂ (4) | OH |
| 86. | OCH₃ | NH₂ (4) | OH |
| 87. | NHSO₂CH₃ | NH₂ (4) | OH |
| 88. | CN | NH₂ (4) | OH |
| 89. | C(NH)NH2 | NH₂ (4) | OH |
| 90. | OCH₂CONH₂ | NH₂ (4) | OH |
| 91. | Cl | NHCH₂CONH₂ (4) | OH |
| 92. | OCH₃ | NHCH₂CONH₂ (4) | OH |
| 93. | NHSO₂CH₃ | NHCH₂CONH₂ (4) | OH |
| 94. | CN | NHCH₂CONH₂ (4) | OH |
| 95. | C(NH)NH2 | NHCH₂CONH₂ (4) | OH |
| 96. | OCH₂CONH₂ | NHCH₂CONH₂ (4) | OH | and a stereoisomer or a pharmaceutically acceptable salt thereof.

14. A pharmaceutical composition, comprising: a compound of claim 1 and a pharmaceutically acceptable carrier.

* * * * *